US012558413B2

(12) United States Patent
Hartigan-O'Connor

(10) Patent No.: US 12,558,413 B2
(45) Date of Patent: Feb. 24, 2026

(54) IL-10 INHIBITION FOR VACCINES AND IMMUNOTHERAPY

(71) Applicant: The Regents of the University of California, Oakland, CA (US)

(72) Inventor: Dennis Hartigan-O'Connor, Davis, CA (US)

(73) Assignee: The Regents of the University of California, Oakland, CA (US)

(*) Notice: Subject to any disclaimer, the term of this patent is extended or adjusted under 35 U.S.C. 154(b) by 1112 days.

(21) Appl. No.: 17/173,118

(22) Filed: Feb. 10, 2021

(65) Prior Publication Data

US 2021/0299243 A1 Sep. 30, 2021

Related U.S. Application Data

(63) Continuation of application No. PCT/US2019/046503, filed on Aug. 14, 2019.

(60) Provisional application No. 62/845,671, filed on May 9, 2019, provisional application No. 62/764,848, filed on Aug. 15, 2018.

(51) Int. Cl.

*A61K 39/21* (2006.01)
*A61K 38/17* (2006.01)
*A61K 38/20* (2006.01)
*A61K 39/00* (2006.01)
*A61K 39/395* (2006.01)
*C07K 16/24* (2006.01)

(52) U.S. Cl.

CPC .......... *A61K 39/21* (2013.01); *A61K 38/1709* (2013.01); *A61K 38/1793* (2013.01); *A61K 38/2066* (2013.01); *A61K 39/00* (2013.01); *A61K 39/0011* (2013.01); *A61K 39/3955* (2013.01); *C07K 16/244* (2013.01); *A61K 2039/505* (2013.01); *A61K 2039/5256* (2013.01); *A61K 2039/55* (2013.01); *C07K 2319/30* (2013.01); *C12N 2710/10034* (2013.01); *C12N 2710/16134* (2013.01); *C12N 2740/15034* (2013.01); *C12N 2740/16034* (2013.01)

(58) Field of Classification Search

CPC ............ A61K 38/2066; A61K 2300/00; A61K 39/3955; A61K 2039/505; A61K 39/12

See application file for complete search history.

(56) References Cited

U.S. PATENT DOCUMENTS 8,420,784 B2 * 4/2013 Kato ....................... A61P 31/10 424/139.1
9,492,499 B2 * 11/2016 Jaynes .................... A61P 11/00
2008/0199493 A1 * 8/2008 Picker .................... A61K 39/04 435/320.1
2009/0136546 A1 5/2009 Frazer
2011/0008332 A1 * 1/2011 Brooks ................... A61P 31/12 424/133.1
2014/0099299 A1 * 4/2014 Walter ................. C07K 16/089 435/320.1
2016/0375059 A1 12/2016 Tedder et al.

FOREIGN PATENT DOCUMENTS

EP 905234 A2 * 3/1999 ......... C07K 14/4702
WO WO-2009154995 A2 * 12/2009 .............. A61P 31/04
WO WO-2012135177 A2 * 10/2012 ............. A61K 39/12
WO 2015/117930 A1 8/2015
WO 2019173783 A1 9/2019
WO 2020/037043 A1 2/2020
WO 2020132595 A1 6/2020

OTHER PUBLICATIONS

Stewart, A. and Trinchieri, G. At 17, In-10's Passion Need Not Inflame. Immunity. 2011. 34:460-462. (Year: 2011).*

Kitagawa, T., Iwazawa, T., Robbins, P., Lotze, M., Tahara, H. Advantages and limitations of particle-mediated transfection (gene gun) in cancer immuno-gene therapy using IL-10, IL-12 or B7-1 in murine tumor models. J Gene Med 2003; 5: 958-965. (Year: 2003).*

Niu, G., Heller, R., Catlett-Falcone, R., Coppola, D., Jaroszeski, M., Dalton, W., Jove, R., Yu, H. Gene Therapy with Dominant-negative Stat3 Suppresses Growth of the Murine Melanoma B16 Tumor in Vivo. Cancer Res. 1999. 59:5059-5063 (Year: 1999).*

Yoon, S, Jones, B., Logsdon, N., Harris, B., Kuruganti, S., Walter, M. Epstein-Barr Virus IL-10 Engages IL-10R1 by a Two-step Mechanism Leading to Altered Signaling Properties. Mol Biophys. 2012. 287(32):26586-26595. (Year: 2012).*

Bode. Cancer prevention research—then and now. Nat Rev; 9:508-516. (Year: 2009).*

Umar. Future directions in cancer prevention. Nat Rev; 12:835-848. (Year: 2012).*

Sarfati. Preventing cancer: the only way forward. Lancet; 400:540-541. (Year: 2022).*

(Continued)

*Primary Examiner* — Daniel E Kolker
*Assistant Examiner* — Maureen Varina Driscoll
(74) *Attorney, Agent, or Firm* — Kilpatrick Townsend & Stockton LLP

(57) ABSTRACT

Provided herein are methods for inducing an immune response against an antigen in a subject. In some embodiments, the methods comprise administering a therapeutically effective amount of a vaccine and an interleukin 10 (IL-10) inhibitor to the subject. In some embodiments, the vaccine is an IL-10-deficient vaccine.

18 Claims, 19 Drawing Sheets

Specification includes a Sequence Listing.

(56) References Cited

OTHER PUBLICATIONS

Kaczmarek. Cancer Vaccine Therapeutics: Limitations and Effectiveness—A Literature Review. Cells; 12(2159):1-27. (Year: 2023).*

Nakamura, et al. "IL10-Driven STAT3 Signalling in Senescent Macrophages Promotes Pathological Eye Angiogenesis", Nature Communications, vol. 6, No. 7847, Aug. 11, 2015, pp. 1-14.

Extended European Search Report mailed on Apr. 21, 2022 for EP Application No. 19849102.9, 11 pages.

Brooks et al., "IL-10 Blockade Facilitates DNA Vaccine-Induced T Cell Responses and Enhances Clearance of Persistent Virus Infection", Journal of Experimental Medicine, vol. 205, No. 3, Mar. 17, 2008, pp. 533-541.

Eberhardt et al., "Exploitation of Interleukin-10 (IL-10) Signaling Pathways: Alternate Roles of Viral and Cellular IL-10 in Rhesus Cytomegalovirus Infection", Journal of Virology, vol. 90, No. 21, Nov. 1, 2016, pp. 9920-9930.

Kaufman et al., "Interleukin-10 Enhances the Therapeutic Effectiveness of a Recombinant Poxvirus-based Vaccine in an Experimental Murine Tumor Model", Journal of Immunotherapy, vol. 22, No. 6, Nov. 1, 1999, pp. 489-496.

* cited by examiner

FIG. 3A
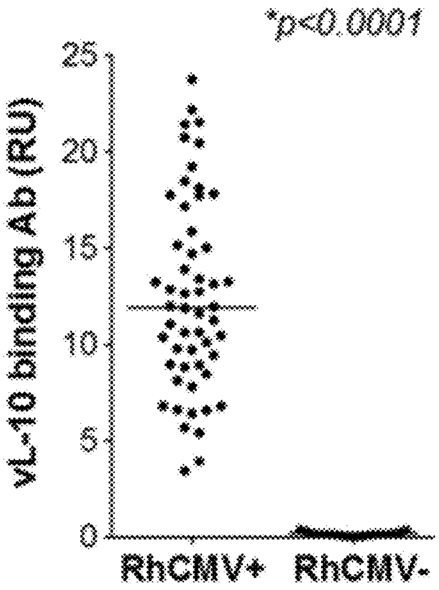
FIG. 3B
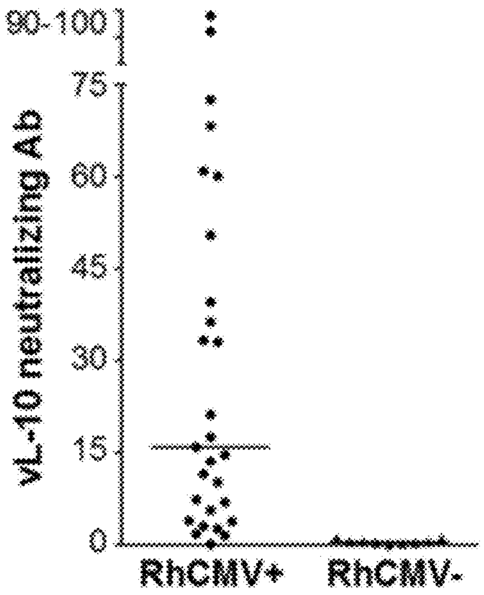
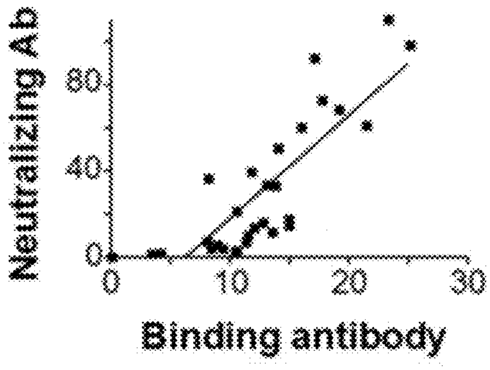
FIG. 3C

FIG. 5A
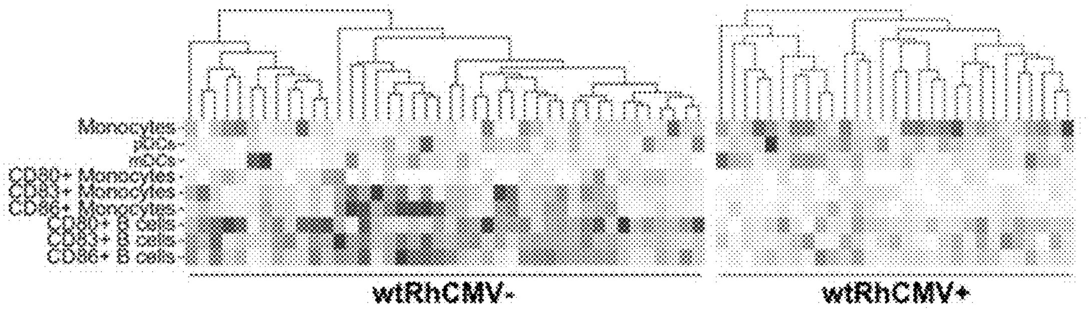
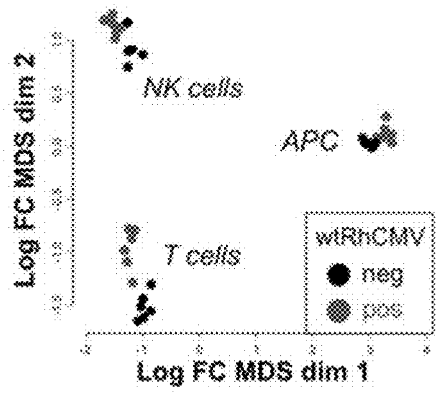
FIG. 5B
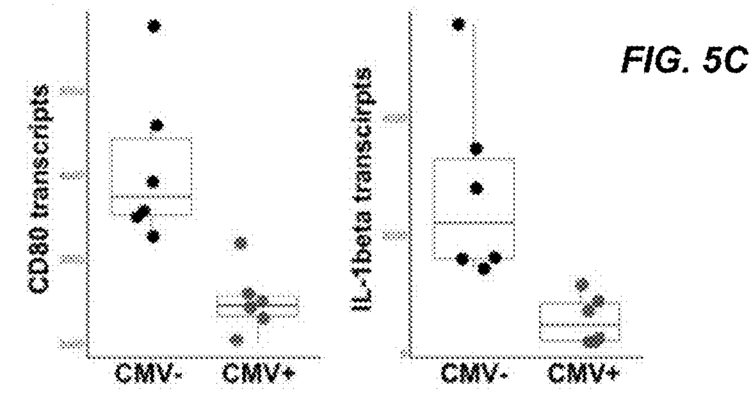
FIG. 5C
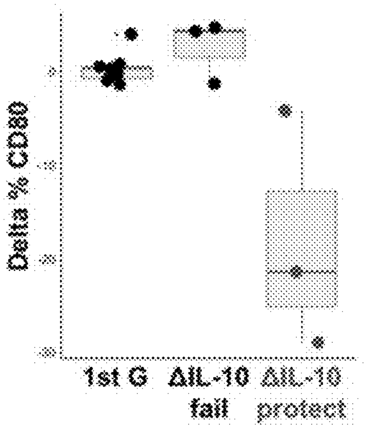
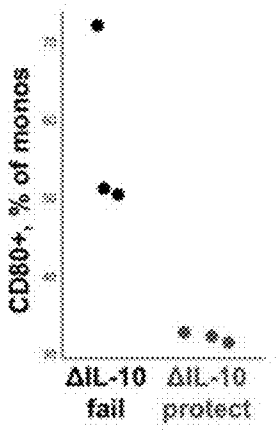
FIG. 5D
FIG. 5E

IL-10 INHIBITION FOR VACCINES AND IMMUNOTHERAPY

CROSS-REFERENCE TO RELATED APPLICATIONS

This application is a continuation application of International Application No. PCT/US2019/046503, filed Aug. 14, 2019, which claims priority to U.S. Provisional Application No. 62/764,848, filed Aug. 15, 2018, and U.S. Provisional Application No. 62/845,671, filed May 9, 2019, the disclosures of which are hereby incorporated by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant No. AI118451, awarded by the National Institutes of Health (NIH). The Government has certain rights in the invention.

SEQUENCE LISTING

This application contains a Sequence Listing which has been submitted electronically in ASCII format and is hereby incorporated by reference in its entirety for all purposes. Said ASCII copy, created on Feb. 10, 2021, is named 070772-226020US-1238459 SL.txt and is 32,738 bytes in size.

BACKGROUND OF THE INVENTION

Rhesus cytomegalovirus (RhCMV)-vectored vaccines were designed to exploit a putative window of vulnerability in early HIV/SIV infection based on their ability to elicit and maintain high frequency, effector-differentiated, broadly targeted virus-specific T cells in potential sites of early viral replication. First-generation RhCMV/SIV vaccines protect ~50% of vaccinated monkeys. While an HIV vaccine with 50% efficacy would be beneficial, a core goal in the field must be to improve this figure, yielding further human health benefit and potentially enabling eradication of HIV. Thus, there is a need for improved vaccines, such as HIV vaccines, and methods to increase vaccine efficacy. Indeed, many vaccine candidates for protection against infectious diseases or cancer do not induce sufficiently robust immune responses, or do not induce them quickly enough for protection against the target condition. In some cases this problem is due to functioning of regulatory immunologic mechanisms such as IL-10 production by the host or by a virus such as cytomegalovirus, which encodes a viral IL-10 protein. The present invention addresses this need, and provides related advantages as well.

BRIEF SUMMARY OF THE INVENTION

In a first aspect, the present invention provides a method for inducing an immune response against an antigen in a subject. In some embodiments, the method comprises administering to the subject a therapeutically effective amount of an interleukin 10 (IL-10) inhibitor and a vaccine. In some embodiments, viral and/or cellular IL-10 are inhibited. In particular embodiments, both viral and cellular IL-10 are inhibited. In some embodiments, STAT3 transducer of IL-10 receptor signaling is inhibited. In particular embodiments, substantially all STAT3 signaling downstream of the IL-10 receptor is inhibited.

In some embodiments, the IL-10 inhibitor comprises a protein, a nucleic acid sequence encoding a protein, a small molecule, or a combination thereof. In some embodiments, the protein comprises an antibody (e.g., an anti-IL-10 antibody, an anti-IL10R antibody, an anti-CD20 antibody, or a combination thereof). In some embodiments, the antibody is anti-IL-10 1F11R1LALA, rituximab, or a combination thereof. In some embodiments, the protein comprises an Fc-IL-10R (e.g., Fc-IL-10R1) fusion protein. In some embodiments, the fusion protein has a high binding affinity (e.g., stronger than about $10^{-6}$ M, $10^{-7}$ M, $10^{-8}$ M, $10^{-9}$ M) for IL-10. In some embodiments, the fusion protein inhibits host and/or viral IL-10. In some embodiments, the fusion protein inhibits binding of all proteins to IL-10R (e.g., IL-10R1). In some embodiments, the fusion protein inhibits IL-10 receptor signaling.

In some embodiments, the protein comprises a portion of an IL-10 protein that comprises one or more mutations that increase affinity of the portion of the IL-10 protein for an IL-10 receptor. In some embodiments, the nucleic acid sequence encodes a protein comprising a portion of an IL-10 protein that comprises one or more mutations that increase affinity of the portion of the IL-10 protein for an IL-10 receptor. In some embodiments, the protein comprises a truncated IL-10 receptor protein. In some embodiments, the nucleic acid sequence encodes a protein comprising a truncated IL-10 receptor protein. In some instances, the truncated IL-10 receptor protein comprises the amino acid sequence set forth in any one of SEQ ID NOS: 5-6. In some embodiments, the protein comprises a truncated protein having IL-10-like activity. In some embodiments, the nucleic acid sequence encodes a protein comprising a truncated protein having IL-10-like activity. In some instances, the truncated protein having IL-10-like activity comprises the amino acid sequence set forth in SEQ ID NO: 7. In some embodiments, the protein comprises a dominant-negative STAT3 protein. In some embodiments, the nucleic acid sequence encodes a protein comprising a dominant-negative STAT3 protein. In some instances, the dominant-negative STAT3 protein comprises the amino acid sequence set forth in any one of SEQ ID NOS: 8-10. In some embodiments, the small molecule comprises AS-101.

In some embodiments, the vaccine comprises a recombinant polynucleotide comprising an adenovirus genome, or a portion thereof, and a nucleic acid sequence encoding the antigen. In some embodiments, the recombinant polynucleotide further comprises a nucleic acid sequence encoding the IL-10 inhibitor.

In some embodiments, the vaccine comprises a recombinant polynucleotide comprising a cytomegalovirus (CMV) genome, or a portion thereof, and a nucleic acid sequence encoding the antigen.

In some embodiments, the vaccine is an IL-10-deficient vaccine. In some embodiments, the IL-10-deficient vaccine comprises a recombinant polynucleotide comprising a cytomegalovirus (CMV) genome, or a portion thereof, and a nucleic acid sequence encoding the antigen, wherein the CMV genome or portion thereof comprises one or more immunomodulatory mutations, wherein the one or more immunomodulatory mutations comprise a mutation within a nucleic acid sequence encoding a protein that has CMV interleukin-10 (CMV IL-10)-like activity. In some embodiments, the one or more immunomodulatory mutations are located in a regulatory region and/or a protein coding region of the nucleic acid sequence encoding the protein that has CMV IL-10-like activity. The CMV can be, for example, a CMV that can infect human, non-human primate, or mouse cells.

In some embodiments, the protein that has CMV IL-10-like activity is human CMV IL-10 (HCMVIL-10) or rhesus macaque CMV IL-10 (RhCMVIL-10). In some embodiments, the nucleotide sequence encoding the antigen is located within the CMV genome or a portion thereof. In some embodiments, the antigen is a non-CMV antigen.

In some embodiments, the one or more immunomodulatory mutations comprise a substitution, a deletion, and/or an insertion of one or more nucleotides. In some embodiments, the mutation within the nucleic acid sequence encoding the protein that has CMV IL-10-like activity comprises a deletion within the first two exons of the nucleic acid sequence encoding the protein that has CMV IL-10-like activity. In some embodiments, the mutation within the nucleic acid sequence encoding the protein that has CMV IL-10-like activity reduces or inactivates the activity of the protein having CMV IL-10-like activity. In some embodiments, the one or more immunomodulatory mutations further comprise an insertion of a nucleic acid sequence encoding an immunostimulatory protein. In some embodiments, the immunostimulatory protein is a cytokine (e.g., IL-12, IL-15, or a combination thereof).

In some embodiments, the CMV is a CMV capable of infecting rhesus macaque cells and the one or more immunomodulatory mutations further comprise a mutation within a region of the CMV genome or portion thereof selected from the group consisting of Rh182, Rh183, Rh184, Rh185, Rh186, Rh187, Rh188, Rh189, and a combination thereof. In some embodiments, the CMV is a CMV capable of infecting human cells and the one or more immunomodulatory mutations further comprise a mutation within a region of the CMV genome or portion thereof selected from the group consisting of US2, US3, US4, US5, US6, US7, US8, US9, US10, US11, and a combination thereof.

In some embodiments, the one or more immunomodulatory mutations further comprise a mutation within a nucleic acid sequence encoding a protein that inhibits antigen presentation by a major histocompatibility complex (MHC) molecule. In some embodiments, the one or more immunomodulatory mutations further comprise a mutation that increases or decreases the unfolded protein response (UPR). In some embodiments, the mutation that increases or decreases the UPR decreases or increases the expression of Human cytomegalovirus UL50, Rhesus cytomegalovirus Rh81, or Mouse cytomegalovirus M50.

In some embodiments, the antigen is an infectious disease antigen (e.g., a bacterial, viral, fungal, protozoal, and/or helminthic infectious disease antigen). In some embodiments, the infectious disease antigen is a viral infectious disease antigen from simian immunodeficiency virus (SIV), human immunodeficiency virus (HIV), hepatitis C virus, herpes simplex virus, Epstein-Barr virus, or a combination thereof. In some embodiments, the infectious disease antigen comprises an HIV or SIV group-specific antigen (gag) protein.

In some embodiments, the antigen is a tumor-associated antigen (e.g., prostate-specific antigen, melanoma-associated antigen 4 (MAGEA4), melanoma-associated antigen 10 (MAGEA10), NY-ESO-1, a neoantigen, or a combination thereof).

In some embodiments, the CMV genome or portion thereof further comprises a mutation that increases tropism or selectivity for a target cell. In some embodiments, the target cell is selected from the group consisting of an antigen-presenting cell (e.g., a dendritic cell), a tumor cell, a fibroblast, an epithelial cell, an endothelial cell, and a combination thereof. In some embodiments, the mutation that increases tropism or selectivity comprises a mutation that modifies a protein, or portion thereof, that is positioned on the outside of the CMV virion. In some embodiments, the mutation that increases tropism or selectivity comprises an insertion of a nucleotide sequence encoding a cellular targeting ligand. In some embodiments, the cellular targeting ligand is selected from the group consisting of an antibody fragment that recognizes a target cell antigen, a ligand that is recognized by a target cell cognate receptor, a viral capsid protein that recognizes a target cell, and a combination thereof. In some embodiments, the cellular targeting ligand is CD154.

In some embodiments, the CMV is a CMV capable of infecting rhesus macaque cells and the mutation that increases tropism or selectivity comprises a mutation within a gene selected from the group consisting of Rh13.1, Rh61/Rh60, Rh157.4, Rh157.5, Rh157.6, and a combination thereof. In some embodiments, the CMV is a CMV capable of infecting human cells and the mutation that increases tropism or selectivity comprises a mutation within a gene selected from the group consisting of RL13, UL36, UL130, UL128, UL131, and a combination thereof.

In some embodiments, the recombinant polynucleotide further comprises a nucleic acid sequence encoding a selectable marker. In some embodiments, the nucleic acid sequence encoding the selectable marker is located within the CMV genome or portion thereof. In some embodiments, the nucleic acid sequence encoding the selectable marker comprises a nucleic acid sequence encoding an antibiotic resistance gene and/or a fluorescent protein.

In some embodiments, the recombinant polynucleotide contains one or more regulatory sequences. In some embodiments, the one or more regulatory sequences control the expression of: (i) a gene or region within the CMV genome or portion thereof, (ii) the antigen-encoding sequence, (iii) an immunostimulatory protein-encoding sequence, (iv) a selectable marker-encoding sequence, (v) a variant thereof, or (vi) a combination thereof. In some embodiments, the one or more regulatory sequences comprise a CMV early enhancer, a chicken beta-actin gene promoter, a first exon of a chicken beta-actin gene, a first intron of a chicken beta-actin gene, a splice acceptor of a rabbit beta-globin gene, an EM7 promoter, an EF1α promoter, or a combination thereof. In some embodiments, the recombinant polynucleotide further comprises a nucleic acid sequence encoding the IL-10 inhibitor. In some embodiments, the IL-10 inhibitor comprises a protein encoded by a nucleic acid sequence (e.g., the IL-10 inhibitor is expressed by a nucleic acid sequence from a virus such as an adenovirus).

In some embodiments, the IL-10 inhibitor is administered before and/or after the vaccine. In some embodiments, the IL-10 inhibitor and the vaccine are administered at about the same time.

In a second aspect, the present invention provides a method for preventing or treating a disease in a subject, the method comprising inducing an immune response against an antigen in the subject according to the methods provided herein (i.e., administering an IL-10 inhibitor and a vaccine to the subject as described herein). In some embodiments, the disease is an infectious disease or cancer.

Other objects, features, and advantages of the present invention will be apparent to one of skill in the art from the following detailed description and figures.

BRIEF DESCRIPTION OF THE DRAWINGS

FIG. 1A shows viral loads in 26 wtRhCMV-seronegative vaccine recipients that demonstrate no instance of stringent viral control, i.e., control to the point that viral genomes are consistently undetectable in peripheral blood (<30 copies/mL). FIG. 1B shows an example of the Mamu-E-restricted T cells observed in vaccine recipients before SIV challenge, sometimes at high level. The cytogram shows T cells that are responsive to Gag69 "supertope," which has been proven to be Mamu-E-restricted. FIG. 1C shows that RhCMV/SIVgag vaccine elicits antibody responses among wtRhCMV-seronegative recipients before SIV challenge. FIGS. 1B and 1C demonstrate that the vaccination regimen produced immune responses, but the viral loads in FIG. 1C demonstrate that these responses were not protective against high viral loads.

FIGS. 3A-3C show that RhCMV-seropositive macaques make vIL-10 binding and neutralizing antibodies, meaning that such macaques contain a natural specific inhibitor of viral IL-10 only. FIG. 3A shows the universal presence of binding antibodies. FIG. 3B shows that viral IL-10 neutralizing activity is highly variable. The ordinate shows percentage IL-12 secretion restored in a bioassay. FIG. 3C shows that viral IL-10 binding and neutralizing titers are correlated.

FIG. 4A shows CD4+ T cell responses to RhCMV immediate early protein-1 (peptide pool). All responses in this panel are TNF-alpha responses. FIG. 4B shows that CD4+ T cell responses to SIV Gag peptide pool induced by RhCMVdIL10/gag (labeled "ΔIL-10") are superior to those induced by RhCMV/gag (labeled "1$^{st}$ G").

FIGS. 5A-5E show that RhCMVdIL10 but not first-generation vectors provoke CD80 down regulation in wtRhCMV-negative vaccine recipients. FIG. 5A shows the intensity of immunophenotype (listed along the left edge of the heat map) among wtRhCMV− (left) vs. wtRhCMV+ macaques (right). Note the increased frequency of CD14+ monocytes and reduced CD80 expression in PBMCs of RhCMV+. FIG. 5B shows that transcriptomic analysis demonstrates clear separation of T cells, NK cells, and APCs from wtRhCMV-vs. wtRhCMV+ macaques. FIG. 5C shows that CD80 down regulation is apparent in the transcriptomics of wtRhCMV+ macaques (right). This down regulation mirrors the "protective signature" of RhCMV/SIV vaccination. FIG. 5D shows that first generation vectors do not down regulate CD80 significantly when administered to wtRhCMV-seronegative recipients. Viral IL-10-deficient vectors do achieve such down regulation sometimes—and those macaques manifesting down regulation are those that were protected from SIV (FIG. 2). FIG. 5E shows that the absolute level of CD80 expression (percentage of CD80+ monocytes) is low at SIV challenge, in those animals that turn out to be protected.

FIG. 6A shows IL-10 activity, measured by suppression of IL-12 secretion in a bioassay, in blood two weeks after priming vaccination with first-generation RhCMV/SIVgag (CMV-seropositive recipients), RhCMV/SIVgag (CMV-seronegative recipients), or viral IL-10-deleted RhCMV/dIL10/SIVgag. First-generation vaccines carrying viral IL-10 elicit more overall host IL-10 activity in wtRhCMV-seronegative recipients (middle column). IL-10 activity is expressed as inverse IL-12 secretion in a bioassay. Furthermore, using macaques treated with anti-IL10 neutralizing antibody or with an adenovirus expressing host IL-10, we identified IP-10 as a significant inverse correlate of IL-10 activity, with less IP-10 in the presence of greater IL-10 activity. FIG. 6B shows that RhCMVdIL10/SIVgag vaccination is accompanied by greater circulating IP-10, suggesting less overall IL-10 production.

FIG. 14A shows that Ad26/SIVgag and Ad26/SIVgag-IRES-dnIL-10R express SIV Gag protein under control of the human EFla promoter and its endogenous first intron. Ad26/SIVgag-IRES-dnIL-10R additionally contains a truncated IL-10Ra coding sequence, lacking the intracellular domain that is required for signaling. FIG. 14B shows that the vectors express immunoreactive SIV Gag protein, as demonstrated by the presence of an SIV Gag band after transduction of 293 cells with Ad26/SIVgag-IRES-dnIL-10R. FIG. 14C shows that the dominant-negative IL-10R in Ad26/SIVgag-IRES-dnIL-10R is expressed on the surface of transduced HEK 293 cells. Cells transduced by a control Ad26 vector (left) demonstrate a minimal increase in fluorescence upon addition of anti-IL-10R1 antibody (compare gray histogram for no antibody control to black histogram); cells transduced by Ad26/SIVgag-IRES-dnIL-10R (right) demonstrate intense staining with anti-IL-10R1 antibody (black histogram). FIG. 14D shows that dominant-negative IL-10R is functionally inhibitory. PBMCs that are infected with Ad26 in the presence of IL-10 signaling produce minimal IL-12 in response (gray bars); however, expression of dominant-negative IL-10R inhibits the IL-10 signal and permits greater IL-12 expression (black bars). FIG. 14E shows that Ad26/SIVgag-IRES-dnIL-10R vaccine provokes an immune response to the immunoreactive Gag gene in vivo, leading to functional anti-Gag $CD4^+$ T cells expressing both IFN-gamma and TNF-alpha. The left cytogram in this panel shows the result of a negative-control stimulation with DMSO only; the right panel demonstrates the responding $CD4^+$ T cells seen after stimulation with overlapping Gag peptides. FIG. 14F shows that immune responses to Ad26/SIVgag-IRES-dnIL-10R vaccination (black traces) are maintained for at least eight weeks after vaccination.

DETAILED DESCRIPTION OF THE INVENTION

I. Introduction

Figures 1A, 1B, 1C:
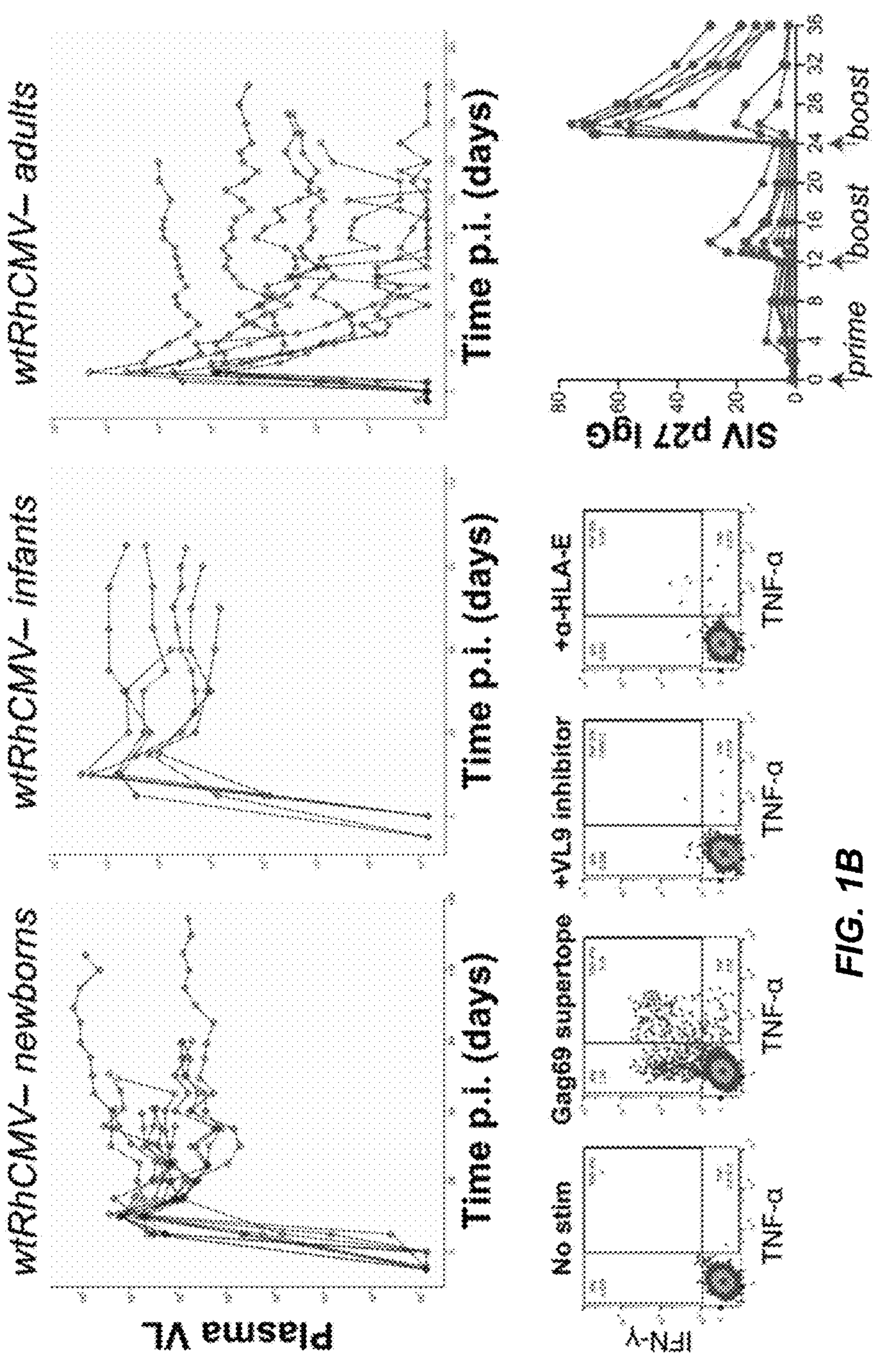
FIGS. 1A-1C show that RhCMV/SIV vaccines having an intact viral IL-10 gene are not reliably effective in wtRhCMV-seronegative recipients.

The present invention relates to providing inhibitors of IL-10 signaling concomitantly with a vaccine or other immunostimulus, so that responses to vaccination occur in the absence of such signaling, and is based, in part, on the surprising discovery that second-generation RhCMV/SIV vaccines lacking the viral IL-10 gene (RhCMVdIL10/SIV) protect non-human primate infants that have no prior RhCMV immunity, while first-generation (IL-10-intact) RhCMV/SIV vaccines do not. Furthermore, first-generation vaccines have been proven effective only in wild-type (wt) RhCMV-seropositive macaques having neutralizing antibodies to viral IL-10 generated in response to prior wtRhCMV infection. The present invention is also based, in part, on the discovery that inhibiting viral IL-10 and/or host (i.e., cellular) IL-10 can increase vaccine efficacy.

II. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" as used herein shall generally mean an acceptable degree of error for the quantity measured given the nature or precision of the measurements. Typically, exemplary degrees of error are within 20 percent (%), preferably within 10%, and more preferably within 5% of a given value or range of values. Any reference to "about X" specifically indicates at least the values X, 0.8X, 0.81X, 0.82X, 0.83X, 0.84X, 0.85X, 0.86X, 0.87X, 0.88X, 0.89X, 0.9X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, 1.1X, 1.11X, 1.12X, 1.13X, 1.14X, 1.15X, 1.16X, 1.17X, 1.18X, 1.19X, and 1.2X. Thus, "about X" is intended to teach and provide written description support for a claim limitation of, e.g., "0.98X."

The term "interleukin 10 inhibitor" or "IL-10 inhibitor" refers to a compound or drug, or a prodrug thereof, that decreases the function or activity of a protein that has IL-10-like activity (e.g., IL-10) and/or decreases IL-10 signaling. In some embodiments, an IL-10 inhibitor decreases expression (e.g., transcription or translation) of a protein that has IL-10-like activity. In some embodiments, an IL-10 inhibitor decreases expression of an IL-10 receptor protein. In some embodiments, an IL-10 inhibitor inhibits binding between a protein that has IL-10-like activity and an IL-10 receptor protein. In some embodiments, an IL-10 inhibitor decreases the function, activity, or expression of a downstream component of the IL-10 signaling pathway. As a non-limiting example, an IL-10 inhibitor can inhibit downstream STAT3 signaling. A "small molecule IL-10 inhibitor" refers to an IL-10 inhibitor that is a small molecule (i.e., having a low molecular weight, e.g., less than about 900 daltons).

The terms "viral interleukin 10," "viral IL-10," and "vIL-10" refer to a protein having IL-10-like activity that is encoded by or expressed from a nucleic acid sequence that is endogenous to a viral genome or portion thereof. In some embodiments, the term refers to a protein having IL-10-like activity that is encoded by or expressed from a nucleic acid sequence that is endogenous to a viral expression vector, such as one that is used as part of a vaccine (e.g., a vaccine that comprises a CMV-based expression vector).

The terms "cellular interleukin 10," "cellular IL-10," "host interleukin 10," "host IL-10," and "cIL-10" refer to a protein having IL-10-like activity that is expressed by a cell that is located within, or isolated or derived from, a host or subject who is the recipient of an IL-10 inhibitor and a vaccine according to methods of the present invention. The terms include proteins having IL-10-like activity that are endogenously expressed by the cell (e.g., host cell), as well as non-viral proteins having IL-10-like activity that are recombinantly expressed by the cell. The terms also refer to an endogenous or non-viral protein having IL-10-like activity that is circulating (e.g., in the blood or other body fluid) within the host or subject.

The term "cytomegalovirus" or "CMV" refers to viruses that include members of the *Cytomegalovirus* genus of viruses (within the order Herpesvirales, family Herpesviridae, subfamily Betaherpesvirinae). The term includes, but is not limited to, Human cytomegalovirus (HCMV; also known as Human herpesvirus 5 (HHV-5)), Simian cytomegalovirus (SCCMV or AGMCMV), Baboon cytomegalovirus (BaCMV), Owl monkey cytomegalovirus (OMCMV), Squirrel monkey cytomegalovirus (SMCMV), and Rhesus cytomegalovirus (RhCMV) that infects macaques.

The term "protein that has interleukin-10-like activity" or "protein that has IL-10-like activity" refers to any protein that functions in a similar way to interleukin-10 (IL-10) or produces a similar effect (e.g., has a similar immunomodulatory effect) to IL-10. The term includes, but is not limited to, proteins encoded by viral IL-10 genes (e.g., CMV IL-10 genes) such as HCMVIL-10 in HCMV and RhCMVIL-10 in RhCMV, proteins that bind to an IL-10 receptor, proteins that stimulate downstream IL-10 receptor signaling, and functional portions thereof. The term also includes, but is not limited to, proteins encoded by corresponding viral IL-10 genes in SCCMV/AGMCMV, BaCMV, OMCMV, and SMCMV, as well as homologs thereof. A protein that has IL-10-like activity can, for example, downregulate the expression of Th1 and macrophage cytokines (e.g., interferon-gamma, IL-1-beta, IL-2, IL-6, IL-12, TNF-alpha, and GM-CSF), MHC class II antigens, and/or macrophage co-stimulatory molecules, promote blockade of NF-κB activity, and/or enhance B cell survival, proliferation, and/or antibody production.

The term "cytokine" refers to a broad category of small proteins, typically between about 5 kDa and about 20 kDa in size, that are typically secreted and that function in cell signaling, typically by binding to cellular receptors that transmit signals to the intracellular environment of target cells. Cytokines include interleukins, chemokines, interferons, lymphokines, monokines, and tumor necrosis factors. Cytokines are produced by immune cells (e.g., monocytes, macrophages, B lymphocytes, T lymphocytes, and mast cells), endothelial cells, fibroblasts, and stromal cells. Cytokines play diverse roles in immune responses, inflammation, and responses to infection, trauma, and sepsis, as well as cancer. In the context of immune function, cytokines regulate, among other things, the balance between humoral immunity and cell-based immunity, as well as the balance between different types of cell-based immunity, e.g., Th1-versus Th2-predominant cell-based immunity. Cytokines also regulate the maturation and growth of immune cells. Cytokines can either increase or decrease an immune response, depending on the particular cytokine.

The term "interleukin" refers to a group of cytokines that play important roles in innate and adaptive immune system function. For example, some interleukins promote the development and differentiation of B lymphocytes, T lymphocytes, and hematopoietic cells. Most interleukins are produced by helper CD4 T lymphocytes, monocytes, macrophages, and endothelial cells. Interleukins can either enhance or inhibit immune function, depending on the particular interleukin.

Examples of interleukins (ILs) include IL-1 (which targets T helper cells, B cells, natural killer (NK) cells, macrophages, and endothelial cells, among others), IL-2 (which targets activated T cells and B cells, regulatory T cells, NK cells, macrophages, and oligodendrocytes), IL-3 (which targets hematopoietic stem cells and mast cells), IL-4 (which targets activated B cells, T cells, and endothelial cells), IL-5 (which targets B cells and eosinophils), IL-6 (which targets activated B cells, plasma cells, hematopoietic cells, and T cells, among others), IL-7 (which targets pre/pro-B and pre/pro-T cells, as well as NK cells), IL-8 (also known as CXCL8, which targets neutrophils, basophils, and lymphocytes), IL-9 (which targets T cells and B cells), IL-10 (which targets macrophages, B cells, mast cells, Th1 cells, and Th2 cells), IL-11 (which targets bone marrow stromal cells), IL-12 (which targets activated T cells and NK cells), IL-13 (which targets Th2 cells, B cells, and macrophages), IL-14 (which targets activated B cells), IL-15 (which targets T cells and activated B cells), IL-16 (which targets CD4+ T cells), IL-17 (which targets epithelial and endothelial cells, among others), IL-18 (which targets Th1 cells and NK cells), IL-19, IL-20, IL-21 (which targets dendritic cells and all lymphocytes), IL-22, IL-23, IL-24, IL-25, IL-26, IL-27, IL-28, IL-29, IL-30, IL-31, IL-32, IL-33, IL-34, IL-35, and IL-36.

"Interleukin-4" or "IL-4" induces differentiation of native helper T cells (Th0 cells) to Th2 cells. Subsequently, upon activation by IL-4, Th2 cells produce additional IL-4 in a positive feedback loop. IL-4 also functions to stimulate proliferation of activated B and T cells, differentiation of B cells into plasma cells, induction of B cell class switching to IgE, and upregulation of MHC class II production. IL-4 also decreases the production of Th1 cells, macrophages, interferon-gamma, and dendritic cell IL-12. Non-limiting examples of human IL-4 amino acid sequences are set forth under NCBI Reference Sequence numbers NP_000580, NP_758858, and NP_001341919.

"Interleukin-5" or "IL-5" is produced by Th2 cells and mast cells, and functions to stimulate B cell growth and increase immunoglobulin secretion. IL-5 is also an important mediator of eosinophil activation. A non-limiting example of a human IL-5 amino acid sequence is set forth under NCBI Reference Sequence number NP_000870.

"Interleukin-6" or "IL-6" is produced by macrophages, Th2 cells, B cells, astrocytes, and endothelial cells. IL-6 acts as a pro-inflammatory cytokine (e.g., in response to infection or tissue damage arising, e.g., from trauma or burns), although it can also act as an anti-inflammatory myokine. Non-limiting examples of human IL-6 amino acid sequences are set forth under NCBI Reference Sequence numbers NP_000591 and NP 001305024.

"Interleukin-10" or "IL-10" is an anti-inflammatory cytokine that is encoded by the IL10 gene in humans. IL-10, which is a homodimer having subunits that are each 178 amino acids in length, binds to a receptor complex that consists of two IL-10 receptor-1 proteins and two IL-10 receptor-2 proteins. Binding of IL-10 to the receptor complex induces STAT3 signaling, via JAK1 phosphorylation of the cytoplasmic tails of IL-10 receptor-1 and Tyk2 phosphorylation of the cytoplasmic tails of IL-10 receptor-2. IL-10 is produced by subsets of monocytes, Th2 cells, $CD8^+$ T cells, mast cells, macrophages, and B cells. IL-10 has multiple effects, including but not limited to, downregulation of the expression of Th1 and macrophage cytokines (e.g., interferon-gamma, IL-1-beta, IL-2, IL-6, IL-12, TNF-alpha, and GM-CSF), MHC class II antigens, and/or macrophage co-stimulatory molecules; blockade of NF-κB activity; and/or enhancement of B cell survival, proliferation, and/or antibody production. A non-limiting example of a human IL-10 amino acid sequence is set forth under NCBI Reference Sequence number NP_000563 and SEQ ID NO:2. A non-limiting example of a rhesus macaque IL-10 amino acid sequence is set forth under SEQ ID NO:1.

Many pathogens, including CMV, exploit the IL-10 pathway to enhance pathogen persistence. For example, many CMVs encode their own IL-10 (e.g., HCMVIL-10, also known as UL111, for HCMV and RhCMVIL-10, also known as Rh143, for RhCMV). These viral IL-10 proteins have different amino acid sequences from the human IL-10 protein, but are nonetheless capable of binding IL-10 receptors. Thus, CMV-infected cells will produce viral IL-10, which in turn inhibits the immune response against CMV infection and enhances CMV persistence within the host.

"Interleukin-12" or "IL-12" is produced by dendritic cells, macrophages, neutrophils, and B-lymphoblastoid cells in response to antigenic stimulation. IL-12 is involved in the differentiation of naïve T cells into Th1 cells, and also plays a role in the enhancement of the cytotoxic activity of NK cells and $CD8^+$ T cells.

"Interleukin-15" or "IL-15" is secreted by mononuclear phagocytes, among other cells, in response to viral infection and induces the proliferation of NK cells, an important function of which is to kill virally infected cells. Non-limiting examples of human IL-15 amino acid sequences are set forth under NCBI Reference Sequence numbers NP_000576 and NP_751915.

The term "tumor necrosis factor-alpha" or "TNF-alpha" refers to the cytokine that is encoded by the TNFA gene in humans. TNF-alpha is produced by activated macrophages, $CD4^+$ T cells, NK cells, neutrophils, eosinophils, mast cells, and neurons. TNF-alpha is involved in processes such as the induction of fever, apoptosis, cachexia, and inflammation, as well as the inhibition of tumorigenesis and viral replication. TNF-alpha also functions in promoting responses to sepsis. A non-limiting example of a human TNF-alpha amino acid sequence is set forth under NCBI Reference Sequence number NP_000585.

The term "C-reactive protein" or "CRP" refers to a pentameric ring-shaped protein that is encoded by the CRP gene and is a member of the pentraxin family of proteins. CRP is synthesized by the liver and the levels of the protein increase in response to IL-6 secretion by macrophages and T cells. CRP binds to phosphocholine that is present on the surface of dead or dying cells, as well as some bacteria, thus activating the complement system and promoting phagocytosis by macrophages. Non-limiting examples of human CRP amino acid sequences are set forth under NCBI Reference Sequence numbers NP_000558, NP_001315986, and NP_001315987.

The term "interferon-gamma" or "IFN-γ" refers to a cytokine that is a member of the type II class of interferons and is encoded by the IFNG gene. IFN-γ plays important roles in innate and adaptive immunity against viral, bacterial, and protozoal infections. In particular, IFN-γ is a macrophage activator and induces expression of class II MHC molecules. IFN-γ is produced by natural killer cells, natural killer T cells, $CD4^+$ Th1 cells, $CD8^+$ cytotoxic T lymphocyte cells, and non-cytotoxic innate lymphoid cells. A non-limiting example of a human IFN-γ amino acid sequence is set forth under NCBI Reference Sequence number NP 000610.

The term "immunomodulatory mutation" refers to any mutation that increases or decreases the magnitude, character, and/or effectiveness of an immune response in a host cell or organism (e.g., a subject in whom an immune response against an antigen is being induced). The term includes mutations that increase the expression and/or activity of proteins involved in modulating the immune response in a host cell or organism. As a non-limiting example, an immunomodulatory mutation can increase or decrease the expression and/or activity of a cytokine (e.g., an interleukin, chemokine, interferon, lymphokine, and/or tumor necrosis factor). In some instances, an immunomodulatory mutation decreases or abolishes the function of a protein that inhibits immune function (e.g., IL-10). In other instances, an immunomodulatory mutation increases the expression or activity of an immunostimulatory protein (e.g., IL-12 or IL-15). As another non-limiting example, an immunomodulatory mutation can decrease or increase the function of a protein that is associated with antigen presentation or immune surveillance. In some instances, an immunomodulatory mutation decreases virus-mediated inhibition of major histocompatibility complex (MHC)-associated antigen presentation. As a further non-limiting example, an immunomodulatory mutation can increase or decrease the expression and/or activity of a protein that is involved in modulating the unfolded protein response (UPR). The term includes insertions, deletions, and/or substitutions of one or more nucleotides, including insertions of one or more partial or entire gene sequences, as well as deletions of partial or entire gene sequences.

The term "antigen" refers to a molecule that is capable of inducing an immune response (e.g., in a subject). While in many instances an immune response involves the production of an antibody that targets or specifically binds to the antigen, as used herein an antigen also refers to molecules that induce immune responses other than those that specifically involve the production of an antibody that targets the antigen, e.g., a cell-mediated immune response involving expansion of T cells that target antigen-derived peptides presented on the surface of target cells. The antigen can originate from a foreign organism, such as a virus or microbe (e.g., bacterial organism), or can originate from a foreign tissue. Alternatively, the antigen can originate from within a subject (i.e., a subject in which the antigen induces an immune response). As a non-limiting example, an antigen can originate from a cell in a subject that has been injured, has been infected with a pathogen (e.g. a virus or microbe such as a bacterial organism), or is aberrant or damaged (e.g., a cancer cell). The term also refers to molecules that do not necessarily induce immune responses by themselves.

The term "antigen-presenting cell" or "APC" refers to a cell that displays or presents an antigen, or a portion thereof, on the surface of the cell. Typically, antigens are displayed or presented with a major histocompatibility complex (MHC) molecule. Almost all cell types can serve as APCs, and APCs are found in a large number of different tissue types. Professional APCs, such as dendritic cells, macrophages, and B cells, present antigens to T cells in a context that most efficiently leads to the T cells' activation and subsequent proliferation. Many cell types present antigens to cytotoxic T cells.

The term "infectious disease" refers to any disease or disorder caused by an organism, (e.g., viruses, bacteria, fungi, protozoa, helminths, and parasitic organisms). The term includes diseases and disorders that are transmitted from one subject to another (e.g., human to human, non-human animal to human, and human to non-human animal), as well as those caused by ingesting contaminated food or water or by exposure to pathogenic organisms (e.g., in the environment).

An "infectious disease antigen" refers to any molecule originating from an infectious disease-causing organism that can induce an immune response (e.g., in a subject). For example, an infectious disease antigen can originate from a virus, bacterium, fungus, protozoan, helminth, or parasite, and can be, for example, a bacterial wall protein, a viral capsid or structural protein (e.g., a retroviral group-specific antigen (gag) protein, such as an HIV or SIV gag protein), or a portion thereof.

The term "cancer" refers to any of various malignant neoplasms characterized by the proliferation of anaplastic cells that tend to invade surrounding tissue and metastasize to new body sites. Non-limiting examples of different types of cancer suitable for treatment using the methods and compositions of the present invention include colorectal cancer, colon cancer, anal cancer, liver cancer, ovarian cancer, breast cancer, lung cancer, bladder cancer, thyroid cancer, pleural cancer, pancreatic cancer, cervical cancer, prostate cancer, testicular cancer, bile duct cancer, gastrointestinal carcinoid tumors, esophageal cancer, gall bladder cancer, rectal cancer, appendix cancer, small intestine cancer, stomach (gastric) cancer, renal cancer (e.g., renal cell carcinoma), cancer of the central nervous system, skin cancer, oral squamous cell carcinoma, choriocarcinomas, head and neck cancers, bone cancer, osteogenic sarcomas, fibrosarcoma, neuroblastoma, glioma, melanoma, leukemia (e.g., acute lymphocytic leukemia, chronic lymphocytic leukemia, acute myelogenous leukemia, chronic myelogenous leukemia, or hairy cell leukemia), lymphoma (e.g., non-Hodgkin's lymphoma, Hodgkin's lymphoma, B-cell lymphoma, or Burkitt's lymphoma), and multiple myeloma.

The term "tumor-associated antigen" or "TAA" refers to any antigen that is produced by a tumor cell (i.e., any protein or molecule produced by a tumor cell that can induce an immune response, e.g., in a subject). TAAs include, but are not limited to, products of mutated oncogenes and mutated tumor suppressor genes, overexpressed or aberrantly expressed cellular proteins, antigens that are produced by oncogenic viruses, oncofetal antigens, altered cell surface glycolipids and glycoproteins, and antigens that are cell type-specific.

Non-limiting examples of TAAs include the melanoma-associated antigens (MAGEs). MAGE proteins contain a conserved domain that is about 200 amino acids in length and is usually located near the C-terminal end of the protein, although the conserved domain is located closer to the central portion of some MAGE proteins. Human MAGE proteins include MAGEA1, MAGEA2, MAGEA2B, MAGEA3, MAGEA4, MAGEA5, MAGEA6, MAGEA7P, MAGEA8, MAGEA9, MAGEA9B, MAGEA10, MAGEA11, MAGEA12, MAGEA13P, MAGEB1, MAGEB2, MAGEB3, MAGEB4, MAGEB5, MAGEB6, MAGEB10, MAGEB16, MAGEB17, MAGEB18, MAGEC1, MAGEC2, MAGEC3, MAGED1, MAGED2, MAGED3 (also known as "trophin" or "TRO"), MAGED4, MAGED4B, MAGEE1, MAGEE2, MAGEF1, MAGEEG1 (also known as "NSMCE3"), MAGEH1, MAGEL2, and NDN.

The protein "melanoma-associated antigen 4" or "MAGEA4" is encoded by the MAGEA4 gene in humans, located at chromosomal location Xq28. Non-limiting examples of human MAGEA4 amino acid sequences are set forth under NCBI Reference Sequence numbers NP_001011548, NP_001011549, NP_001011550, and NP_002353.

The protein "melanoma-associated antigen 10" or "MAGEA10" is encoded by the MAGEA10 gene in humans, located at chromosomal location Xq28. Non-limiting examples of human MAGEA10 amino acid sequences are set forth under NCBI Reference Sequence numbers NP_001011543, NP_001238757, and NP_066386.

The term "prostate-specific antigen" or "PSA" refers to a glycoprotein encoded by the KLK3 gene in humans, and is also known as "gamma-seminoprotein" and "kallikrein-3." PSA is present in small quantities in the serum of men with normal prostates, but is often elevated in the presence of prostate cancer or other disorders of the prostate. Non-limiting examples of human PSA amino acid sequences are set forth under NCBI Reference Sequence numbers NP_001025218, NP_001025219, NP_001639.

The term "NY-ESO-1" refers to the cancer/testis family tumor antigen that is also known as "cancer/testis antigen 1" and is encoded by the CTAG1B gene in humans. NY-ESO-1 is highly expressed in many poor-prognosis melanomas. A non-limiting example of a human NY-ESO-1 amino acid sequence is set forth under NCBI Reference Sequence number NP_001318.1.

The term "major histocompatibility complex" or "MHC" refers to a group of cell surface proteins that are essential for recognition of foreign molecules by the adaptive immune system. The primary function of MHC molecules is to bind to antigens or antigen-derived peptides that are derived from pathogens and subsequently display the antigens on the surfaces of cells in order to facilitate recognition by T cells. MHC molecules also participate in interactions between leukocytes and other leukocytes, as well as between leukocytes and other cell types within the body. In humans, the MHC is also known as the "human leukocyte antigen complex" or "HLA complex."

Class I MHC molecules, which predominantly present peptides from inside the cell, are encoded by the HLA-A, HLA-B, HLA-C, HLA-E, HLA-F, and HLA-G genes. HLA-A, HLA-B, and HLA-C genes are more polymorphic, while HLA-E, HLA-F, and HLA-G genes are less polymorphic. HLA-K and HLA-L are also known to exist as pseudogenes. In addition, beta-2-microglobulin is an MHC class I protein, encoded by the B2M gene. Non-limiting examples of HLA-A nucleotide sequences are set forth under NCBI Reference Sequence numbers NM_001242758 and NM_002116. A non-limiting example of an HLA-B nucleotide sequence is set forth under NCBI Reference Sequence number NM_005514. Non-limiting examples of HLA-C nucleotide sequences are set forth under NCBI Reference Sequence numbers NM_001243042 and NM_002117. A non-limiting example of an HLA-E nucleotide sequence is set forth under NCBI Reference Sequence number NM_005516. A non-limiting example of an HLA-F nucleotide sequence is set forth under NCBI Reference Sequence number NM_018950. A non-limiting example of an HLA-G nucleotide sequence is set forth under NCBI Reference Sequence number NM_002127. A non-limiting example of a B2M nucleotide sequence is set forth under NCBI Reference Sequence number NM_004048.

Class II MHC molecules, which predominantly present antigens from the outside of the cell to T lymphocytes, are encoded by the HLA-DP, HLA-DM, HLA-DO, HLA-DQ, and HLA-DR genes. HLA-DM genes include HLA-DMA and HLA-DMB. HLA-DO genes include HLA-DOA and HLA-DOB. HLA-DP genes include HLA-DPA1 and HLA-DPB1. HLA-DQ genes include HLA-DQA1, HLA-DQA2, HLA-DQB1, and HLA-DQB2. HLA-DR genes include HLA-DRA, HLA-DRB1, HLA-DRB3, HLA-DRB4, and HLA-DRB5. Non-limiting examples of HLA-DMA and HLA-DMB nucleotide sequences are set forth under NCBI Reference Sequence numbers NM_006120 and NM_002118, respectively. Non-limiting examples of HLA-DRA, HLA-DRB1, HLA-DRB3, HLA-DRB4, and HLA-DRB5 nucleotide sequences are set forth in NCBI Reference Sequence numbers NM_01911, NM_002124, NM_022555, NM_021983, NM_002125, respectively.

As used herein, the term "tropism" refers to the ability of a composition of the present invention (e.g., a recombinant polynucleotide of the present invention or a viral particle comprising or encoded by a recombinant polynucleotide of the present invention) to enter, infect, or replicate in a particular cell or tissue type (e.g., a target cell or tissue type found in a subject in whom an immune response against an antigen is being induced). As non-limiting examples, tropism can be broad (i.e., a recombinant polynucleotide of the present invention can enter a large number of different cell or tissue types, or a virus comprising or encoded by a recombinant polynucleotide of the present invention can infect or replicate in a large number of different cell or tissue types) or can be narrow (i.e., a recombinant polynucleotide of the present invention can enter only a small number of different cell or tissue types, or a virus comprising or encoded by a recombinant polynucleotide of the present invention can infect or replicate in only a small number of different cell or tissue types). Furthermore, as described further herein, recombinant polynucleotides of the present invention can be modified such that they possess tropism for specific desired cell or tissue type(s) (i.e., a recombinant polynucleotide can enter specific desired cell or tissue type(s), or a viral particle comprising or encoded by a recombinant polynucleotide of the present invention can enter specific desired cell or tissue type(s)). In some instances, tropism for a specific cell or tissue type is increased or imparted by the addition of a nucleic acid sequence that encodes a cellular targeting ligand.

The term "cellular targeting ligand" refers to any protein, molecule, or portion thereof that increases the ability of a composition of the present invention to enter, infect, or replicate in a specific cell or tissue type. As a non-limiting example, a cellular targeting ligand can increase the ability of a composition of the present invention (e.g., a recombinant polynucleotide of the present invention, or a viral particle comprising or encoded by a recombinant polynucleotide of the present invention) to be recognized by a specific target cell or tissue type, or to recognize a specific target cell or tissue type. Cellular targeting ligands include, but are not limited to, antibody fragments that recognize a target cell antigen, ligands that are recognized by a target cell cognate receptor, and viral capsid proteins that recognize a target cell.

As used herein, the terms "polynucleotide," "nucleic acid," and "nucleotide," refer to deoxyribonucleic acids (DNA) or ribonucleic acids (RNA) and polymers thereof. The term includes, but is not limited to, single-, double-, or multi-stranded DNA or RNA, genomic DNA, cDNA, and DNA-RNA hybrids, as well as other polymers comprising purine and/or pyrimidine bases or other natural, chemically modified, biochemically modified, non-natural, synthetic, or derivatized nucleotide bases. Unless specifically limited, the term encompasses nucleic acids containing known analogs of natural nucleotides that have similar binding properties as the reference nucleic acid. Unless otherwise indicated, a particular nucleic acid sequence also implicitly encompasses conservatively modified variants thereof (e.g., degenerate codon substitutions), homologs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

The term "nucleotide sequence encoding a peptide" refers to a segment of DNA, which in some embodiments may be a gene or a portion thereof, involved in producing a peptide chain. A gene will generally include regions preceding and following the coding region (leader and trailer) involved in the transcription/translation of the gene product and the regulation of the transcription/translation. A gene can also include intervening sequences (introns) between individual coding segments (exons). Leaders, trailers, and introns can include regulatory elements that are necessary during the transcription and the translation of a gene (e.g., promoters, terminators, translational regulatory sequences such as ribosome binding sites and internal ribosome entry sites, enhancers, silencers, insulators, boundary elements, replication origins, matrix attachment sites and locus control regions, etc.). A "gene product" can refer to either the mRNA or protein expressed from a particular gene.

The terms "expression" and "expressed" in the context of a gene refer to the transcriptional and/or translational product of the gene. The level of expression of a DNA molecule in a cell may be assessed on the basis of either the amount of corresponding mRNA that is present within the cell or the amount of protein encoded by that DNA produced by the cell.

The term "recombinant" when used with reference, e.g., to a polynucleotide, protein, vector, or cell, indicates that the polynucleotide, protein, vector, or cell has been modified by the introduction of a heterologous nucleic acid or protein or the alteration of a native nucleic acid or protein, or that the cell is derived from a cell so modified. For example, recombinant polynucleotides contain nucleic acid sequences that are not found within the native (non-recombinant) form of the polynucleotide.

The terms "vector" and "expression vector" refer to a polynucleotide construct, generated recombinantly or synthetically, with a series of specified nucleic acid elements that permit transcription of a particular nucleic acid sequence (e.g., within a viral (e.g. CMV) genome or a portion thereof) in a host cell. As used herein, the term "CMV vector" or "CMV-based vector" refers to a vector that is derived from or comprises a polynucleotide (e.g., recombinant polynucleotide) comprising a CMV genome or a portion thereof. Typically, a vector includes a nucleic acid sequence to be transcribed, operably linked to a promoter. Other elements that may be present in a vector include those that enhance transcription (e.g., enhancers) and terminate transcription (e.g., terminators), those that confer certain binding affinity or antigenicity to a protein (e.g., recombinant protein) produced from the vector, and those that enable replication of the vector and its packaging into a viral particle (e.g., a CMV particle). Recombinant polynucleotides used in methods of the present invention that are virus-based vectors (e.g., CMV-based vectors) can be used as viral vaccine vectors.

The terms "polypeptide," "peptide," and "protein" are used interchangeably herein to refer to a polymer of amino acid residues. All three terms apply to amino acid polymers in which one or more amino acid residues are an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The terms "subject," "individual," and "patient" are used interchangeably herein to refer to a vertebrate, preferably a mammal, more preferably a human. Mammals include, but are not limited to, murines, mice, rats, simians, humans, farm animals, sport animals, and pets. Tissues, cells and their progeny of a biological entity obtained in vivo or cultured in vitro are also encompassed.

As used herein, the term "administering" includes oral administration, topical contact, administration as a suppository, intravenous, intraperitoneal, intramuscular, intralesional, intratumoral, intrathecal, intranasal, intraosseous, or subcutaneous administration to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arterial, intradermal, subcutaneous, intraperitoneal, intraventricular, intraosseous, and intracranial. Other modes of delivery include, but are not limited to, the use of liposomal formulations, intravenous infusion, transdermal patches, depot formulations, etc.

The term "treating" refers to an approach for obtaining beneficial or desired results including, but not limited to, a therapeutic benefit and/or a prophylactic benefit. "Therapeutic benefit" means any therapeutically relevant improvement in or effect on one or more diseases, conditions, or symptoms under treatment. Therapeutic benefit can also mean to effect a cure of one or more diseases, conditions, or symptoms under treatment. Furthermore, therapeutic benefit can also mean to increase survival. For prophylactic benefit, the compositions may be administered to a subject at risk of developing a particular disease, condition, or symptom, or to a subject reporting one or more of the physiological symptoms of a disease, even though the disease, condition, or symptom may not yet be present.

The term "survival" refers to a length of time following the diagnosis of a disease and/or beginning or completing a particular course of therapy for a disease (e.g., cancer or an infectious disease). The term "overall survival" includes the clinical endpoint describing patients who are alive for a defined period of time after being diagnosed with or treated for a disease, such as cancer. The term "disease-free survival" includes the length of time after treatment for a specific disease during which a patient survives with no sign of the disease (e.g., without known recurrence). In certain embodiments, disease-free survival is a clinical parameter used to evaluate the efficacy of a particular therapy, which in some instances is measured in units of 1 or 5 years. The term "progression-free survival" includes the length of time during and after treatment for a specific disease in which a patient is living with the disease without additional symptoms of the disease. In some embodiments, survival is expressed as a median or mean value.

The term "therapeutically effective amount" or "sufficient amount" refers to the amount of a recombinant polynucleotide or composition that is sufficient to effect beneficial or desired results. The therapeutically effective amount may vary depending upon one or more of: the subject and disease condition being treated, the weight and age of the subject, the severity of the disease condition, the immune status of the subject, the manner of administration and the like, which can readily be determined by one of ordinary skill in the art. The specific amount may vary depending on one or more of: the particular agent chosen, the target cell type, the location of the target cell in the subject, the dosing regimen to be followed, whether it is administered in combination with other compounds, timing of administration, and the physical delivery system in which it is carried.

For the purposes herein an effective amount is determined by such considerations as may be known in the art. The amount must be effective in achieving the desired therapeutic effect in a subject suffering from a disease such as an infectious disease or cancer. The desired therapeutic effect may include, for example, amelioration of undesired symptoms associated with the disease, prevention of the manifestation of such symptoms before they occur, slowing down the progression of symptoms associated with the disease, slowing down or limiting any irreversible damage caused by the disease, lessening the severity of or curing the disease, or improving the survival rate or providing more rapid recovery from the disease. Further, in the context of prophylactic treatment the amount may also be effective to prevent the development of the disease.

The term "pharmaceutically acceptable carrier" refers to a substance that aids the administration of an active agent to a cell, an organism, or a subject. "Pharmaceutically acceptable carrier" refers to a carrier or excipient that can be included in the compositions of the invention and that causes no significant adverse toxicological effect on the patient. Non-limiting examples of pharmaceutically acceptable carriers include water, sodium chloride (NaCl), normal saline solutions, lactated Ringer's, normal sucrose, normal glucose, binders, fillers, disintegrants, lubricants, coatings, sweeteners, flavors and colors, liposomes, dispersion media, microcapsules, cationic lipid carriers, isotonic and absorption delaying agents, and the like. The carrier may also comprise or consist of substances for providing the formulation with stability, sterility and isotonicity (e.g. antimicrobial preservatives, antioxidants, chelating agents and buffers), for preventing the action of microorganisms (e.g. antimicrobial and antifungal agents, such as parabens, chlorobutanol, phenol, sorbic acid and the like) or for providing the formulation with an edible flavor, etc. In some instances, the carrier is an agent that facilitates the delivery of an IL-10 inhibitor and/or a vaccine to a target cell or tissue. One of skill in the art will recognize that other pharmaceutical carriers are useful in the present invention.

The term "vaccine" refers to a biological composition that, when administered to a subject, has the ability to produce an acquired immunity to a particular pathogen or disease in the subject. Typically, one or more antigens, fragments of antigens, or polynucleotides encoding antigens or fragments of antigens that are associated with the pathogen or disease of interest are administered to the subject. Vaccines can comprise, for example, inactivated or attenuated organisms (e.g., bacteria or viruses), cells, proteins that are expressed from or on cells (e.g., cell surface or other proteins produced by cells (e.g., tumor cells)), proteins that are produced by organisms (e.g., toxins), or portions of organisms (e.g., viral envelope proteins or viral genes encoding various antigens). In some instances, cells are engineered to express proteins such that, when administered as a vaccine, they enhance the ability of a subject to acquire immunity to that particular cell type (e.g., enhance the ability of a subject to acquire immunity to a cancer cell or to an organism that causes an infectious disease such as a virus, a bacterium, a fungal organism, a protozoan, or a helminth). As used herein, the term "vaccine" includes, but is not limited to, recombinant polynucleotides of the present invention (e.g., viral-based vectors, such as CMV-based vectors or other viral vectors described herein) that can be used in viral vector vaccines), as well as viral particles, host cells, and pharmaceutical compositions that comprise recombinant polynucleotides of the present invention.

The term "unfolded protein response" or "UPR" refers to a cellular stress response that is conserved across many species, including mammals, yeast, and worms, and is activated in response to the accumulation of unfolded or misfolded proteins in the endoplasmic reticulum of a cell. Initially, the UPR functions to decrease protein translation, degrade misfolded proteins, and facilitate activation of signaling pathways that lead to increased production of molecular chaperones. If the UPR is sustained, eventually its functioning can induce apoptosis. Within the lumen of the endoplasmic reticulum, the UPR is initiated as BIP/Grp78 chaperones, which normally associate with the luminal domains of UPR-activating transmembrane proteins (thus preventing activation of the UPR), become dissociated from these proteins as BIP/Grp78 is forced to associate with unfolded or misfolded proteins. Cytomegaloviruses contain genes that inhibit the UPR (e.g., Human cytomegalovirus UL50, Rhesus cytomegalovirus Rh81, and Mouse cytomegalovirus M50), the protein products of which suppress IRE1-mediated XBP1 splicing via conserved sequences located at their N-terminal ends.

The term "group-specific antigen" or "gag" refers to a protein encoded by a retroviral gag gene. Gag genes encode the core structural proteins of retroviruses. In human immunodeficiency virus (HIV) and the closely related simian immunodeficiency virus (SIV), the gag gene encodes a gag polyprotein precursor (known in the case of HIV as Pr55Gag), which is subsequently proteolytically processed into the p17 matrix protein (MA), the p24 capsid protein (CA), the p7 nucleocapsid protein (NC), the SP1 and SP2 spacer peptides, and the p6 polypeptide that is located at the N-terminus of the gag polyprotein. Non-limiting examples of HIV and SIV gag protein sequences are set forth under UniProt reference numbers P04591 and P89153, respectively.

III. Methods for Inducing an Immune Response and Preventing or Treating Disease In one aspect, provided herein are methods for inducing an immune response against an antigen in a subject. In some embodiments, the method comprises administering to the subject a therapeutically effective amount of an interleukin 10 (IL-10) inhibitor and a vaccine. In particular embodiments, more than one IL-10 inhibitor is administered. The IL-10 inhibitor(s) may inhibit viral IL-10, cellular IL-10, or a combination thereof. In some embodiments, the method further comprises administering a pharmaceutically acceptable carrier. For example, delivery of the IL-10 inhibitor and/or the vaccine may be facilitated by use of a pharmaceutically acceptable carrier such as those described herein.

In a second aspect, provided herein are methods for preventing or treating a disease (e.g., an infectious disease and/or cancer) in a subject (e.g., a patient). In some embodiments, the method comprises inducing an immune response against an antigen (e.g., an antigen associated with an organism or cell that causes the disease) in the subject (i.e., administering to the subject a therapeutically effective amount of an IL-10 inhibitor and a vaccine), as described herein.

Any number of IL-10 inhibitors can be used in methods of the present invention. In some embodiments, the IL-10 inhibitor comprises a protein (e.g., an antibody, a fusion protein, a dominant-negative protein, or a truncated protein). In some embodiments, the IL-10 inhibitor comprises a small molecule. In some embodiments, an IL-10 inhibiting protein and a small molecule IL-10 inhibitor are used.

In some embodiments, the protein comprises an antibody. The antibody may, for example, be a polyclonal antibody, a monoclonal antibody, a single chain antibody, a chimeric antibody, a humanized antibody, a human antibody, a monovalent antibody, or a bispecific antibody. The antibody may also be an antigen-binding fragment of an antibody (e.g., Fab, $F(ab')_2$, Fv, scFv, or bivalent scFv). As non-limiting examples, the antibody may be an anti-IL-10 antibody, an anti-IL-10 receptor (IL-10R) antibody, or an anti-CD20 antibody. A non-limiting example of a suitable anti-IL-10 antibody is the anti-IL-10 1F11R1LALA antibody that is available from the National Institutes of Health Non-human Primate Reagent Resource, described in Example 2 below. Other anti-IL-10 antibodies are commercially available. Non-limiting examples of anti-CD20 antibodies include rituximab, obinutuzumab, ocaratuzumab, ocrelizumab, and veltuzumab. In some embodiments, a combination of two or more different antibodies are used to inhibit IL-10.

In some embodiments, the IL-10-inhibiting protein comprises a fusion protein. In some embodiments, the fusion protein binds to IL-10, thereby making IL-10 unavailable to interact with and activate IL-10 receptors. As a non-limiting example, a fusion protein that comprises an Fc polypeptide and an IL-10 receptor subunit (Fc-IL-10R), or a portion thereof, can be used. In some instances, the fusion protein is an Fc-IL-10R1 fusion protein. In some embodiments, the fusion protein inhibits binding of all proteins to IL-10R (e.g., IL-10R1). In some embodiments, the fusion protein has a high binding affinity (e.g., stronger than about $10^{-6}$ M, $10^{-7}$ M, $10^{-8}$ M, $10^{-9}$ M) for IL-10. In some embodiments, the fusion protein inhibits host and/or viral IL-10. In some embodiments, the fusion protein inhibits IL-10 receptor signaling.

In some embodiments, the IL-10-inhibiting protein comprises a portion of an IL-10 protein that comprises one or more mutations that increase affinity of the portion of the IL-10 protein for an IL-10 receptor. For example, substitution of Epstein-Barr virus IL-10 from alanine to isoleucine at position 87 enhances its receptor-binding ability, with reduction in the effective 50% inhibitory concentration value (for competitive binding against 125I-labeled human IL-10) from ~200 nM to ~6 nM (Ding Y. et al. *J. Exp. Med.* (2000) 191:213-224).

In some embodiments, the IL-10-inhibiting protein comprises a truncated IL-10 receptor protein (e.g., a truncated IL-10 receptor alpha subunit (IL10RA) protein). In some embodiments, the truncated IL-10 receptor protein functions as a dominant-negative IL-10 receptor protein. As a non-limiting example, a truncated IL-10 receptor protein can retain the extracellular and transmembrane domains, but be deficient in portion(s) of the protein that are necessary for intracellular signaling. Such truncated receptor proteins can be advantageous in that, in some embodiments, they can be expressed in a cell and localize to the cell membrane, but be deficient in their ability to activate IL-10 signaling when bound by a ligand. Non-limiting examples of amino acid sequences of suitable truncated IL-10 receptor proteins are set forth in SEQ ID NO:5 (i.e., a truncated *Macaca mulatta* IL10RA protein) and SEQ ID NO: 6 (i.e., a truncated human IL10RA protein) and include amino acid sequences having at least 80%, 85%, 90%, or 95% identity to SEQ ID NO:5 or SEQ ID NO:6. Furthermore, in some embodiments, a truncated IL-10 receptor protein can be expressed in the same cell as the antigen. Example 3 describes one such embodiment, where a truncated IL-10 receptor protein is expressed from an adenovirus-based vaccine vector.

In some embodiments, the IL-10-inhibiting protein comprises a truncated protein having IL-10-like activity. As a non-limiting example, a truncated rhesus cytomegalovirus interleukin-10 protein can be used, which is the ortholog of the human CMV LAcmvIL-10 sequence (i.e., a truncated IL-10-like protein that is expressed naturally in human CMV infection). A non-limiting example of an amino acid sequence of a suitable truncated protein having IL-10-like activity is set forth in SEQ ID NO:7 and includes amino acid sequences having at least 80%, 85%, 90%, or 95% identity to SEQ ID NO:7. Furthermore, in some embodiments, a truncated protein having IL-10-like activity can be expressed in the same cell as the antigen. Example 4 describes one such embodiment, where a truncated rhesus CMV protein is expressed from an adenovirus-based vaccine vector.

In some embodiments, the IL-10-inhibiting protein comprises a dominant-negative STAT3 protein. In certain embodiments, the dominant-negative STAT3 protein interferes with the function of normal STAT3 expressed in a cell such that STAT3 transducer of IL-10 receptor signaling is inhibited. As a non-limiting example, a vaccine described herein may express an antigen and a STAT3 protein carrying a mutation of tyrosine to phenylalanine (STAT3-YF) at a position usually phosphorylated in the IL-10 signaling cascade (e.g., tyrosine 705 in the human STAT3 protein). STAT3-YF shows a pronounced dominant-negative effect on the activation of wild-type STAT3 in stimulated cells. A non-limiting example of a human STAT3 amino acid sequence containing the Y705F mutation is set forth in SEQ ID NO:8 and includes amino acid sequences having at least 80%, 85%, 90%, or 95% identity to SEQ ID NO:8 and containing the Y705F mutation. As another non-limiting example, a vaccine described herein may express an antigen and a STAT3 protein carrying a mutation in the DNA-binding domain, as observed in some human cases of hyper-IgE syndrome. A non-limiting example of a human STAT3 amino acid sequence containing such a mutation (i.e., a deletion of valine 463) is set forth in SEQ ID NO:9 and includes amino acid sequences having at least 80%, 85%, 90%, or 95% identity to SEQ ID NO:9 and containing the V463 deletion. As yet another non-limiting example, a vaccine described herein may express an antigen and a STAT3 protein carrying a mutation in the SH2 domain, as observed in other human cases of hyper-IgE syndrome. A non-limiting example of a human STAT3 amino acid sequence containing such a mutation (i.e., a V637M mutation) is set forth in SEQ ID NO:10 and includes amino acid sequences having at least 80%, 85%, 90%, or 95% identity to SEQ ID NO:10 and containing the V637M mutation. A vaccine described herein may express any other dominant-negative form of a STAT3 protein known in the art.

In some embodiments, the IL-10 inhibitor comprises a small molecule IL-10 inhibitor. A non-limiting example of a small molecule IL-10 inhibitor is AS-101. AS-101 (ammonium trichloro[1,2-ethanediolato-O,O']-tellurate) is an immunomodulator that has the following structure:

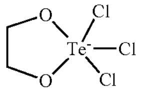

$NH_4^+$.

AS-101 inhibits the release of IL-10 by macrophages and monocytes, and blocks the transcription of IL-10 (see, e.g., Strassmann et al. *Cell. Immunol.* (1997) 176 (2): 180-185)) AS-101 is also a partial interferon-gamma agonist and augments the release of TNF-alpha.

In some embodiments, the vaccine comprises a recombinant polynucleotide comprising a viral genome, or a portion thereof, and a nucleic acid sequence encoding an antigen. In some embodiments, the recombinant polynucleotide further comprises a nucleic acid sequence encoding the IL-10 inhibitor. In some instances, the antigen and the IL-10 inhibitor are expressed from the same recombinant polynucleotide (i.e., the vaccine vector also expresses the IL-10 inhibitor). Non-limiting examples of suitable viral genomes (i.e., that can be used as viral vaccine vectors) include those from cytomegalovirus (CMV), adenovirus, adeno-associated virus, lentivirus, herpes virus, alphavirus, a retrovirus, poxvirus, and vesicular stomatitis virus. In some instances, the vaccine comprises a recombinant polynucleotide comprising a CMV genome, or a portion thereof, and a nucleic acid sequence encoding the antigen.

In some embodiments, the vaccine is an IL-10-deficient vaccine. In some embodiments, the IL-10-deficient vaccine comprises a recombinant polynucleotide comprising a viral genome (e.g., a CMV genome, herpes virus genome, or poxvirus genome), or a portion thereof, and a nucleic acid sequence encoding an antigen, wherein the viral genome or portion thereof comprises one or more immunomodulatory mutations, wherein the one or more immunomodulatory mutations comprise a mutation within a nucleic acid sequence encoding a viral protein that has interleukin-10-like activity. The one or more immunomodulatory mutations can be, for example, in a regulatory region and/or a protein coding region of the nucleic acid sequence encoding the viral protein that has IL-10-like activity. In some embodiments, the IL-10-deficient vaccine comprises a recombinant polynucleotide comprising a cytomegalovirus (CMV) genome, or a portion thereof, and a nucleic acid sequence encoding the antigen, wherein the CMV genome or portion thereof comprises one or more immunomodulatory mutations, wherein the one or more immunomodulatory mutations comprise a mutation within a nucleic acid sequence encoding a protein that has CMV interleukin-10 (CMV IL-10)-like activity.

In some embodiments, the nucleic acid sequence encoding the antigen is located within the viral (e.g., CMV) genome or portion thereof. In other embodiments, the nucleic acid sequence encoding the antigen is located outside of the viral genome or portion thereof (e.g., 5' and/or 3' of the viral genome or portion thereof). In some embodiments, nucleic acid sequences encoding antigen(s) are located both inside and outside (e.g., 5' to and/or 3' to) of the viral genome or portion thereof. In some embodiments, the recombinant polynucleotide comprises 1, 2, 3, 4, 5, or more viral genomes, or portions thereof. When the recombinant polynucleotide comprises more than one viral genome or a portion thereof, immunomodulatory mutations in nucleic acid sequences encoding proteins that have viral (e.g., CMV) IL-10-like activity can be made in one, some, or all of the viral genomes or portions thereof (e.g., one, some, or all of the nucleic acid sequences encoding proteins that have viral IL-10-like activity).

In some embodiments, when a CMV genome or portion thereof is used, the CMV is a CMV that can infect human cells. In particular embodiments, the CMV is a CMV that can replicate in human cells. In some instances, the CMV is a CMV that can only enter or replicate in human cells. In some embodiments, the CMV is a CMV that can infect non-human primate cells (e.g., simian cells, chimpanzee cells, or rhesus macaque cells). In particular embodiments, the CMV is a CMV that can replicate in non-human primate cells. In some instances, the CMV is a CMV that can only enter or replicate in non-human primate cells. In some embodiments, the CMV is a CMV that can infect rodent cells (e.g., mouse cells or rat cells). In particular embodiments, the CMV is a CMV that can replicate in rodent cells. In some instances, the CMV is a CMV that can only enter or replicate in rodent cells. In some embodiments, the CMV is selected from the group consisting of Human cytomegalovirus (HCMV), Simian cytomegalovirus (SCCMV or AGMCMV), Baboon cytomegalovirus (BaCMV), Owl monkey cytomegalovirus (OMCMV), Squirrel monkey cytomegalovirus (SMCMV), and Rhesus cytomegalovirus (RhCMV). Non-limiting examples of nucleic acid sequences that encode suitable viral genomes include those set forth under NCBI Reference Sequence numbers NC_006273.2 (HCMV), FJ483969.2 (SCCMV), NC_006150.1 (RhCMV), AY186194.1 ((RhCMV strain 68-1), and DQ120516.1 (Cercopithecine herpesvirus 8 isolate CMV 180.92).

In some embodiments, the protein having IL-10-like activity is one that has CMV IL-10-like activity such as human CMV IL-10 (HCMVIL-10) or rhesus macaque CMV IL-10 (RhCMVIL-10). Immunomodulatory mutations can be introduced into genes for other (e.g., homologous) proteins, such as the genes that encode proteins having IL-10-like activity in SCCMV/AGMCMV, BaCMV, OMCMV, or SMCMV, depending on the particular CMV genome being used to construct a recombinant polynucleotide for use in a vaccine according to methods of the present invention. In some embodiments, a protein that has CMV IL-10-like activity is encoded by the nucleic acid sequence set forth under SEQ ID NO:3 or 4.

Mutations (e.g., immunomodulatory mutations) introduced into recombinant polynucleotides for use in vaccines according to methods of the present invention can comprise deletions, insertions, and/or substitutions (e.g., conservative or non-conservative substitutions) of one or more nucleotides. In some embodiments, a mutation (e.g., an immunomodulatory mutation) comprises the insertion of a gene, or a portion of a gene. In other embodiments, a mutation comprises an insertion of a nucleic acid sequence that encodes a protein, or a portion of a protein. In some embodiments, a mutation comprises a deletion of an entire gene sequence, or a portion thereof. As a non-limiting example, one, two or more exons of a gene can be deleted. In some embodiments, a recombinant polynucleotide comprises the deletion of the first two exons of a gene for a protein that has viral IL-10-like activity, such as a protein that has CMV IL-10-like activity (e.g., the first two exons of RhCMVIL-10 are deleted).

Mutations (e.g., immunomodulatory mutations) introduced into recombinant polynucleotides for use in vaccines according to methods of the present invention can increase or decrease the expression (e.g., mRNA and/or protein expression) and/or activity of a gene. In some embodiments, a mutation within a gene for a protein that has viral IL-10-like activity, such as a protein that has CMV IL-10-like activity (e.g., a mutation comprising the deletion of the first two exons of a gene encoding a protein that has CMV IL-10-like activity), decreases or eliminates the activity of the protein having viral (e.g., CMV) IL-10-like activity. In some embodiments, the reduction or inactivation of the protein having viral IL-10-like activity produces a synergistic effect when combined with one or more other immunomodulatory mutations.

The vaccines used in methods of the present invention may contain or encode any antigen, or a portion thereof, so long as it produces an immune response against the desired cell type or pathogenic organism. In some embodiments, the antigen is a non-CMV antigen. In some embodiments, the antigen is an infectious disease antigen. In other embodiments, the antigen is a tumor-associated antigen (TAA).

In some embodiments, the infectious disease antigen is a bacterial infectious disease antigen. In some embodiments, the infectious disease antigen is a viral infectious disease antigen. In some embodiments, the infectious disease antigen is a fungal infectious disease antigen. In some embodiments, the infectious disease antigen is a protozoal infectious disease antigen. In some embodiments, the infectious disease antigen is a helminthic infectious disease antigen. In some embodiments, the infectious disease antigen is a bacterial, viral, fungal, protozoal, and/or helminthic infectious disease antigen. In some cases, the antigen is from a parasite. Non-limiting examples of suitable viral infectious disease antigens are those derived from simian immunodeficiency virus (SIV), human immunodeficiency virus (HIV), hepatitis C virus, herpes simplex virus, Epstein-Barr virus, or any combination thereof. As further non-limiting examples, the infectious disease antigen can comprise a retroviral group-specific antigen (gag) protein (e.g., an HIV or SIV gag protein). In some embodiments, the infectious disease antigen is a bacterial infectious disease antigen from *Mycobacterium tuberculosis.*

A tumor-associated antigen (TAA) can be derived from any cancer cell. TAAs include, but are not limited to, products of mutated oncogenes and mutated tumor suppressor genes, overexpressed or aberrantly expressed cellular proteins, antigens that are produced by oncogenic viruses, oncofetal antigens, altered cell surface glycolipids and glycoproteins, antigens that are aberrantly processed in tumor cells for presentation on MHC molecules, and antigens that are tumor cell type-specific. In some embodiments, a TAA is one that newly arises in a tumor (e.g., a subject's tumor). Such neoantigens can arise, for example, as a consequence of a tumor-specific mutation. In some embodiments, a TAA is a cell surface protein (e.g., that is normally present on the surface of a cell), or a portion thereof, that is altered as a consequence of a mutation in a gene encoding the cell surface protein.

A TAA can be derived from, for example, a colorectal cancer cell, a colon cancer cell, an anal cancer cell, a liver cancer cell, an ovarian cancer cell, a breast cancer cell, a lung cancer cell, a bladder cancer cell, a thyroid cancer cell, a pleural cancer cell, a pancreatic cancer cell, a cervical cancer cell, a prostate cancer cell, a testicular cancer cell, a bile duct cancer cell, a gastrointestinal carcinoid tumor cell, an esophageal cancer cell, a gall bladder cancer cell, a rectal cancer cell, an appendix cancer cell, a small intestine cancer cell, a stomach (gastric) cancer cell, a renal cancer (e.g., renal cell carcinoma) cell, a central nervous system cancer cell, a skin cancer cell, an oral squamous cell carcinoma cell, a choriocarcinoma cell, a head and neck cancer cell, a bone cancer cell, an osteogenic sarcoma cell, a fibrosarcoma cell, a neuroblastoma cell, a glioma cell, a melanoma cell, a leukemia (e.g., acute lymphocytic leukemia, chronic lymphocytic leukemia, acute myelogenous leukemia, chronic myelogenous leukemia, or hairy cell leukemia) cell, a lymphoma (e.g., non-Hodgkin's lymphoma, Hodgkin's lymphoma, B-cell lymphoma, or Burkitt's lymphoma) cell, a multiple myeloma cell, or any combination thereof. In particular embodiments, the TAA is derived from an ovarian cancer cell, a melanoma cell, a prostate cancer cell, or a combination thereof.

Non-limiting examples of TAAs include the melanoma-associated antigens (MAGEs). MAGE proteins contain a conserved domain that is about 200 amino acids in length and is usually located near the C-terminal end of the protein, although the conserved domain is located closer to the central portion of some MAGE proteins. Human MAGE proteins include MAGEA1, MAGEA2, MAGEA2B, MAGEA3, MAGEA4, MAGEA5, MAGEA6, MAGEA7P, MAGEA8, MAGEA9, MAGEA9B, MAGEA10, MAGEA11, MAGEA12, MAGEA13P, MAGEB1, MAGEB2, MAGEB3, MAGEB4, MAGEB5, MAGEB6, MAGEB10, MAGEB16, MAGEB17, MAGEB18, MAGEC1, MAGEC2, MAGEC3, MAGED1, MAGED2, MAGED3 (also known as "trophin" or "TRO"), MAGED4, MAGED4B, MAGEE1, MAGEE2, MAGEF1, MAGEEG1 (also known as "NSMCE3"), MAGEH1, MAGEL2, and NDN. Additional non-limiting examples of TAAs that are useful for methods of the present invention include NY-ESO-1 and prostate-specific antigen (PSA).

Methods of the present invention can be used to treat cancer at any stage. In some embodiments, the cancer is an advanced cancer. In some embodiments, the cancer is a metastatic cancer. In some embodiments, the cancer is a drug-resistant cancer.

In order to improve the magnitude and/or character of an immune response induced (e.g., in a subject) by a vaccine used in methods of the present invention, one or more immunomodulatory mutations can comprise a mutation that increases the expression or activity of an immunostimulatory protein. In some embodiments, the one or more immunomodulatory mutations comprise a nucleic acid sequence that encodes an immunostimulatory protein (e.g., the insertion of nucleic acid sequence encoding an immunostimulatory protein). As used herein, the term "immunostimulatory protein" refers to any protein that increases the magnitude of an immune response (e.g., in a subject) and/or changes the character of an immune response such that acquired immunity (e.g., against a desired cell type or pathogen) is enhanced.

As a non-limiting example, the immunostimulatory protein can be a cytokine. In some embodiments, the cytokine is an interleukin. In some embodiments, the cytokine is a chemokine. In some embodiments, the cytokine is an interferon (e.g., a type I interferon, type II interferon (interferon-gamma in humans), and/or another type II interferon). In some embodiments, the cytokine is a lymphokine. In some embodiments, the cytokine is a tumor necrosis factor (e.g., tumor necrosis factor-alpha). In some embodiments, the cytokine is an interleukin, a chemokine, an interferon, a lymphokine, a tumor necrosis factor, or any combination thereof. In particular embodiments, the cytokine encoded by a nucleic acid sequence within a recombinant polynucleotide of the present invention comprises an interleukin. Suitable interleukins include those that stimulate the immune response such as interleukin-2 (IL-2), interleukin-12 (IL-12), interleukin-15 (IL-15), or a combination thereof.

In some embodiments, an immunomodulatory mutation is introduced into a nucleic acid sequence within a recombinant polynucleotide (i.e., to be used as a vaccine according to methods of the present invention), wherein the nucleic acid sequence encodes a protein that in its unmutated state produces gene product(s) that inhibit antigen presentation by a major histocompatibility complex molecule. Additional immunomodulatory mutations that can be introduced into recombinant polynucleotides to be used as vaccines according to methods of the present invention include, but are not limited to, mutations introduced into the Rh182, Rh183, Rh184, Rh185, Rh186, Rh187, Rh188, and/or Rh189 regions of the RhCMV genome or portion thereof, US2, US3, US4, US5, US6, US7, US8, US9, US10, and/or US11 of the HCMV genome or portion thereof, and homologs thereof (see, e.g., Hansen et al. *J. Virol.* (2003) 77:6620-6636). Introducing mutations into the Rh182, Rh184, Rh185, or Rh189 regions of RhCMV or the US2, US3, US6, or US11 regions of HCMV are useful, for example, for reducing the ability of CMV to inhibit antigen presentation by major histocompatibility complex (MHC) molecules (e.g., class I and/or class II MHC molecules). Rh187 and US8 are involved in binding MHC molecules (see, e.g., Tirabassi et al. *J. Virol.* (2002) 76:6832-6835) and thus can be used to modulate MHC-associated antigen presentation.

In some instances, it is useful to increase tropism or selectivity for particular target cell or tissue type(s). This can be achieved, for example, by introducing mutation(s) into a recombinant polynucleotide that increase tropism or selectivity for the desired cell or tissue type(s). In some embodiments, a mutation that increases or imparts tropism or selectivity (e.g., for a target cell or tissue) is introduced into a recombinant polynucleotide comprising a viral genome (e.g., CMV genome), or a portion thereof, that is used as a vaccine vector. Non-limiting examples of suitable target cells are antigen-presenting cells, tumor cells, fibroblasts, epithelial cells, endothelial cells, and combinations thereof. Suitable antigen-presenting cells include, but are not limited to, dendritic cells, macrophages, and B cells. In particular embodiments, the antigen-presenting cell is a dendritic cell.

Another approach for increasing or imparting target cell or tissue tropism or selectivity is to introduce mutations into a recombinant polynucleotide (e.g., comprising a viral genome (e.g., CMV genome), or a portion thereof, that is used as a vaccine vector) that result in the modification of proteins that are positioned on the outside of a virion. As a non-limiting example, a viral envelope protein can be modified by the addition of a blocking domain that decreases or prevents entry of the virus into a cell, unless the blocking domain is cleaved, e.g., by a protease expressed by a target cell. For example, proteases such as matrix metalloproteases that are expressed by tumor cells of interest can cleave off envelope protein blocking domains, thereby allowing virus entry into the tumor cells of interest and increasing tropism or selectivity for those target cells.

Furthermore, tropism or selectivity for a target cell or tissue type can be increased or imparted by introducing a nucleic acid sequence (e.g., within a recombinant polynucleotide comprising a viral genome (e.g., CMV genome), or a portion thereof, that is used as a vaccine vector) that encodes a cellular targeting ligand. To serve as non-limiting examples, a cellular targeting ligand can be an antibody or fragment thereof that recognizes a target cell antigen, a ligand that is recognized by a target cell cognate receptor, a viral capsid protein that recognizes a target cell, or any combination thereof. Non-limiting examples of antibodies and fragments thereof that recognize target cell antigens include antibodies that recognize dendritic cell-specific intercellular adhesion molecule-3-grabbing non-integrin (DC-SIGN; also known as CD209), CD40, CD64, class II MHC molecules, and DEC205 (also known as CD205), all of which are expressed by dendritic cells.

Suitable ligands that are recognized by target cell cognate receptors include, but are not limited to, CD40L (which is also known as CD154 and binds to CD40, which is expressed, e.g., by dendritic cells) and ICAM3 (which has high affinity for DC-SIGN that is expressed by, e.g., APCs such as dendritic cells). In particular embodiments, the cellular targeting ligand is CD40L/CD154.

Non-limiting examples of viral capsid proteins that are recognized by target cells include Ad16, Ad35, and Ad37 virus fiber proteins (i.e., for targeting dendritic cells) and Sindbis virus envelope glycoproteins (which can also be used for targeting dendritic cells, via DC-SIGN).

Additional mutations to increase target tropism or selectivity that can be introduced into a recombinant polynucleotide used in a vaccine according to methods of the present invention include mutations (e.g., deletions) within the Rh13.1, Rh61/Rh60, Rh157.4, Rh157.5, and/or Rh157.6 genes of RhCMV, or homologs thereof. Human CMV orthologs of Rh13.1, Rh61/Rh60, Rh157.4, Rh157.5, and Rh157.6 include, but are not limited to, RL13, UL36 (also known as viral inhibitor of caspase-8-induced apoptosis (vICA)), UL130, UL128, and UL131, respectively. Rh13.1 and RL13 are involved in, for example, inhibiting growth of the virus in fibroblasts. Rh157.4, Rh157.5, Rh157.6, UL130, UL128, and UL131 encode three components of an entry receptor for non-fibroblast cells (e.g., endothelial and epithelial cells).

Viral (e.g., CMV) genomes typically contain nucleic acid sequences that encode for proteins that suppress the unfolded protein response (UPR) in a host. In some instances, it is desirable to further suppress the UPR (e.g., in a host being administered an IL-10 inhibitor and a vaccine according to methods of the present invention), for example by further increasing the expression or activity of a viral (e.g., CMV) protein that suppresses the UPR. In other instances, it is desirable to decrease or eliminate the ability of a virus (e.g., CMV) to suppress the UPR, for example, by decreasing the expression or activity of a viral (e.g., CMV) protein that suppresses the UPR. In CMV, proteins that are known to suppress the UPR include, Human cytomegalovirus UL50, Rhesus cytomegalovirus Rh81, and Mouse cytomegalovirus M50. In some embodiments, a recombinant polynucleotide used in a vaccine according to methods of the present invention comprises or further comprises an immunomodulatory mutation that increases or decreases the UPR (e.g., in a subject). In varying embodiments, the immunomodulatory mutation that increases or decreases the UPR decreases or increases the expression and/or activity of Human cytomegalovirus UL50, Rhesus cytomegalovirus Rh81, Mouse cytomegalovirus M50, or a homolog thereof.

In some embodiments, a recombinant polynucleotide used in a vaccine according to methods of the present invention contains a nucleic acid sequence that encodes a selectable marker. The nucleic acid sequence can be located within a viral (e.g., CMV) genome or portion thereof, outside of (e.g., 5' and/or 3' to) the viral genome or portion thereof, or a combination thereof. A selectable marker is useful, for example, when a polynucleotide to be used in a vaccine is being recombinantly modified, especially when it is desirable to screen a population of modified polynucleotides (e.g., using bacterial, yeast, plant, or animal cells) for those that have incorporated the desired modification(s) (e.g., insertion, deletion, or a combination thereof). As a non-limiting example, one or more exons of a gene of interest (e.g., a viral (e.g., CMV) gene encoding a protein that has IL-10-like activity) in a recombinant polynucleotide can be deleted by recombinantly replacing the exon(s) with a nucleic acid sequence encoding a selectable marker (e.g., an antibiotic resistance gene such as a gene that encodes resistance to Zeocin). The nucleic acid sequence encoding the selectable marker can optionally be under the control of a promoter (e.g., EM7 promoter) and/or other regulatory sequence(s). Whether the polynucleotide is recombinantly modified within a cell (e.g., a bacterial cell, for example, using Red/ET recombination) or is recombinantly modified and subsequently introduced into a cell (e.g., bacterial, yeast, plant, or animal cell) for screening, the selectable marker can be used to identify which cells contain polynucleotides that have incorporated a modification of interest. Treating the cells that contain the recombinant polynucleotides with Zeocin will identify which cells contain recombinant polynucleotides that have incorporated the antibiotic resistance gene (i.e., the cells that survive after Zeocin treatment must have incorporated the antibiotic resistance gene). If desired, the recombinant polynucleotides can be further screened (e.g., purified from the cells, amplified, and sequenced), in order to verify that the desired modification has been recombinantly introduced into the polynucleotide at the correct position.

When the selectable marker is an antibiotic resistance gene, the gene can confer resistance to Zeocin, ampicillin, tetracycline, or another appropriate antibiotic that will be known to one of skill in the art. In some embodiments, a selectable marker is used that produces a visible phenotype, such as the color of an organism or population of organisms. As a non-limiting example, the phenotype can be examined by growing the organisms (e.g., cells or other organisms that contain the recombinant polynucleotide) and/or their progeny under conditions that result in a phenotype, wherein the phenotype may not be visible under ordinary growth conditions.

In some embodiments, the selectable marker used for identifying cells that contain a polynucleotide containing a modification of interest is a fluorescently tagged protein, a chemical stain, a chemical indicator, or a combination thereof. In other embodiments, the selectable marker responds to a stimulus, a biochemical, or a change in environmental conditions. In some instances, the selectable marker responds to the concentration of a metabolic product, a protein product, a drug, a cellular phenotype of interest, a cellular product of interest, or a combination thereof.

Commonly, recombinant polynucleotides that are used in vaccines will contain one or more regulatory sequences. The regulatory sequence(s) can be located within a viral (e.g., CMV) genome or portion thereof, outside of (e.g., 5' and/or 3' to) the viral genome or portion thereof, or a combination thereof. In some embodiments, the regulatory sequence(s) are recombinantly introduced into the polynucleotide. For example, one or more regulatory sequences can be introduced into a viral genome or portion thereof that are not present in the natural viral genome. Alternatively, a regulatory sequence that is present in the natural viral genome can be deleted or otherwise modified.

In some embodiments, the regulatory sequence(s) control the expression and/or activity of a gene or region within a viral (e.g., CMV) genome, or a portion thereof. In some embodiments, the regulatory sequence(s) control the expression and/or activity of an antigen-encoding sequence. In some embodiments, the regulatory sequence(s) control the expression and/or activity of an immunostimulatory protein-encoding sequence. In some embodiments, the regulatory sequence(s) control the expression and/or activity of a selectable marker-encoding sequence. In some embodiments, the regulatory sequence(s) control the expression and/or activity of a gene or region within a viral genome or a portion thereof, an antigen-encoding sequence, an immunostimulatory protein-encoding sequence, a selectable marker-encoding sequence, a variant thereof, or a combination thereof.

Depending on the cell system used, the regulatory sequence(s) may comprise one or more transcription and translation control elements, including promoters, transcription enhancers, transcription terminators, translation initiators (e.g., Kozak sequences, internal ribosomal entry sequences), intronic sequences, and the like. Useful promoters can be derived from viruses or any other organism, e.g., prokaryotic or eukaryotic organisms. Promoters may also be inducible (i.e., capable of responding to environmental factors and/or external stimuli that can be artificially controlled). Non-limiting examples of promoters include unmodified and modified bacterial T7 promoters such as the EM7 promoter, the EFla promoter, RNA polymerase II promoters (e.g., pGAL7 and pTEF1), RNA polymerase III promoters (e.g., RPR-tetO, SNR52, and tRNA-tyr), the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6), an enhanced U6 promoter, a human H1 promoter (H1), etc. Suitable polyadenylation sequences and terminators include, but are not limited to, SV40, hGH, BGH, rbGlob SNR52, and RPR polyadenylation and terminator sequences. Additionally, various primer binding sites may be incorporated into a vector to facilitate vector cloning, sequencing, genotyping, and the like. In some embodiments, a "CAG promoter" is used as the regulatory sequence, which comprises a CMV early enhancer, a chicken beta-actin gene promoter, a first exon of the chicken beta-actin gene, a first intron of the chicken beta-actin gene, and a splice acceptor of the rabbit beta-globin gene. Promoters may contain intronic sequences (e.g., an EFla intron A sequence). Other suitable promoter, enhancer, terminator, and primer binding sequences will readily be known to one of skill in the art.

In some embodiments, the IL-10 inhibitor and the vaccine are administered to the subject before any symptoms or sequelae of the disease (e.g., infectious disease, or cancer) develop. In other embodiments, the subject has signs, symptoms, or sequelae of the disease. In some instances, treatment results in a reduction or elimination of the signs, symptoms, or sequelae of the disease.

In some embodiments, prevention and/or treatment includes administering an IL-10 inhibitor and a vaccine directly to a subject. As a non-limiting example, the IL-10 inhibitor and the vaccine can be delivered directly to a subject, e.g., by local injection or systemic administration. In some instances, intratumoral injection is used. In some embodiments, the vaccine and the IL-10 inhibitor are present in the same composition (e.g., present in a single pharmaceutical composition that includes a pharmaceutically acceptable carrier). In some instances, an antigen (or a portion thereof) and an IL-10 inhibitor (e.g., a small molecule IL-10 inhibitor or an IL-10 inhibitor protein) are combined into a single composition. In some instances, a vaccine vector and an IL-10 inhibitor are combined into a single composition. In some instances, an antigen and an IL-10 inhibitor are expressed from a single recombinant polynucleotide.

The IL-10 inhibitor and the vaccine can be administered at about the same time (e.g., within about 1, 2, 3, 4, 5, 6, 7, 8, 9, 10, 11, 12, 13, 14, 15, 16, 17, 18, 19, 20, 21, 22, 23, or 24 hours of each other), or they can be administered sequentially. In some embodiments, the IL-10 inhibitor is administered before the vaccine (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more days before the vaccine is administered). In some embodiments, the IL-10 inhibitor is administered after the vaccine (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more days after the vaccine is administered). In some embodiments, the IL-10 inhibitor is administered both before and after the vaccine is administered. In some embodiments, only one dose of the IL-10 inhibitor is administered. In some embodiments, 2, 3, 4, 5, 6, 7, 8, 9, 10, or more doses of the IL-10 inhibitor are administered. In some embodiments, only one dose of the vaccine is administered. In some embodiments, 2, 3, 4, 5, 6, 7, 8, 9, 10, or more doses of the vaccine are administered (e.g., 1, 2, 3, 4, 5, 6, 7, 8, 9, or more booster doses are administered). When 2 or more doses of the vaccine are administered, some or all of the vaccine doses may be preceded and/or followed by a dose of the IL-10 inhibitor.

Whether the IL-10 inhibitor and the vaccine are administered at about the same time or sequentially, the IL-10 inhibitor and vaccine can be administered by different routes, or the same route.

A particular dose of the IL-10 inhibitor and/or the vaccine may be administered all at once, or may be divided into 2, 3, 4, 5, 6, 7, 8, or more subdoses. The subdoses may be administered about 1, 2, 3, 4, 5, 6, 7, 8, 9, 10, 11, 12, 13, 14, 15, 16, 17, 18, 19, 20, 21, 22, 23, 24, or more hours apart, about 1, 2, 3, 4, 5, 6, 7, or more days apart, or another appropriate interval.

In some embodiments, a dose of the IL-10 inhibitor (e.g., a protein such as an antibody or fusion protein) is administered at a concentration of about 1, 2, 3, 4, 5, 10, 15, 20, 25, 30, 35, 40, 45, 50, 55, 60, 65, 70, 75, 80, 85, 90, 95, or 100 mg/mL. In some instances, a concentration of about 30 mg/mL is used.

In some embodiments, a dose of the vaccine comprises between about $10^4$ and about $10^{13}$ plaque-forming units (pfu) (e.g., about $10^4$, $\mathbf{10^5}$, $\mathbf{10^6}$, $\mathbf{10^7}$, $\mathbf{10^8}$, $\mathbf{10^9}$, $\mathbf{10^{10}}$, $\mathbf{10^{11}}$, $\mathbf{10^{12}}$, or $10^{13}$ pfu). In some embodiments, a dose comprises about $10^4$ pfu to about $10^5$ pfu, about $10^4$ pfu to about $10^6$ pfu, about $10^4$ pfu to about $10^7$ pfu, about $10^4$ pfu to about $10^8$ pfu, about $10^4$ pfu to about $10^9$ pfu, about $10^4$ pfu to about $10^{10}$ pfu, about $10^4$ pfu to about $10^{11}$ pfu, about $10^4$ pfu to about $10^{12}$ pfu, about $10^4$ pfu to about $10^{13}$ pfu, about $10^5$ pfu to about $10^6$ pfu, about $10^5$ pfu to about $10^7$ pfu, about $10^5$ pfu to about $10^8$ pfu, about $10^5$ pfu to about $10^9$ pfu, about $10^5$ pfu to about $10^{10}$ pfu, about $10^5$ pfu to about $10^{11}$ pfu, about $10^5$ pfu to about $10^{12}$ pfu, about $10^5$ pfu to about $10^{13}$ pfu, about $10^6$ pfu to about $10^7$ pfu, about $10^6$ pfu to about $10^8$ pfu, about $10^6$ pfu to about $10^9$ pfu, about $10^6$ pfu to about $10^{10}$ pfu, about $10^6$ pfu to about $10^{11}$ pfu, about $10^6$ pfu to about $10^{12}$ pfu, about $10^6$ pfu to about $10^{13}$ pfu, about $10^7$ pfu to about $10^8$ pfu, about $10^7$ pfu to about $10^9$ pfu, about $10^7$ pfu to about $10^{10}$ pfu, about $10^7$ pfu to about $10^{11}$ pfu, about $10^7$ pfu to about $10^{12}$ pfu, about $10^7$ pfu to about $10^{13}$ pfu, about $10^8$ pfu to about $10^9$ pfu, about $10^8$ pfu to about $10^{10}$ pfu, about $10^8$ pfu to about $10^{11}$ pfu, about $10^8$ pfu to about $10^{12}$ pfu, about $10^8$ pfu to about $10^{13}$ pfu, about $10^9$ pfu to about $10^{10}$ pfu, about $10^9$ pfu to about $10^{11}$ pfu, about $10^9$ pfu to about $10^{12}$ pfu, about $10^9$ pfu to about $10^{13}$ pfu, about $10^{10}$ pfu to about $10^{11}$ pfu, about $10^{10}$ pfu to about $10^{12}$ pfu, about $10^{10}$ pfu to about $10^{13}$ pfu, about $10^{11}$ pfu to about $10^{12}$ pfu, about $10^{11}$ pfu to about $10^{13}$ pfu, or about $10^{12}$ pfu to about $10^{13}$ pfu. In particular embodiments, a dose comprises between about $10^4$ and about $2\times10^{11}$ pfu.

In some embodiments, additional compounds or medications can be co-administered to the subject. Such compounds or medications can be co-administered for the purpose of alleviating signs or symptoms of the disease being treated, reducing side effects caused by induction of the immune response, etc. The dose of the IL-10 inhibitor, vaccine, and/or any additional compounds or medications will vary depending on factors such as the particular antigen to which an immune response is being induced, characteristics of the chosen IL-10 inhibitor, vaccine, or other compound, immune status of the subject, age of the subject, weight of the subject, concomitant medical conditions, route of administration, etc.

In some embodiments, a sample (e.g., a test sample or a reference sample) is obtained from a subject (e.g., a subject in whom an immune response against an antigen is to be induced or a subject in whom a disease is to be prevented and/or treated). In particular embodiments, the sample is obtained for the purposes of determining the presence or level of one or biomarkers. Determining the presence or level of biomarkers(s) can be used to, as non-limiting examples, determine response to treatment or to select an appropriate composition or method for the prevention or treatment of a disease.

In some embodiments, a test sample is obtained from the subject. The test sample can be obtained before and/or after an IL-10 inhibitor and/or vaccine is administered to the subject. Non-limiting examples of suitable samples include blood, serum, plasma, cerebrospinal fluid (CSF), tissue, saliva, urine, and combinations thereof. In some instances, the sample comprises normal tissue. In other instances, the sample comprises abnormal tissue (e.g., cancer tissue). The sample can also be made up of a combination of normal and abnormal cells (e.g., cancer cells). In some instances, the sample is obtained as a biopsy sample or fine needle aspirate (FNA) sample. In some embodiments, the tissue comprises one or more types of immune cells.

In some embodiments, a reference sample is obtained. The reference sample can be obtained, for example, from the subject (i.e., the subject being treated or in whom an immune response is being induced). The reference sample can be also be obtained from a different subject and/or a population of subjects. In some instances, the reference sample is either obtained from the subject, a different subject, or a population of subjects before and/or after the IL-10 inhibitor and/or the vaccine is administered to the subject, and comprises normal tissue. In other instances, the reference sample comprises abnormal tissue and is obtained from the subject and/or from a different subject or a population of subjects.

In some embodiments, the level of one or more biomarkers is determined in the test sample and/or reference sample. Non-limiting examples of suitable biomarkers include antigens, antibodies against antigens, immune cell numbers and/or activation levels, capacity for immune cell responses to an antigen after in vitro stimulation, immunostimulatory proteins, cytokines, interleukins, tumor necrosis factors, interferons, and other molecules that play roles in modulating immune responses. Further non-limiting examples of suitable biomarkers include C-reactive protein, interferon-gamma, IL-1beta, IL-2, IL-4, IL-5, IL-6, IL-8, IL-10, IP-10, IL-12, IL-15, IL-13, IL-17, IL-21, IL-23, IP-10, M-CSF, MCP-1, MIP-1alpha, MIP-1beta, transforming growth factor-beta, tumor necrosis factor-alpha, IFN-γ CXCL13, CXCR5, CCR7, CD3, CD4, CD8, CD27, CD45RA, CD80, CD83, prostaglandin E2, and combinations thereof.

Typically, the level of a biomarker in a sample (e.g., test sample) is compared to the level of the biomarker in a reference sample. Depending on the biomarker, an increase or a decrease relative to a normal control or reference sample can be indicative of the presence of a disease, or response to treatment for a disease. In some embodiments, an increased level of a biomarker in a sample (e.g., test sample), and hence the presence of a disease (e.g., an infectious disease or cancer), increased risk of the disease, or response to treatment is determined when the biomarker levels are at least, e.g., about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 50-fold, 100-fold, 1,000-fold, or 10,000-fold higher in comparison to a negative control. In other embodiments, a decreased level of a biomarker in the test sample, and hence the presence of the disease, increased risk of the disease, or response to treatment is determined when the biomarker levels are at least, e.g., about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 50-fold, 100-fold, 1,000-fold, or 10,000-fold lower in comparison to a negative control.

The biomarker levels can be detected using any method known in the art, including the use of antibodies specific for the biomarkers. Exemplary methods include, without limitation, PCR, Western Blot, dot blot, enzyme-linked immunosorbent assay (ELISA), radioimmunoassay (RIA), immunoprecipitation, immunofluorescence, FACS analysis, electrochemiluminescence, and multiplex bead assays (e.g., using Luminex or fluorescent microbeads). In some instances, nucleic acid sequencing is employed.

In certain embodiments, the presence of decreased or increased levels of one or more biomarkers is indicated by a detectable signal (e.g., a blot, fluorescence, chemiluminescence, color, radioactivity) in an immunoassay or PCR reaction (e.g., quantitative PCR). This detectable signal can be compared to the signal from a reference sample or to a threshold value.

In some embodiments, the results of the biomarker level determinations are recorded in a tangible medium. For example, the results of diagnostic assays (e.g., the observation of the presence or decreased or increased presence of one or more biomarkers) and the diagnosis of whether or not there is an increased risk or the presence of a disease (e.g., an infectious disease or cancer) or whether or not a subject is responding to treatment can be recorded, e.g., on paper or on electronic media (e.g., audio tape, a computer disk, a CD, a flash drive, etc.).

In other embodiments, the methods further comprise the step of providing a diagnosis or a prognosis to the patient (i.e., the subject) and/or the results of treatment.

IV. Kits

In another aspect, kits are provided herein. In some embodiments, the kit comprises an IL-10 inhibitor described herein and a vaccine described herein. In some embodiments, the kit is for inducing an immune response against an antigen (e.g., in a subject). In other embodiments, the kit is for preventing or treating a disease. In particular embodiments, the kit is for preventing or treating an infectious disease described herein and/or a cancer described herein.

Kits of the present invention can be packaged in a way that allows for safe or convenient storage or use (e.g., in a box or other container having a lid). Typically, kits of the present invention include one or more containers, each container storing a particular kit component such as an Il-10 inhibitor, a vaccine, a reagent, a control sample, and so on. The choice of container will depend on the particular form of its contents, e.g., a kit component that is in liquid form, powder form, etc. Furthermore, containers can be made of materials that are designed to maximize the shelf-life of the kit components. As a non-limiting example, kit components that are light-sensitive can be stored in containers that are opaque.

In some embodiments, the kit contains one or more reagents. In some instances, the reagents are useful for preparing an IL-10 inhibitor and/or a vaccine for administration to a subject (e.g., pharmaceutically acceptable carriers), or for obtaining or processing a sample (e.g., for the measurement of biomarkers). In some embodiments, the kit contains paraphernalia for administering the IL-10 inhibitor and/or vaccine to the subject (e.g., syringes, needles, vials), obtaining a sample from a subject (e.g., blood tubes or other biofluid tubes, syringes, disposable equipment for preparing a venipuncture site), or processing a sample obtained from a subject (e.g., test tubes, slides). In yet other embodiments, the kit further contains instructions for use.

V. EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1. IL-10 Pathway Modulation for Improvement of Vaccine Efficacy Specific Aims The goal of this project is to demonstrate improvement of rhesus cytomegalovirus-based SIV vaccines (RhCMV/SIV) via IL-10 pathway modulation, e.g., to obtain significantly greater than 50% protective efficacy, more rapid immune responses, a greater concentration of such responses in $CD4^+$ T cells, or an altered cytokine environment permitting greater efficacy of induced responses.

We found that second-generation RhCMV/SIV vaccines lacking the viral IL-10 gene (RhCMVdIL10/SIV) protect non-human primate infants that have no prior RhCMV immunity, while first-generation (IL-10-intact) RhCMV/SIV vaccines do not. First-generation vaccines have been proven effective only in wild-type (wt) RhCMV-seropositive macaques having neutralizing antibodies to viral IL-10 generated in response to prior wtRhCMV infection.

The significance of this work is that it provides (i) new candidate HIV vaccines with greater efficacy in some or all segments of the population, (ii) a coherent, mechanistic explanation for previously obscure patterns of RhCMV/SIV vaccine protectiveness, (iii) immunologic insight into consequences of cellular and viral IL-10 (cIL-10 and vIL-10, respectively) pathway modulation, and (iv) new pharmacologic tools for control over IL-10 signaling.

Our preliminary data show that rhesus macaques infected by wild-type rhesus cytomegalovirus (wtRhCMV) mount immune responses to viral interleukin-10 (vIL-10), which in most cases leads to generation of neutralizing antibodies. RhCMV/SIV vaccine stringently protects ~50% of such wtRhCMV-seropositive but not wtRhCMV-seronegative monkeys against SIV challenge. A second-generation RhCMV/SIV vaccine lacking the viral IL-10 gene, however, does protect seronegative macaques. Furthermore, a series of experiments show that RhCMVdIL10/SIV vaccination is associated with reduced overall host IL-10 signaling, suggesting that complete inhibition of host IL-10 and/or viral IL-10 may lead to further efficacy gains for both vIL-10-containing and -deficient vaccines.

We will employ samples from animals vaccinated in such a way as to produce a range of viral IL-10 function from none (in animals receiving RhCMVdIL10), to intermediate (in wtRhCMV+ macaques with varying levels of neutralizing anti-vIL-10), to maximal (in wtRhCMV-macaques receiving RhCMV/SIV). We will also test RhCMVdIL10 efficacy in infants and adult animals, in the presence or absence of host IL-10 inhibition.

We hypothesize that RhCMV/SIV vaccination in the context of inhibited host IL-10 signaling will achieve more rapid immune responses, concentrated in CD4+ T cells with known anti-HIV activity (Emu et al., *J. Virol.* (2005) 79:14169-14178), in the context of an altered innate cytokine environment. Collectively these improvements will provide a more efficacious vaccine. Our specific aims are:

Aim 1. Define the transcriptomic and immunologic signatures of decreased IL-10 signaling using previously collected samples. Here we determine the true transcriptomic signature of host IL-10 signaling using samples from animals that received anti-IL-10 antibody. We then evaluate host responses to RhCMV/SIV vaccination in the presence of varying levels of viral IL-10 neutralization to determine how such neutralization affects (i) host IL-10 signaling, (ii) likelihood of generating a transcriptomic signature associated with protection, and (iii) vaccine efficacy.

Aim 2. Test the effect of cellular IL-10 inhibition on immune responses to and anti-SIV efficacy of viral IL-10-deficient vaccines in infant (wtRhCMV-seronegative) macaques. 50% of infant rhesus macaques were protected from SIV by a RhCMVdIL10/SIVgag vaccine lacking viral IL-10, but none were protected by first-generation RhCMV/SIVgag vaccine. Viral IL-10 encourages widespread cellular IL-10 expression by the host, resulting in higher levels of circulating cIL-10, blunted immune responses, and viral persistence. Since viral IL-10 deletion presumably interferes with the host IL-10 response, we reason that further interference (via administration of neutralizing anti-IL-10 antibody) will further augment vaccine efficacy. In this aim we administer RhCMVdIL10/SIVgag alone or in the presence of neutralizing anti-cIL-10 antibody, to determine if the latter regimen will alter the character of the resulting immune response and/or achieve >50% vaccine efficacy in infants.

Aim 3. Test the effect of cellular IL-10 inhibition on immune responses to and anti-SIV efficacy of viral IL-10-deficient vaccines in adult (wtRhCMV-seropositive) macaques. First-generation RhCMV/SIVgag vaccines (with intact vIL-10) were effective in ~50% of adult macaques previously infected with RhCMV and therefore having variable levels of anti-vIL-10 neutralizing antibodies. In this aim we will test if complete inhibition of viral and/or cellular IL-10 will achieve significantly greater efficacy. Adult macaques will be tested for improved immune responses and/or ability to stringently control SIV challenge after vaccination with RhCMVdIL10/SIVgag in the presence or absence of neutralizing anti-cIL-10 antibodies.

Together these studies will delineate the advantages of inhibited IL-10 signaling in RhCMV/SIV vaccine efficacy and point the way to new vaccine regimens that are effective for protection against infectious diseases and cancer.

Significance

First-Generation RhCMV/SIV Vaccines Protect 50% of Adult wtRhCMV+ Animals

Rhesus cytomegalovirus (RhCMV)-vectored vaccines were designed to work during a hypothetical window of vulnerability in early HIV/SIV infection (1-6) based on their ability to elicit high frequency, effector-differentiated, virus-specific T cells in sites of early viral replication (7-9). Indeed, the pattern of protection observed in approximately 50% of RhCMV/SIV vector-vaccinated rhesus macaques after intrarectal SIVmac239 challenge was not inconsistent with immunologic interception of the nascent SIV reservoir at the portal of viral entry, before systemic spread (7). Protected macaques manifested transient viremia at the onset of infection, followed by control of plasma SIV levels to below the level of detection, except for occasional plasma viral "blips" that waned over time, and at necropsy demonstrated only trace levels of tissue-associated SIV RNA and DNA using ultrasensitive assays.

A key feature of this work was the decision to vaccinate wtRhCMV-seropositive animals, due to the need to vaccinate an adult human population that is mostly cytomegalovirus infected and to the likely associated effects of pre-existing anti-vector immunity. Despite this pre-existing immunity, wtRhCMV-seropositive animals mount T cell responses to the vaccine antigen, which are assumed to form part of the mechanism of protection. However, it has now become clear that T cell responses are insufficient alone to explain protection—that some other pre-existing host characteristic or feature of the innate immune response is also required (10,11). In this context the nature of the host immune response to previous CMV infection becomes a key experimental variable, as CMV infection is known to have an important impact on most immune parameters (12,13).

Correlates of RhCMV/SIV-Mediated Protection

The mechanism of RhCMV/SIV-mediated protection is incompletely understood. An adaptive immune response to the vaccination antigen is required, because "empty" vaccines lacking antigen do not elicit immunity (14). Indeed, the intact vaccines elicit uniquely broad T cell responses with effector-memory cell phenotype and non-canonical MHC restriction (8,9,15); furthermore, no RhCMV/SIV candidate vaccine that fails to elicit Mamu-E restricted T cells has been shown to be protective. However, the frequency of such T cells within a vaccinated cohort does not quantitatively predict vaccine efficacy.

A transcriptomic study to identify new potential correlates of protection was previously undertaken (11). The results demonstrate a remarkable separation between protected and unprotected animals very soon after vaccination. The transcriptomic signature of protection derived from the analysis appears within one day of first vaccine administration and is strongest by three days after priming-pointing to an innate immune response that separates protected from unprotected animals. Such innate immune responses involve host detection of pathogen-associated molecular patterns and resulting production of cytokine and chemokines such as IP-10.

Analysis of genes making up the protective signature produces, as expected, a rich network of genes involved in innate immune function. Highly connected nodes in that network include CD80 (down-regulated), STAT1, IRF1, IRF7, TLR3, TLR4, and TLR7. The presence of CD80 in particular is interesting to us because we previously identified CD80 as among the most highly down-regulated molecules in wtRhCMV-seropositive vs. wtRhCMV-seronegative macaques (see, Preliminary Data and (13)). In addition, a sub-network was identified with many genes related to cytokine signaling and reported to be particularly rich in genes related to IL-10 function. Highly connected nodes in this network include TNF, JUN, MAP3K, and STAT3. Interestingly, CD14 is shown to be up-regulated in this network, and expansion of CD14+ cells is another effect of wtRhCMV infection. IL-10 receptor (IL10RA) is also shown as a peripheral member of the network, which is upregulated in protected animals. Receptor up-regulation is a possible homeostatic response to absence of a given cytokine.

RhCMV Carries a Viral IL-10 Gene that Restrains Host Immunity

It was discovered in 2000 that primate cytomegaloviruses encode and express an IL-10-like protein (16). Cellular IL-10 is a multifunctional cytokine that has suppressive effects on inflammation and cytokine production (17). Viral IL-10 proteins, like their host-protein counterparts, inhibit synthesis of cytokines by activated T cells, inhibit antigen-specific T-cell proliferation and induce proliferation and Ig secretion in activated B cells (18,19). It is well documented that infection with CMV can have immunosuppressive effects in vitro (20-22). Thus, it makes sense that possession of an IL-10-like gene would allow CMV to subvert antiviral cell-mediated immune responses in service of establishing a latent infection. Indeed, we now know that viral IL-10 alters the earliest host responses to viral antigens by dampening the response of innate effector cells to primary RhCMV infection (23). There is a commensurate reduction in the quality and quantity of RhCMV-specific adaptive immune responses.

Crucially, immune responses to RhCMV include varying levels of anti-vIL-10 neutralizing antibodies (see, Preliminary Data below). Interestingly, this information means that a first CMV infection is in most cases immunologically distinct from subsequent superinfections, which normally occur in the context of some level of viral IL-10 neutralization. Similarly, vaccination of wtRhCMV-seronegative macaques is essentially a first exposure whose immunologic consequences will be different to those of subsequent exposures.

Implications

*Cytomegalovirus*-based vaccines are promising HIV vaccine candidates but also present daunting immunologic complexity. Against the background of extraordinarily diverse and profound anti-wtRhCMV and anti-vector responses, defining the immune responses that separate protected from unprotected individuals will be difficult. In addition, the preclinical setting for RhCMV/SIV vaccine development financially impedes rapid, cost-effective testing of new vaccine candidates.

Given these difficulties, the identification of viral IL-10 as an impediment to vaccine efficacy in wtRhCMV-seronegative infant macaques is fortunate. Because wtRhCMV+ macaques make anti-vIL-10 antibodies, our discovery immediately suggests a key mechanism that is important to RhCMV/SIV vaccine efficacy generally. We invented methods and tools needed to investigate this possibility, from vIL-10-specific antibody assays to unique anti-IL-10 drugs to immunologically inactive vIL-10 immunogens.

Thus, our techniques represent a major advance in a complex field. This work will provide new mechanistic understanding, novel pharmacologic tools for control over vIL-10 and/or cIL-10 signaling, new candidate HIV vaccines with greater efficacy in some or all vaccine recipients, and promising directions for future research.

Innovation

Novel Improved RhCMV/SIV Vaccine

First-generation RhCMV/SIV vectors carry an intact, endogenous viral IL-10 gene, which is evolutionarily designed to suppress host immune responses (23-25). The discovery of this gene in primate cytomegaloviruses led to the study of its function and possible utility as a vaccine target (26,27). Based on this work, a second-generation RhCMV vector platform was created that has unique immunologic features and can protect wtRhCMV-seronegative infant macaques while first-generation vaccines to not (23). Further, the innate immune response to these RhCMVdIL10 vectors includes more consistent monocyte expansion and CD80 down-regulation-both features of the protective transcriptomic signature derived from RhCMV/SIV vaccines.

Alpha-Spending Design Allows Powered Testing of Improved RhCMV/SIV Vaccines in Non-Human Primates First-generation RhCMV/SIV vaccines protect ~50% of vaccinated monkeys. An HIV vaccine with 50% efficacy will yield tremendous worldwide benefit; nevertheless, a core goal in the field must be to improve this figure, yielding further human health benefit and potentially enabling eradication of HIV. Unfortunately, powered non-adaptive studies of modestly improved RhCMV/SIV vaccines are expensive, which will impede iteration and improvement. Achieving 80% power to detect a significant difference between vaccines with 50% and 70% efficacy requires 102 animals per group, or a total of 204 animals, for only two experimental arms. In contrast detecting the first 50% of efficacy (i.e., from 1% to 50% protection) requires only 13 animals per group.

To address this problem and enable parsimonious use of non-human primates, an "adaptive" study design using an alpha-spending approach was created. This approach creates adjusted (more stringent) alpha values for interim analyses so that the study can be terminated when significance has been achieved, without inflating the overall type I error rate. Thus, for example, we project the need to vaccinate and challenge 21 animals per group in Aim 2, but the study design allows for earlier termination after either of two earlier interim analyses (if the between-group difference is larger than expected and thus proven significant earlier). The design also allows continuing the study if needed until 33 animals per group are treated and full 80% power is achieved.

Approach

Preliminary Data

RhCMV/SIV Vaccines are not Reliably Effective in wtRhCMV-Seronegative Recipients In vaccine studies of wtRhCMV-seronegative newborn, infant, and adult animals, newborn and infant animals were vaccinated twice with RhCMV/SIVgag only and challenged with serial low-dose oral SIV; adult animals were vaccinated three times (subcutaneously and orally) with RhCMV/SIVgag, −SIVRetanef, and −SIV env and challenged with serial low-dose vaginal SIV. The resulting viral loads and adaptive immune responses are detailed in FIG. 1. We did not observe any instance of stringent viral control as previously described after vaccination of wtRhCMV+ macaques. That form of control manifested as rapid achievement of undetectable viral load within two weeks of first viremia, followed by undetectable viral load in at least 4 of 5 subsequent weeks (7). In the adult group there were instances of relative control over viremia, but these cases were infrequently observed and do not fit the profile previously described (FIG. 1A, rightmost plot). Robust Mamu-E-restricted T cell responses were observed, which exhibited a pattern of inhibition by antibodies and peptides that fit perfectly with the published description of such cells (FIG. 1B). Unexpectedly, RhCMV/SIV administration to these wtRhCMV-seronegative recipients generated clear antibody responses, in contrast to published results after vaccinating seropositive animals (FIG. 1C).

Protection of RhCMV-Seronegative Infant Macaques Against SIV Using RhCMVdIL10/SIVgag RhCMV and many other pathogens exploit the IL-10 pathway, as part of their infectious cycle, either through their own encoded IL-10 (rhcmvIL-10 for RhCMV) or manipulation of the cellular IL-10 signaling cascade. We previously demonstrated that rhcmvIL-10 alters the earliest host responses to viral antigens by dampening the magnitude and specificity of innate effector cells to primary RhCMV infection (36). Furthermore, there is a commensurate reduction in the quality and quantity of early and long-term, RhCMV-specific adaptive immune responses (36).

Figure 2:
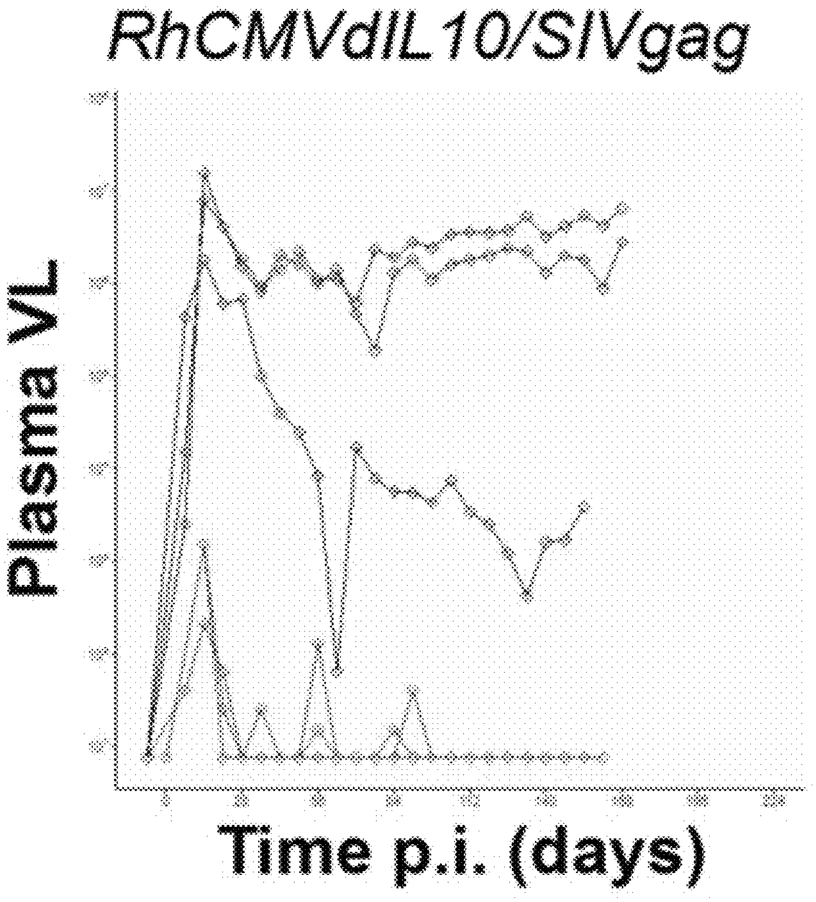
FIG. 2 shows that RhCMVdIL10/gag vaccine protected 3/6 wtRhCMV-seronegative infants. The challenge was serial, low-dose oral SIVmac251.

First-generation RhCMV/SIV vaccines include the rhcmvIL-10 gene, which might have a significant impact on the frequency of responding T cells. We therefore created new RhCMV vectors lacking the viral IL-10 gene using techniques we previously pioneered (35), along with new vIL-10 deleted vaccine vectors expressing SIV Gag. In a preliminary study RhCMVdIL10/SIVgag vaccine was administered to six RhCMV-seronegative infant macaques (~10 months of age), using a study protocol identical to that used for the first-generation vaccine, described above. This vaccine stringently protected 3/6 animals, whose viral load profile is identical to that previously observed in protected wtRhCMV+ macaques (FIG. 2).

wtRhCMV-Seropositive Macaques have Varying Levels of Neutralizing Antibodies to Viral IL-10

The clear protective efficacy of RhCMVdIL10/SIVgag vaccine on our first attempt, in a small cohort, stood in dramatic contrast to failure of the vaccine expressing viral IL-10 in 26 RhCMV-seropositive macaques of various ages (FIG. 1). This unexpected result indicates a central place for IL-10 signaling in vaccine efficacy. This indication is also broadly congruent with the conception of IL-10 as an immunosuppressive cytokine. Thus, the difference between apparent first-generation RhCMV/SIV vaccine efficacy in wtRhCMV+ and wtRhCMV-animals (i.e., (7) vs. FIG. 1) could be explained by different levels of effective vIL-10 activity.

The presence of anti-vIL-10 binding and neutralizing antibodies was assessed in cohorts of wtRhCMV-seropositive and wtRhCMV-seronegative macaques (33). The results show that every RhCMV+ macaque produces vIL-10 binding antibodies (FIG. 3A). An in vitro assay for anti-vIL-10 neutralizing antibody was also devised, in which macaque plasma is tested for the ability to relieve vIL-10-mediated suppression of LPS-induced IL-12. This assay demonstrates a range of vIL-10 neutralization in plasma of wtRhCMV+ macaques, from none to apparently complete (100%) neutralization in the context of the assay (FIG. 3B). Anti-IL-10 binding and neutralizing activities are correlated, as might be expected if the neutralizing antibodies are a subset of all anti-vIL-10 antibodies and have negligible activity when the overall titer is low (FIG. 3C). Of note, the in vitro assay measures presence of some level of neutralizing antibody in plasma, but the corresponding in vivo efficacy of circulating anti-vIL-10 is unknown. One can imagine either complete inhibition of vIL-10 activity due to relatively low protein expression in vivo, or very modest inhibition due to high local vIL-10 concentrations in tissues to which the antibody may have poor access.

Our dramatic in vivo experimental result (FIG. 2) and the anti-vIL-10 antibody assay results (FIG. 3) immediately suggest that first-generation RhCMV/SIV vaccines fail in wtRhCMV-seronegative recipients due to uninhibited action of viral IL-10. In addition, if the practical in vivo inhibitory activity of anti-vIL-10 neutralizing antibody varies among CMV+ vaccine recipients, then this variation could explain variable vaccine efficacy in those recipients.

Augmented T Cell Responses after RhCMVd10/SIV Vaccine Administration

Figure 4A:
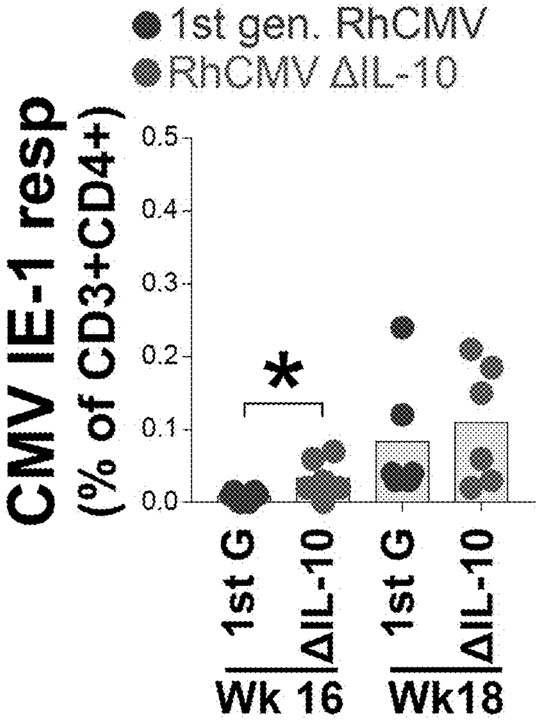
FIGS. 4A-4B show that viral IL-10-deleted RhCMV vaccines induce equivalent or greater T cell responses to those induced by first-generation vectors expressing viral IL-10.
Figure 4B:
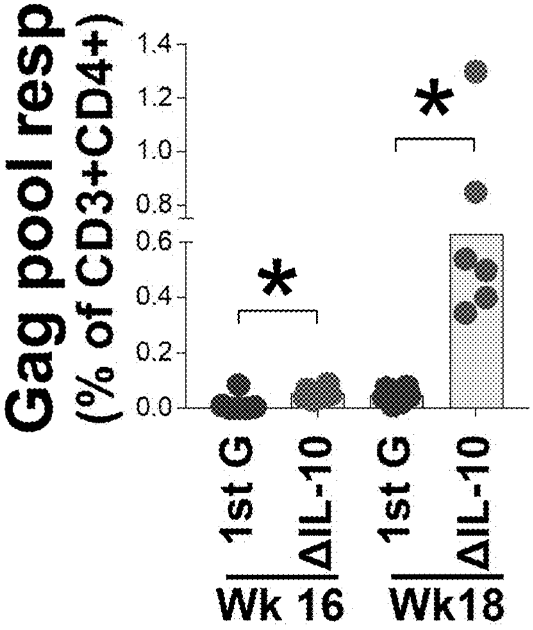

Administration of these vaccines to macaques resulted in significantly augmented cellular immune responses, as compared to vIL-10-intact vaccines (FIG. 4). We observed a significant increase in the frequency of RhCMV-specific and SIVgag-specific CD4+ T cells (FIGS. 4A and 4B).

Infant Macaques Protected by RhCMVdIL10/SIVgag Demonstrate CD80 Loss that is Congruent with the Protective Transcriptomic Signature As mentioned above, CD80 is among the most highly connected nodes in the transcriptomic signature of protection (11). CD80 is also dramatically and durably down-regulated after wild-type RhCMV infection (FIG. 5A). In a preliminary transcriptomic analysis of sorted T cells, NK cells, and APCs from wtRhCMV-seropositive macaques, in fact, CD80 expression is discontinuous, neatly separating the two groups on its own (FIGS. 5B and 5C). Of note, this similarity between the transcriptomic signature of protection and effects of wtRhCMV infection might suggest that the signature is reflective of vaccine vector replication and dissemination, but many features of the transcriptomic signature are not seen after wild-type infection. For example, IL-1beta transcription is increased in the blood of animals protected by RhCMV/SIV, but decreased after wild-type RhCMV infection (FIG. 5C, right panel).

Importantly, first-generation RhCMV/SIVgag vaccine fails to achieve CD80 down-regulation in wtRhCMV-seronegative recipients—but successful RhCMVdIL10/SIVgag vaccination does lead to CD80 loss (FIGS. 5D and 5E). CD80 expression levels at the time of SIV challenge are lower among protected animals (FIG. 5E), and this difference is a result of greater down-regulation after vaccination. These changes suggest that the mechanism of RhCMVdIL10/SIVgag-mediated protection of serognegative animals is similar to that of RhCMV/SIV-mediated protection of seropositive animals. The results also strongly suggest that RhCMV/SIVgag fails in seronegative recipients due to inability to provoke a necessary innate immune response.

Altered Immune Responses to RhCMVdIL10/SIVgag Reflect Reduced Host IL-10 Signaling IL-10 receptor is the only known receptor for cytomegalovirus IL-10 proteins and the proteins have in vitro activity that appears identical to that of host IL-10. Furthermore, wtRhCMV+ macaques demonstrate a small increase in circulating host IL-10 and a greater tendency to IL-10 production by unstimulated lymphocytes (33). Thus, increased IL-10 signaling seems to be a normal part of at least primary CMV infection, which is presumably beneficial to the virus. In addition, however, CMV infection seems to durably increase host IL-10 signaling over a period of years. Given the low abundance of CMV genomes, this secondary increase is likely due to greater overall production of host (i.e., non-viral) IL-10. Therefore, we hypothesize that viral IL-10 is detrimental to RhCMV/SIV vaccine efficacy due not only to its own activity, but also to consequent host IL-10 signaling.

Figure 6A:
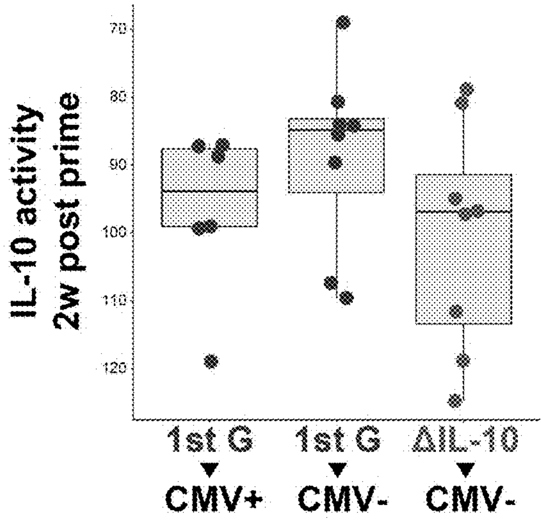
FIGS. 6A-6B show that RhCMVdIL10 vaccination is associated with lower host IL-10 activity after 1-2 weeks.
Figure 6B:
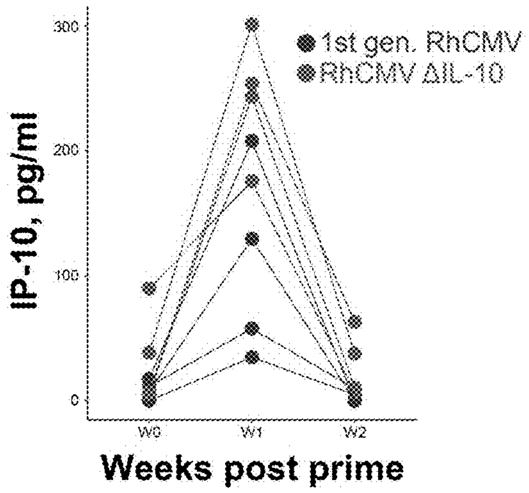
Figure 7:
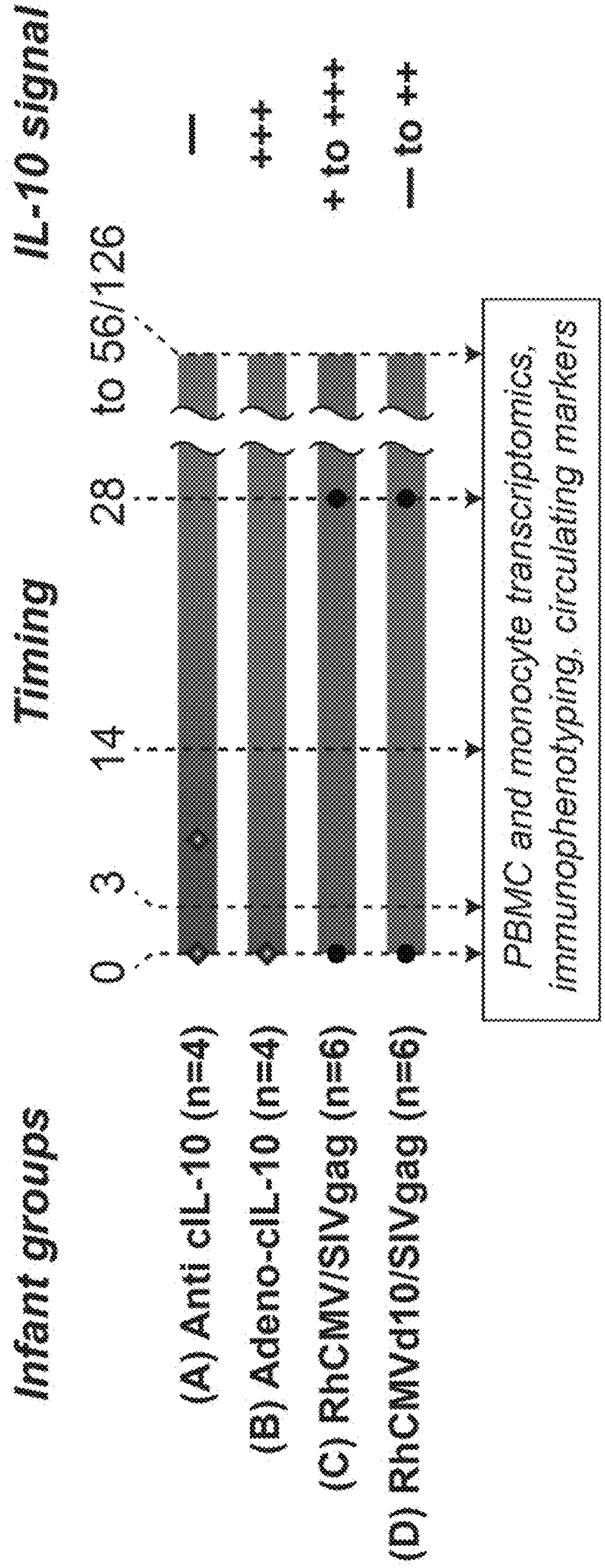
FIG. 7 shows a timeline of Aim 1 in Example 1.
Figure 8:
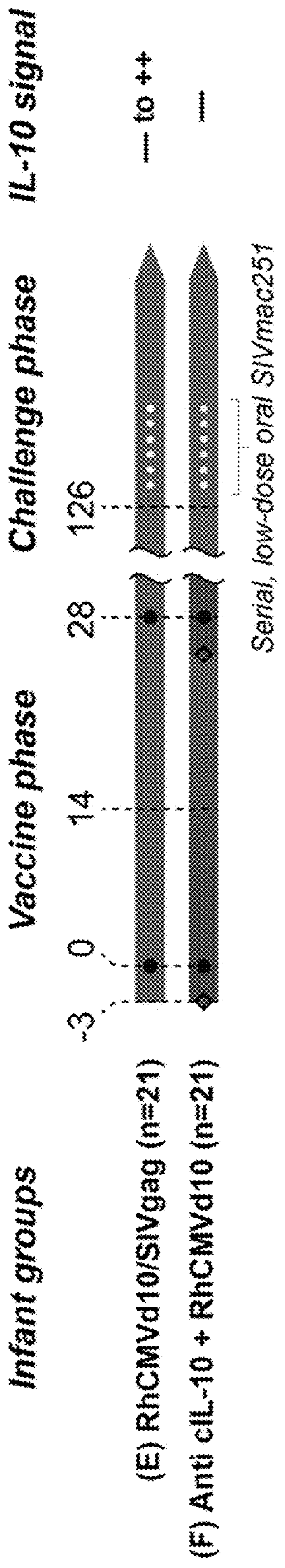
FIG. 8 shows a timeline of Aim 2 in Example 1.

This hypothesis predicts that host IL-10 signaling and downstream effects are more prominent after first-generation RhCMV/SIVgag vaccination than after RhCMVdIL10/SIV gag vaccination. To test this idea we performed two experiments. First, we used a bioassay to test the overall level of IL-10 activity in peripheral blood after RhCMV/SIVgag or RhCMVdIL10/SIVgag vaccination, revealing a trend to greater activity after administration of first-generation vaccines (FIG. 6A). Next, we performed a control experiment to identify other biomarkers that are associated with IL-10 signaling, with the intention of later testing these biomarkers in vaccinated monkeys. Four monkeys were administered anti-IL-10 neutralizing antibody or $10^{11}$ particles of an adenoviral vector expressing rhesus macaque IL-10. The adenoviral vector was confirmed before use to express bioactive IL-10 protein in our assays. Samples from these monkeys were collected before vaccination or 3, 14, and 28 days later. These samples were then assessed for host IL-10 bioactivity and a variety of other biomarkers (by Luminex), to determine if any are reflective of host IL-10 signaling or inhibition. IP-10 was shown to be the best (inverse) correlate. We then assayed plasma samples from RhCMV/SIV- or RhCMVdIL10/SIV-vaccinated animals and found that vaccination with viral IL-10-deleted RhCMVdIL10/SIVgag vaccine is associated with much greater induction of IP-10, strongly suggesting that these vectors are associated with lower overall IL-10 signaling in vivo (FIG. 6B).

Summary

Our preliminary data demonstrate that first-generation RhCMV/SIV vaccines are not reliably effective in wtRhCMV-seronegative macaques. Indeed, although seronegative macaques generate Mamu-E-restricted T cells, the immune responses otherwise appear fundamentally different, including robust antibody responses, failure to expand circulating CD14+ monocytes, and maintenance of CD80 expression. Viral IL-10-deleted RhCMVdIL10/SIVgag vaccine, however, generated robust T cell responses and protection from SIV challenge in 3/6 recipients. Furthermore, protected animals manifested expansion of CD14+ monocytes, CD80 down-regulation, and absent anti-p27 antibody production, all features reminiscent of vaccine-mediated protection as described previously. Several lines of evidence argue that altered immune responses to RhCMVdIL10/SIVgag reflect an overall lower level of host IL-10 signaling, e.g., increased IP-10 production and absent antibody responses.

These findings are important because they point to two targets for improvement of RhCMV-based vaccines: viral IL-10 and host IL-10. The former can be addressed by use of viral IL-10-deleted vector backbones. The latter might be addressed by use of anti-IL-10 neutralizing antibodies or IL-10-binding IL-10R1-Fc fusion protein, given systemically or locally, at the vaccine injection site. We used systemic anti-IL-10 neutralizing antibody in a first attempt.

It is also important to bear in mind that our results may be important for RhCMV-based vaccines targeting other diseases, such as tuberculosis and malaria (37). In a study that employed only RhCMV-seropositive adult macaques, it was demonstrated that RhCMV/TB vaccines can reduce the overall extent of Mtb infection and disease by 68%, as compared to that in unvaccinated controls. Infants and children, who are less often CMV seropositive, bear a large fraction of malarial and TB disease burdens. In areas of high malaria transmission, the majority of malarial disease, and particularly severe disease with rapid progression to death, occurs in young children without acquired immunity; tuberculosis is particularly lethal in children under five (see, Dodd et al., "The global burden of tuberculosis mortality in children: a mathematical modelling study", Lancet Global Health 5: PE898). Severe anemia, hypoglycemia, and cerebral malaria are features of severe malaria more commonly seen in children than in adults. Thus, good malaria and TB vaccine candidates should be effective in adult and infants regardless of CMV serostatus. Demonstration that viral and/or host IL-10 signaling impedes vaccine efficacy will therefore have great importance beyond the HIV vaccine field.

Research Design and Methods

Specific Aim 1: Define the Transcriptomic and Immunologic Signatures of Increased or Decreased IL-10 Signaling Using Previously Collected Samples Hypothesis RhCMV/SIV vaccine recipients manifest variable activation of cellular IL-10 signaling as assessed by transcriptomic and immunophenotypic analysis, with the least IL-10 signaling demonstrated in protected animals that received either (i) RhCMVdIL10/SIVgag vaccine or (ii) RhCMV/SIV vaccines in the context of robust pre-existing anti-viral IL-10 antibodies.

Rationale

Host responses to wild-type RhCMV infection and/or RhCMV-vectored vaccination can include an increased frequency of circulating CD14+ monocytes; a changed transcriptional program including reduced expression of co-stimulatory molecules such as CD80; increased expression of STAT3 and IL10RA; robust T cell responses; and suppressed antibody production to the vaccine antigen. Although many factors likely impinge on these outcomes, IL-10 is a common thread. By performing transcriptomics after providing either IL-10-neutralizing antibody or constitutive IL-10 expression, we have defined the polar extreme outcomes relevant to IL-10. We can then map the transcriptomes of vaccinated (and protected or unprotected) animals onto these extremes, allow us to infer the level of cIL-10 pathway activation in vivo.

Experimental Approach

In Aim 1, we use samples already in hand to define signatures of host IL-10 signaling. Samples from the following groups are available: (A) cIL-10 neutralizing Ab treated; (B) Ad-cIL-10 treated and proven to express supraphysiologic levels of circulating CIL-10; (C) RhCMV/SIVgag vaccinated; and (D) RhCMVdIL10/SIV gag vaccinated.

Rhesus Macaques Treated with Anti-IL-10 Neutralizing Antibody or with IL-10-Expressing Adenovirus wtRhCMV-seronegative macaques are obtained for these experiments by routine screening of young animals, 6-8 months of age, from a conventional colony. Seronegative macaques are then housed separately before rescreening about one month later to confirm seronegativity. We obtained anti-IL-10 neutralizing clone 1F11R1LALA from the NIH non-human primate reagent resource. This antibody was administered intravenously on days 0 and 7 at a dose of 30 mg/mL. No adverse effects were observed. Blood samples were collected on days 0, 3, 7, 14, 21, 28, and then every two weeks until day 56. RNA from blood and/or blood cells was preserved. Plasma from the remaining volume was separated and frozen in aliquots. PBMCs were then isolated and any cells not used immediately were cryopreserved. Neutralization of IL-10 in the treated animals was confirmed by loss of IL-10 bioactivity from plasma and by changes in other biomarkers such as IP-10.

Ad5-Cellular-IL-10 Expresses Rhesus Macaque IL-10 Under Control of the EF1Alpha Promoter The virus was created by preparation of an expression cassette, transfer to the AdEasy shuttle plasmid, recombination in BJ5183 bacterial cells supplied with the kit (39), and rescue of the virus in C7 cells (39,40). Expression of the proper protein was confirmed by mRNA analysis, ELISA, and bioassay for functional IL-10 protein. The vector was then grown to high titer, purified by CsCl equilibrium gradient centrifugation, dialyzed against buffered 5% sucrose, and titered. wtRhCMV-seronegative macaques were then injected intramuscularly with $3\times10^{11}$ particles. Increased circulating IL-10 was confirmed in the treated animals by bioassay.

Wild-Type RhCMV-Seronegative Macaques Vaccinated with First-Generation RhCMV/SIVgag or Viral-IL-10-Deleted RhCMVdIL10/SIVgag RhCMVdIL10/SIVgag was created by deletion of the first two exons of the viral UL111 gene. Both viruses were rescued in rhesus telomerized fibroblasts (telos), passaged on telos, purified by ultracentrifugation, and titered by plaque assay. $10^5$ pfu were injected subcutaneously on day 0 (prime) and $10^5$ pfu on day 28 (boost). Blood samples were collected as described above for groups A and B, except that biweekly sampling was continued until the first oral SIV challenge on day 126. The challenge protocol and schedule are described below as they will be used for groups E and F.

RNA sequencing will be performed initially for samples collected at 0, 3, 14, 28, and 56 or 126 days. Sequencing of mRNA from blood cells or purified monocytes will be performed using Illumina Tru-seq stranded mRNA libraries.

Immunophenotyping

Phenotypic and functional characteristics of isolated immune cells were assessed using a set of four flow cytometry panels used in our previously published work to examine antigen-presenting, B, T, and NK cells. The same panels have been used in our more recent analyses of the effects of wild-type RhCMV infection on the macaque immune system (see Preliminary Data and (13)), providing a wealth of comparative data. Antibodies to be used in these panels at optimal concentrations include those reactive to CD3, CD4, CD8, CD95, CD28, CCR5, CCR7, Ki-67, PD-1, CD127, CD25, CD196, CD194, CD123, HLA-DR, CD14, CD16, CD38, CD83, CD80, CD86, CD20, CD21, CD27, CD11b, CD11c, FcεRIγ, IgD, IgM, FOXP3, TCRγδ, CD56, Mamu-E, NKG2A, Eomes, and T-bet.

Plasma Biomarkers

A panel of plasma biomarkers related to inflammation, known effects of IL-10, or differences previously noted between wtRhCMV+ and wtRhCMV-animals will be assessed by Luminex or ELISA. These include cellular IL-10, CXCL13, IL-1beta, IL-4, IL-8, IL-17A, IL-21, IP-10, M-CSF, MCP-1, prostaglandin E2, and TNF-alpha.

Viral IL-10 neutralizing antibody activity will be measured in samples as described in (31). Briefly, PBMCs are stimulated with LPS in the presence of RhCMV vIL-10, which suppresses IL-12 production. Plasma containing viral IL-10 neutralizing antibodies relieves this suppression and restores IL-12.

Interpretation of Data

We have defined and will refine a feature set (messages or biomarkers) whose expression is influenced by cellular IL-10 signaling. Expression of genes in the set varies between experimental groups (e.g., protected vs. unprotected or RhCMV/SIV vs. RhCMVdIL10/SIV) and quantitative examination of genes in the set will reveal the lowest IL-10 signaling in protected animals receiving the RhCMVdIL10/SIVgag vaccine. The analysis for Aim 1 will proceed stepwise. First, the IL-10-regulated feature set will be defined by differential expression analysis of the biomarker information (RNAseq, cytometry, and plasma analytes) collected from groups A and B. Based on the preliminary cytometric and biomarker data, e.g., in FIG. 6B, we are confident that a differential feature set can be defined. This feature set will also suggest a quantitative score for assessing IL-10 signaling in the other experimental groups, which is defined based on multivariate distances to the centroids of groups A and B. Second, we will test for enrichment of IL-10-regulated features among animals in groups C and D. Most importantly, we will test enrichment of IL-10-related changes in (i) first-generation RhCMV/SIVgag vaccine vs. RhCMVdIL10/SIVgag vaccine recipients and (ii) protected vs. unprotected vaccine recipients.

Statistical Analysis

To define the IL-10 signaling-associated feature set, each dataset is subjected to a variance-stabilizing transformation and then differentially analyzed using the limma pipeline for calculating moderated t-statistics and p values by empirical Bayes. RNA-seq data are subjected before linear modeling to variance modeling at the observational level (limma-voom). Adjusted p values are then calculated for each dataset and IL-10-associated features selected based on an adjusted p value $<0.02$. For experimental groups in which we wish to assess IL-10 signaling, changes in the IL-10 feature set are assessed via rotation gene set testing (roast function of limma R package) with feature weights set to log-fold or other transformed changes seen in the control experiment. Important features are identified when we see significance of these tests between groups C and D (first-generation vs. delta IL-10 vaccines) or between protected and unprotected animals.

Quantitative IL-10-signaling scores can be devised as a ratio of multivariate distances (Euclidean distance of scaled data) to the IL-10-inhibited centroid (a) vs. the Ad5-IL-10 centroid (b), i.e., a/(a+b).

Summary

Our data point to viral IL-10 activity as an impediment to vaccine-mediated protection—but also show that host IL-10 is important, as well, and that its inhibition further improves immune responses to RhCMV/SIV vaccines.

Specific Aim 2: Test if Cellular IL-10 Inhibition Augments Vaccine Efficacy in Infant (RhCMV-Negative) Macaques Hypothesis Inhibition of cellular IL-10 signaling post RhCMVdIL10/SIVgag vaccination will provide an increased frequency of (i) the protective transcriptomic signature, (ii) rapid induction of protective T cell responses, (iii) an altered innate cytokine environment that is important for protection and also reflected in the protective transcriptomic signature (item i), and (iv) vaccine-mediated protection.

Rationale

RhCMV/SIVgag vaccine is ineffective among RhCMV-seronegative infant macaques unless the viral IL-10 gene is removed. The only known function of viral IL-10 protein is to bind host IL-10 receptors; downstream signaling and functional consequences appear identical. Therefore, barring a previously unsuspected function of vIL-10, the data show clearly that IL-10 signaling is detrimental to RhCMV/SIV vaccine efficacy. If host (i.e., cellular) IL-10 also contributes detrimental signaling, then inhibition of cellular IL-10 will further augment vaccine efficacy. Just as importantly, joint inhibition of signaling due to host IL-10 and viral IL-10 proteins provides more rapid and effective T cell responses as well as an improved innate immune response, reflected in production of cytokines by innate immune cells. Rapid, improved immune responses to vaccination are important for protection of infants, whose risk of infection is highest while breastfeeding, and for protection of all previously CMV-uninfected individuals.

Experimental Approach

Wild-type RhCMV-seronegative infant rhesus macaques (~10 months) will receive RhCMVd10/SIVgag vaccine alone (Group E) or preceded by neutralizing anti-macaque IL-10 antibody (Group F; 30 mg/mL intravenously as in Aim 1, Group A). Two vaccine doses will be given at 0 and 4 weeks and low-dose oral challenges will begin 18 weeks after vaccination. Group F animals will receive anti-IL-10 antibody three days before prime and again three days before boost. The primary outcome is protection against SIV infection in the mode previously described and seen also in our previous experiment (FIG. 2): rapid control within 2 weeks of initial peripheral viral load, followed by durable control to below the level of detection of virus in blood. We are additionally interested in the rapidity of immune response as well as many measures of the innate and adaptive immune responses to vaccine and challenge virus.

This is an adaptive study design so the numbers shown are estimates. Twelve new infants will be assigned at the beginning of each year and an interim analysis performed at the end of each year. To avoid type I error inflation, the alpha value for each interim analysis will be set according to a Lan-DeMets alpha spending function with Pocock-type boundaries. If a significant difference between groups is observed then this experiment will conclude and work on Aim 3 will begin.

Rhesus Macaques, Vaccination, and Sampling

RhCMV-seronegative infant macaques are obtained by screening as described in Aim 1 and vaccinated according to the same established protocol. The pre-challenge blood sampling schedule is as described above. Challenges are then performed every two weeks as described below and blood samples are collected each alternate week to test for infection. After viremia is detected, blood is drawn weekly to a maximum of 12 mL/kg/month. Lymph nodes (LN) are collected before priming vaccination, 8 weeks after priming, and 18 weeks after priming (before SIV challenge).

Serial, Low-Dose Oral Challenges

Our previous vaccination and challenge experiments (see, Preliminary Data) have confirmed that our oral challenge schedule infects only 25% of animals on each consecutive week. The oral challenges given are 2K, 2K, 2K, 4K, 4K, 4K, 8K, 8K, 8K, 40K, 40K, 100K, and 100K $TCID_{50}$. In our previous experiments all animals were infected before the end of this series.

Viral Nucleic Acid Analysis in Plasma and PBMCs

Plasma viral RNA will be evaluated primarily using quantitative RT-PCR (Quantitative Molecular Diagnostics Core, Frederick National Laboratory). The extracted RNA will be run in 12 replicates in a 384-well format, which enhances the reliability of positive determinations and lowers the detection threshold. The lower limit of detection in a 100 microliter sample is 16 copies/mL.

An ultrasensitive assay is also available, which can be used, e.g., when viral clearance is suspected. This approach uses a hybrid real-time and digital PCR technique to allow input of a large amount of test sample in the first round of testing, critical for detection of rare sequences in a large specimen amount. Most significant is the ability to quantify very low target levels, on the order of 1 copy per number of test aliquots (i.e., one copy per $10^7$ to $10^8$ cells), with good reliability.

RNA sequencing will be performed and plasma biomarkers assayed as described in Aim 1, and at the same time points.

Host immune phenotypes, including T cell subpopulations, activation, exhaustion, and homing markers (e.g., CXCR5 and CCR7) will be followed by flow cytometry using standard techniques. For assessment of antigen-specific T cell responses, assay wells containing up to 1M PBMCs or LNMCs will be stimulated with vehicle (negative control for DMSO toxicity), overlapping SIV peptides, specific peptides with known Mamu-E restriction (e.g., Gag69, Gag18, or Gag120), or PMA/ionomycin (positive control). All wells will also receive anti-CD28 and anti-CD49d at a concentration of 2 μg/mL. Inhibitors such as VL9 peptide or anti-HLA-antibodies are applied one hour before stimulation begins and added again with the peptide stimulus. GolgiPlug (BD Biosciences) will be added one hour after the start of incubation. Five hours later, samples will be harvested by centrifugation, fixed, permeabilized, and stained using fixable live-dead stain as well as antibodies reactive to CD3, CD4, CD8, CD27, CD45RA, IL-2, IL-17, IFN-γ, and TNF-α. The fraction of cytokine-secreting CD4+ and CD8+ T cells will be determined by flow cytometry on a BD Fortessa.

Co-Culture Assay for Replication-Competent Virus

In cases of suspected viral clearance, graded numbers of mononuclear cells (i.e., $10^3$, $10^4$, or $10^5$ cells) will be tested for the presence of replication-competent virus by cultivation with $10^5$ CEMx174 cells in 24-well plates, followed by flow cytometric analysis of intracellular SIV-Gag p27 expression. Cocultured cells are harvested and analyzed at days 13-36.

CD8+ T Cell Depletion of Protected Macaques

A key feature of long-term RhCMV vector-associated SIV control is its insensitivity to CD8+ lymphocyte depletion. To test if this feature is noted after RhCMVdIL10/gag vaccine-mediated control, two to four controlling macaques will be treated with cM-T807 monoclonal antibody (10, 5, 5, and 5 mg per kg body weight on days 0, 3, 7, and 10) and the effect on viremia observed.

Interpretation of Data

Our hypothesis predicts more rapid immune responses and greater vaccine efficacy in group F (anti-cIL-10 treated) than group E (control). Our hypothesis also predicts that inhibition of cellular IL-10 signaling will increase the frequency with which the transcriptomic signature of protection is observed. Our supposition is that viral and host IL-10 signaling are detrimental to establishment of this signature, which itself favors protection through influence on either adaptive immune responses to the vaccine or innate conditions that influence early viral replication.

Many other outcomes are of interest. For our overarching hypothesis, we wish to know if successful vaccination is associated with a reduction in IL-10 signaling, as defined by the feature set assembled in Aim 1. We can assess changes in this IL-10 feature set between protected and unprotected animals, or association with other correlates of protection previously defined (e.g., reduced CD80 expression).

Statistical Analysis

Fisher's Exact Test will be used to statistically compare proportions of macaques that achieve functional cure (as defined above) in the two groups. For power calculations, we assume that inhibition of host IL-10 will improve vaccine efficacy from 50% to 85%, i.e., a lesser impact than deletion of the viral IL-10 gene. At five interim analyses with adjusted alpha values set using a Lan-DeMets spending function with Pocock-type boundaries and information fractions reflecting the number of animals challenged after every year, the power of Fisher's Exact Test for detecting a difference between groups in Years 1-5 is 3%, 29%, 52%, 72%, and 83%, respectively. We therefore predict that the experiment of Aim 2 will conclude after Year 3, but if necessary then the experiment will be continued into Years 4-5.

Our hypothesis also predicts that inhibition of cellular IL-10 signaling in group F will lead to transcriptomic changes including (i) reduction in the IL-10-associated features from Aim 1 and (ii) increased frequency of protection-associated transcripts. These predictions will be tested using the analysis framework outlined above. In brief, enrichment in animals receiving anti-IL-10 vs. controls (group F vs. E), or in protected vs. unprotected macaques, will be tested by rotational gene set testing. If these tests are significant then quantitative scores as defined in Aim 1 can be used in generalized linear models (GLMs) for further exploration. For example, GLMs with a logit link could be used to assess a quantitative relationship between restrained IL-10 signaling after vaccination and eventual protection.

Of note, we expect that among the 42 animals vaccinated in this experiment, at least 21 will be protected from SIV. If this prediction is correct then we will have sufficient power to define new transcriptomic and immunologic signatures of RhCMVdIL10/SIVgag-mediated protection. Because our analysis techniques leverage sophisticated linear modeling, all 42 animals can be modeled together to provide greatest power for identification of protection-associated features. This protection-associated signature can be entered into the analysis pipeline mentioned above and can also be compared with signatures previously defined.

Possible Pitfalls and Alternative Approaches

We also have the option of an alternative approach to IL-10 neutralization: a IL10R1-Fc fusion. This protein binds to and neutralizes host viral IL-10 proteins with nanomolar affinities. The molecule is smaller than a neutralizing antibody and thus may achieve superior tissue penetration. We are testing the pharmacokinetics and pharmacodynamics of this reagent now and will consider using it instead of antibody, if a significant advantage is observed, e.g., in intensity or duration of effect. Possibly this protein is a superior pharmacologic tool for control over IL-10 signaling, which could be useful as an adjuvant for this and possibly other vaccines.

Specific Aim 3: Test if Cellular and/or Viral IL-10 Inhibition Augment Vaccine Efficacy in Adult (RhCMV-Positive) Macaques Hypothesis Inhibition of viral and cellular IL-10 signaling post RhCMV-based SIV vaccination will cooperatively increase frequency of (i) the protective transcriptomic and immunologic signature, (ii) rapid induction of protective T cell responses, (iii) an altered innate cytokine environment that is important for protection and also reflected in the protective transcriptomic signature (item i), and (iv) vaccine-mediated protection.

Rationale

RhCMV/SIV vaccines demonstrate a curious pattern of protective efficacy in 50% of adult (RhCMV seropositive) animals. Successful vaccination requires the vaccine insert, demonstrating that protection is mediated by an adaptive immune response, but is also associated to an extraordinary degree with specific transcriptomic and immune responses seen as early as one day after vaccination, demonstrating the contribution of an innate response. This innate response is related to that seen after wild-type RhCMV infection. The most important questions about these vaccines as they transition to human clinical trials are (i) if humans will generate similar protective innate and adaptive immune responses to those seen in monkeys, and if so (ii) how to rapidly protect infants and adults so that they are protected from exposures soon after vaccination, (iii) how to protect all segments of the human population, including those not previously infected with wild-type CMV, and (iii) how to increase efficacy of the vaccine to over 50%.

Our preliminary experiments yielded an important clue: RhCMV-seronegative vaccine recipients are not protected unless the viral IL-10 gene is deleted. RhCMVdIL10 but not intact RhCMV/SIV vaccines generated innate and adaptive immune responses similar to those seen in RhCMV seropositive monkeys; furthermore, the responses were protective against SIV challenge. This information points to IL-10 signaling as an important determinant of the required innate response that is lacking among macaques not protected by RhCMV/SIV vaccines. Furthermore, we have shown in previous experiments that IL-10 signaling in RhCMV infection derives from two sources: viral IL-10 and host (i.e., cellular) IL-10. We reason that inhibition of either or both of these IL-10 sources will augment RhCMV/SIV vaccine efficacy in RhCMV-seropositive adult macaques.

Experimental Approach

Two groups of adult animals will be vaccinated exactly as described in Aim 2 and challenged at the same time point, 18 weeks after priming vaccination. Challenges will be administered intrarectally.

Rhesus Macaques and Vaccination wtRhCMV-seropositive macaques, 3.25-6 years old, will be assigned to these studies. The vaccination protocol will be exactly as described above for Aim 2.

Serial, low-dose intrarectal challenges will be performed with SIVmac239 according to a published protocol (7). 300 focus-forming units of virus are given weekly for the first eight challenges and then, if necessary, five additional weekly challenges are performed at 1,000 focus-forming units. Viremia is tested weekly, with challenge being discontinued the week after detection of >30 copies/mL.

Virologic and immunologic follow up to vaccination and SIV challenge will be carried out as described above. In the vaccine phase, adaptive immune responses will be followed along with transcriptomics, immunophenotypes, and plasma biomarkers. In the challenge phase, viral load and immune response assays will be emphasized but stringent tests of viral clearance will also be performed.

Interpretation of Data

Figure 9:
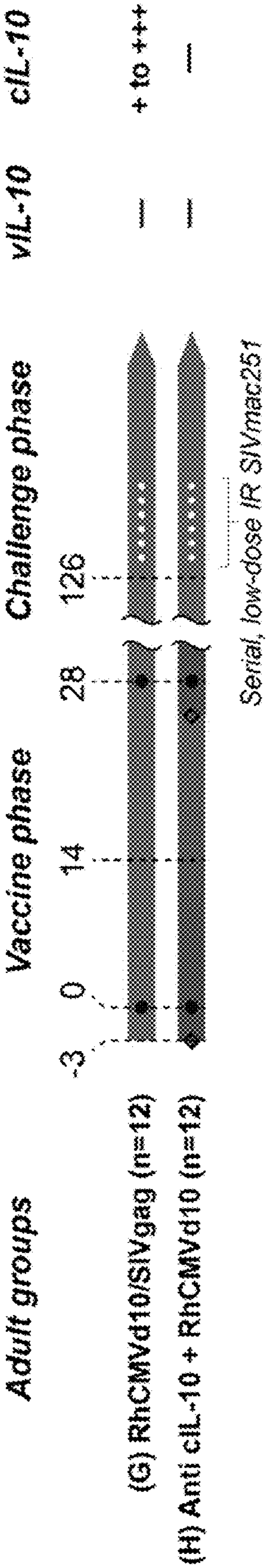
FIG. 9 shows a timeline of Aim 3 in Example 1.

Our hypothesis predicts that inhibition of viral and cellular IL-10 signaling post RhCMV-based SIV vaccination will yield vaccine efficacy that is significantly greater than 50%. Specifically, we expect that vaccine efficacy in both groups (G and H from FIG. 9) will exceed 50%. We may also observe a preliminary indication that efficacy in group H exceeds that in group G, but will not observe a significant difference unless efficacy in Group G is unexpectedly low.

Other outcomes of interest include all those mentioned in the previous aim, particularly correlations between protection, reduced IL-10 signaling as assessed by the IL-10-associated features defined in Aim 1, and previously observed correlates such as low CD80 expression. We wish to know if these characteristics are invariably correlated with each other or if the relationship sometimes fails.

We will additionally be able to perform a number of interesting comparisons of adults and infants, whether wild-type RhCMV-seropositive or RhCMV-seronegative, by comparing data from this aim to those from Aim 2 or from previous experiments. For example, anti-cIL-10 may have a different impact in older animals. We have shown in unpublished work that cIL-10 levels in plasma decline with age, so one can imagine a lesser overall effect of anti-cIL-10. Finally, the overall level of vaccine efficacy may be different in adults as compared to infants, e.g., in groups E vs. G or F vs. H.

Statistical Analysis

Exact binomial tests will be used to compare the fraction of protected animals in each group to the previously published value of 50%. The two groups in this Aim will be assigned animals sequentially. That is, after Aim 2 concludes then all 12 animals the following year will be assigned to Group G. For power calculations we assume that anti-viral IL-10 antibodies were the primary determinant of protection in previous published work and thus that a high fraction of animals vaccinated with RhCMVdIL10/SIV will be protected (85%). Assuming that 12 animals are assigned in Year 4 and 12 in Year 5 and using a Lan-DeMets spending function with Pocock-type boundaries, the power of an exact binomial test for detecting efficacy over 50% in Group G in Years 4 and 5 are 45% and 94%, respectively.

If efficacy in Group G is found to exceed 50% after Year 4, then the 12 animals assigned in Year 5 will be assigned to Group H. Assuming efficacy of 90% for the combined regimen in adult macaques, the power to detect efficacy exceeding 50% using only 12 animals will be 89%.

Timeline 60 additional animals will be used in five years, with 12 assigned each year. In Years 1-3, we anticipate that a total of 36 infants will be assigned to Groups E and F. Each year the animals will be assigned, vaccinated, challenged, and protection assessed so that interim analysis can occur before the following year. In Year 4 we anticipate assigning 12 three-to-six-year-old animals to Group G. In Year 5 we anticipate assigning 12 three-to-six-year-old animals to group H.

REFERENCES

1. Haase, A. T., Early events in sexual transmission of HIV and SIV and opportunities for interventions. *Annu Rev Med,* 2011. 62: p. 127-39.
2. Lifson, J. D., J. L. Rossio, R. Arnaout, L. Li, T. L. Parks, D. K. Schneider, R. F. Kiser, V. J. Coalter, et al., *Containment of simian immunodeficiency virus infection: cellular immune responses and protection from rechallenge following transient postinoculation antiretroviral treatment.* J Virol, 2000. 74 (6): p. 2584-93.
3. Saez-Cirion, A., C. Bacchus, L. Hocqueloux, V. Avettand-Fenoel, I. Girault, C. Lecuroux, V. Potard, P. Versmisse, et al., *Post*-Treatment HIV-1 *Controllers with a Long-Term Virological Remission after the Interruption of Early Initiated Antiretroviral Therapy ANRS VISCONTI Study. PLOS Pathog,* 2013. 9 (3): p. e1003211.
4. Van Rompay, K. K., L. Durand-Gasselin, L. L. Brignolo, A. S. Ray, K. Abel, T. Cihlar, A. Spinner, C. Jerome, et al., *Chronic administration of tenofovir to rhesus macaques from infancy through adulthood and pregnancy: summary of pharmacokinetics and biological and virological effects.* Antimicrobial agents and chemotherapy, 2008. 52 (9): p. 3144-60.
5. Van Rompay, K. K., M. B. McChesney, N. L. Aguirre, K. A. Schmidt, N. Bischofberger, and M. L. Marthas, *Two*

*low doses of tenofovir protect newborn macaques against oral simian immunodeficiency virus infection*. J Infect Dis, 2001. 184 (4): p. 429-38.

6. Van Rompay, K. K., K. A. Trott, K. Jayashankar, Y. Geng, C. C. LaBranche, J. A. Johnson, G. Landucci, J. Lipscomb, et al., *Prolonged tenofovir treatment of macaques infected with K65R reverse transcriptase mutants of SIV results in the development of antiviral immune responses that control virus replication after drug withdrawal*. Retrovirology, 2012. 9: p. 57.
7. Hansen, S. G., J. C. Ford, M. S. Lewis, A. B. Ventura, C. M. Hughes, L. Coyne-Johnson, N. Whizin, K. Oswald, et al., *Profound early control of highly pathogenic SIV by an effector memory T-cell vaccine*. Nature, 2011. 473 (7348): p. 523-7.
8. Hansen, S. G., J. B. Sacha, C. M. Hughes, J. C. Ford, B. J. Burwitz, I. Scholz, R. M. Gilbride, M. S. Lewis, et al., *Cytomegalovirus vectors violate CD*8+ *T cell epitope recognition paradigms*. Science, 2013. 340 (6135): p. 1237874.
9. Hansen, S. G., C. Vieville, N. Whizin, L. Coyne-Johnson, D. C. Siess, D. D. Drummond, A. W. Legasse, M. K. Axthelm, et al., *Effector memory T cell responses are associated with protection of rhesus monkeys from mucosal simian immunodeficiency virus challenge*. Nat Med, 2009. 15 (3): p. 293-9.
10. Barouch, D. H. and L. J. Picker, *Consortia for Innovative AIDS Research in Nonhuman Primates*. 2016, NIH/NIAID: Beth Israel Deaconess Medical Center.
11. Gale, M., Jr., *Protective Gene Expression Signature in Response to RhCMV/SIV Vaccine Vectors*, in *Conference on Retroviruses and Opportunistic Infections*. 2018: Boston, MA, USA.
12. Brodin, P., V. Jojic, T. Gao, S. Bhattacharya, C. J. Angel, D. Furman, S. Shen-Orr, C. L. Dekker, et al., *Variation in the human immune system is largely driven by non-heritable influences*. Cell, 2015. 160 (1-2): p. 37-47.
13. Santos Rocha, C., L. A. Hirao, M. G. Weber, G. Mendez-Lagares, W. L. W. Chang, G. Jiang, J. D. Deere, E. E. Sparger, et al., *Subclinical cytomegalovirus infection associates with altered host immunity, gut microbiota and vaccine responses*. J Virol, 2018.
14. Hansen, S. G., M. Piatak, Jr., A. B. Ventura, C. M. Hughes, R. M. Gilbride, J. C. Ford, K. Oswald, R. Shoemaker, et al., *Immune clearance of highly pathogenic SIV infection*. Nature, 2013. 502 (7469): p. 100-4.
15. Hansen, S. G., H. L. Wu, B. J. Burwitz, C. M. Hughes, K. B. Hammond, A. B. Ventura, J. S. Reed, R. M. Gilbride, et al., *Broadly targeted CD*8(+) *T cell responses restricted by major histocompatibility complex E*. Science, 2016. 351 (6274): p. 714-20.
16. Lockridge, K. M., S. S. Zhou, R. H. Kravitz, J. L. Johnson, E. T. Sawai, E. L. Blewett, and P. A. Barry, *Primate cytomegaloviruses encode and express an IL*-10-*like protein*. Virology, 2000. 268 (2): p. 272-80.
17. Fiorentino, D. F., M. W. Bond, and T. R. Mosmann, *Two types of mouse T helper cell. IV. Th*2 *clones secrete a factor that inhibits cytokine production by Th*1 *clones*. J Exp Med, 1989. 170 (6): p. 2081-95.
18. de Waal Malefyt, R., J. Haanen, H. Spits, M. G. Roncarolo, A. the Velde, C. Figdor, K. Johnson, R. Kastelein, et al., *Interleukin* 10 (IL-10) *and viral IL*-10 *strongly reduce antigen-specific human T cell proliferation by diminishing the antigen-presenting capacity of monocytes via downregulation of class II major histocompatibility complex expression. J Exp Med,* 1991. 174 (4): p. 915-24.
19. Rousset, F., E. Garcia, T. Defrance, C. Peronne, N. Vezzio, D. H. Hsu, R. Kastelein, K. W. Moore, and J. Banchereau, *Interleukin* 10 *is a potent growth and differentiation factor for activated human B lymphocytes*. Proc Natl Acad Sci USA, 1992. 89 (5): p. 1890-3.
20. Einhorn, L. and A. Ost, *Cytomegalovirus infection of human blood cells*. J Infect Dis, 1984. 149 (2): p. 207-14.
21. Schrier, R. D. and M. B. Oldstone, *Recent clinical isolates of cytomegalovirus suppress human cytomegalovirus-specific human leukocyte antigen-restricted cytotoxic T-lymphocyte activity*. J Virol, 1986. 59 (1): p. 127-31.
22. Schrier, R. D., G. P. Rice, and M. B. Oldstone, *Suppression of natural killer cell activity and T cell proliferation by fresh isolates of human cytomegalovirus*. J Infect Dis, 1986. 153 (6): p. 1084-91.
23. Chang, W. L. and P. A. Barry, *Attenuation of innate immunity by cytomegalovirus IL*-10 *establishes a long-term deficit of adaptive antiviral immunity*. Proc Natl Acad Sci USA, 2010. 107(52): p. 22647-52.
24. Slobedman, B., P. A. Barry, J. V. Spencer, S. Avdic, and A. Abendroth, *Virus-encoded homologs of cellular interleukin*-10 *and their control of host immune function*. J Virol, 2009. 83 (19): p. 9618-29.
25. Spencer, J. V., K. M. Lockridge, P. A. Barry, G. Lin, M. Tsang, M. E. Penfold, and T. J. Schall, *Potent immunosuppressive activities of cytomegalovirus-encoded interleukin*-10. J Virol, 2002. 76 (3): p. 1285-92.
26. Logsdon, N. J., M. K. Eberhardt, C. E. Allen, P. A. Barry, and M. R. Walter, *Design and analysis of rhesus cytomegalovirus IL*-10 *mutants as a model for novel vaccines against human cytomegalovirus*. PLOS One, 2011. 6 (11): p. e28127.
27. Yue, Y., A. Kaur, M. K. Eberhardt, N. Kassis, S. S. Zhou, A. F. Tarantal, and P. A. Barry, *Immunogenicity and protective efficacy of DNA vaccines expressing rhesus cytomegalovirus glycoprotein B, phosphoprotein* 65-2, *and viral interleukin*-10 *in rhesus macaques*. J Virol, 2007. 81 (3): p. 1095-109.
28. Ardeshir, A., N. R. Narayan, G. Mendez-Lagares, D. Lu, M. Rauch, Y. Huang, K. K. Van Rompay, S. V. Lynch, and D. J. Hartigan-O'Connor, *Breast-fed and bottle-fed infant rhesus macaques develop distinct gut microbiotas and immune systems*. Sci Transl Med, 2014. 6 (252): p. 252ra120.
29. Hartigan-O'Connor, D., C. J. Kirk, R. Crawford, J. J. Mul√©, and J. S. Chamberlain, Immune evasion by muscle-specific gene expression in dystrophic muscle. Molecular therapy, 2001. 4 (6): p. 525-33.
30. Hartigan-O'Connor, D. J., M. A. Jacobson, Q. X. Tan, and E. Sinclair, *Development of cytomegalovirus* (*CMV*) *immune recovery uveitis is associated with Th*17 *cell depletion and poor systemic CMV-specific T cell responses*. Clin Infect Dis, 2011. 52 (3): p. 409-17.
31. Eberhardt, M. K., W. L. Chang, N. J. Logsdon, Y. Yue, M. R. Walter, and P. A. Barry, *Host immune responses to a viral immune modulating protein: immunogenicity of viral interleukin*-10 *in rhesus cytomegalovirus-infected rhesus macaques*. PLOS One, 2012. 7 (5): p. e37931.
32. Eberhardt, M. K., A. Deshpande, W. L. Chang, S. W. Barthold, M. R. Walter, and P. A. Barry, *Vaccination against a virus-encoded cytokine significantly restricts viral challenge*. J Virol, 2013. 87 (21): p. 11323-31.
33. Eberhardt, M. K., A. Deshpande, J. Fike, R. Short, K. A. Schmidt, S. A. Blozis, M. R. Walter, and P. A. Barry, *Exploitation of Interleukin*-10 (*IL*-10) *Signaling Path-*

*ways: Alternate Roles of Viral and Cellular IL-10 in Rhesus Cytomegalovirus Infection*. J Virol, 2016. 90 (21): p. 9920-9930.

34. Jones, B. C., N. J. Logsdon, K. Josephson, J. Cook, P. A. Barry, and M. R. Walter, *Crystal structure of human cytomegalovirus IL-10 bound to soluble human IL-10R1*. Proc Natl Acad Sci USA, 2002. 99 (14): p. 9404-9.
35. Chang, W. L. and P. A. Barry, *Cloning of the full-length rhesus cytomegalovirus genome as an infectious and self-excisable bacterial artificial chromosome for analysis of viral pathogenesis*. J Virol, 2003. 77 (9): p. 5073-83.
36. Avdic, S., B. P. McSharry, and B. Slobedman, Modulation of dendritic cell functions by viral IL-10 encoded by human cytomegalovirus. *Front Microbiol,* 2014. 5: p. 337.
37. Hansen, S. G., D. E. Zak, G. Xu, J. C. Ford, E. E. Marshall, D. Malouli, R. M. Gilbride, C. M. Hughes, et al., *Prevention of tuberculosis in rhesus macaques by a cytomegalovirus-based vaccine*. Nat Med, 2018. 24 (2): p. 130-143.
38. Krawiec, J. A., H. Chen, S. Alom-Ruiz, and M. Jaye, *Modified PAXgene method allows for isolation of high-integrity total RNA from microlitre volumes of mouse whole blood*. Lab Anim, 2009. 43 (4): p. 394-8.
39. Hartigan-O'Connor, D., A. Amalfitano, and J. S. Chamberlain, *Improved production of gutted adenovirus in cells expressing adenovirus preterminal protein and DNA polymerase*. J Virol, 1999. 73 (9): p. 7835-41.
40. Amalfitano, A., M. A. Hauser, H. Hu, D. Serra, C. R. Begy, and J. S. Chamberlain, *Production and characterization of improved adenovirus vectors with the E1, E2b, and E3 genes deleted*. J Virol, 1998. 72 (2): p. 926-33.

Example 2. Co-Administration of an IL-10-Deficient Vaccine and an Anti-IL-10 Antibody This example describes an experiment performed to test the impact of IL-10 inhibitor administration on host immune responses to, and the efficacy of, a viral IL-10-deficient rhesus CMV-based vaccine.

Two young macaques (8-13 months old) were assigned to receive anti-IL10 antibody followed three days later by RhCMVdIL10/SIVgag vaccine (i.e., lacking viral IL-10). The anti-IL10 antibody was clone 1F11R1LALA from the NIH non-human primate reagent resource. The antibody was rhesus CDR-grafted IgG1 kappa containing the L234A and L235A Fc silencing mutations. It was a recombinant antibody derived from a mouse anti-human IL-10 mAb clone that cross-reacts with rhesus IL-10. Mouse CDRs were grafted in human Fv frameworks. The constant regions were rhesus IgG1 (heavy) and kappa (light) chains. The antibody was produced from transduced CHO cells grown in serum-free medium, and purified by protein A affinity and anion exchange chromatography.

Both animals received 30 mg/kg anti-IL-10 antibody 1F11R1LALA on days-3 and 25, in each case three days before administration of RhCMVdIL10/SIVgag vaccine. All animals were administered SIV vaccine at a dose of $10^5$ pfu subcutaneously, in no more than 2 mL volume on day 0. All animals then received a booster dose approximately 4 weeks after the first dose. Finally, beginning >16 weeks after the first vaccine dose, all animals are challenged with increasing doses of SIV. The challenges were administered every two weeks, orally, in a maximum volume of 2.5 mL. One week after each challenge, blood samples were drawn and assayed using sensitive PCR-based techniques for the presence of SIV. When infection was detected in a blood sample, challenges were discontinued for that animal. Blood samples were subsequently drawn approximately every week and viral loads tested, to determine how many animals in each group were able to control viremia, which is an indicator of successful vaccine-mediated protection.

Figure 10:
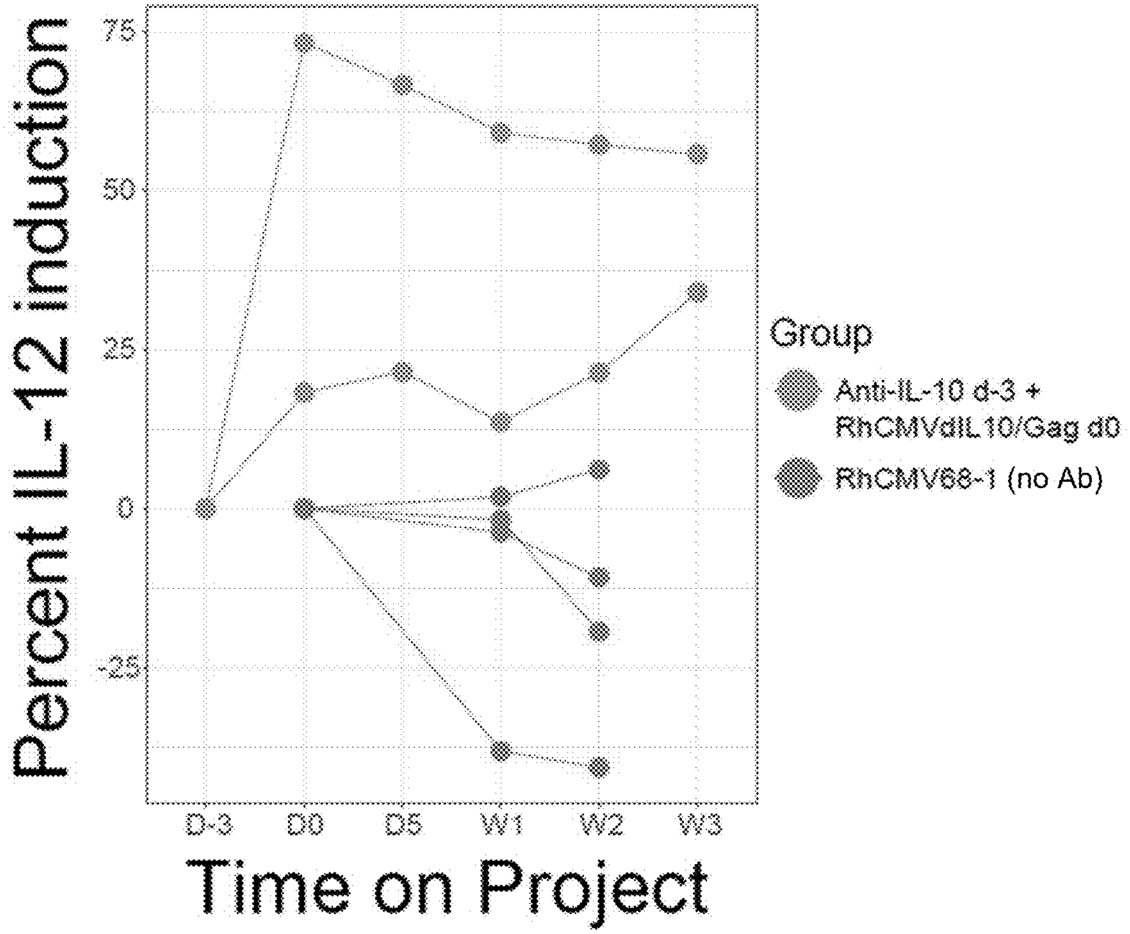
FIG. 10 shows that vaccinated animals receiving neutralizing antibodies against IL-10 have reduced IL-10 biological activity in plasma. One known biological function of IL-10 is to inhibit secretion of IL-12 and other cytokines. Thus, IL-10 present naturally in macaque plasma samples can be suppressive of IL-12 secretion that normally occurs when peripheral blood cells are incubated with lipopolysaccharide (LPS). The lower traces illustrate reduced induction of IL-12 in the presence of plasma from macaques receiving conventional vaccination, in the absence of antibody. The upper traces demonstrate that vaccinated animals receiving neutralizing anti-IL-10 have no residual IL-10 biological activity; indeed, addition of such plasma samples increases IL-12 secretion, due to continued presence of anti-IL-10 antibodies in plasma.

We first verified that administration of anti-IL-10 antibody 1F11R1LALA led to inhibition of host IL-10. The bioassay we employed tests if addition of a plasma sample to LPS-stimulated PBMCs can suppress production of IL-12; such suppression is a normal biological effect of IL-10. Indeed, we found that plasma samples from recipients of anti-IL-10 antibody were unable to suppress IL-12 production and instead caused increased production (FIG. 10), indicating that the antibody present in plasma neutralized endogenous IL-10 in vivo and furthermore suppressed any additional IL-10 produced by LPS-stimulated PBMCs.

Figure 11:
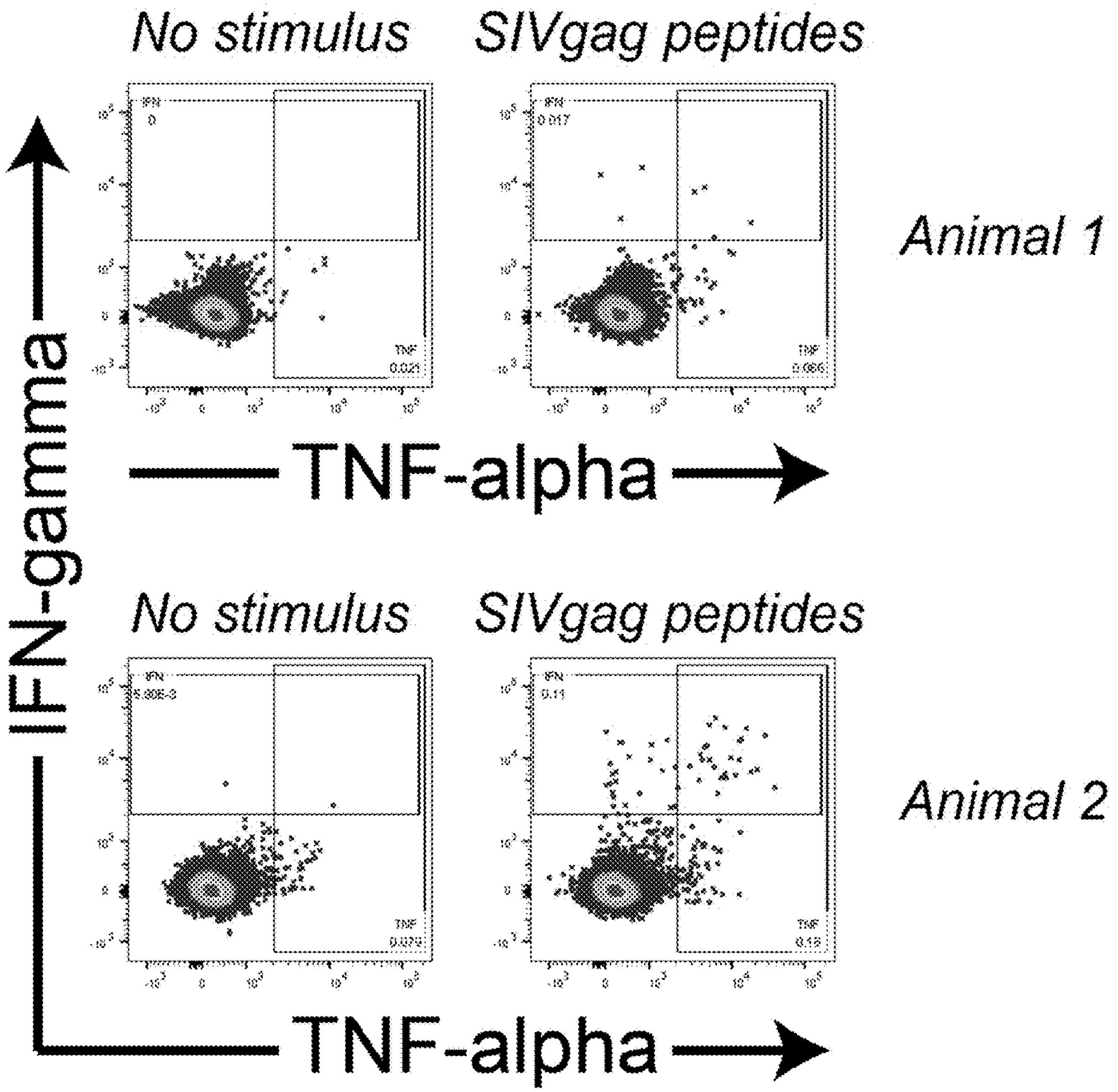
FIG. 11 shows CD4+ T cell responses to the vaccine antigen just two weeks after vaccination in the presence of anti-IL-10 neutralizing antibody. Shown are production of interferon-gamma (y axis) and TNF-alpha (x axis) by the PBMCs of animals vaccinated with IL-10 inhibition, when the cells are stimulated with Gag peptides (right) but not when left unstimulated (left).
Figure 12:
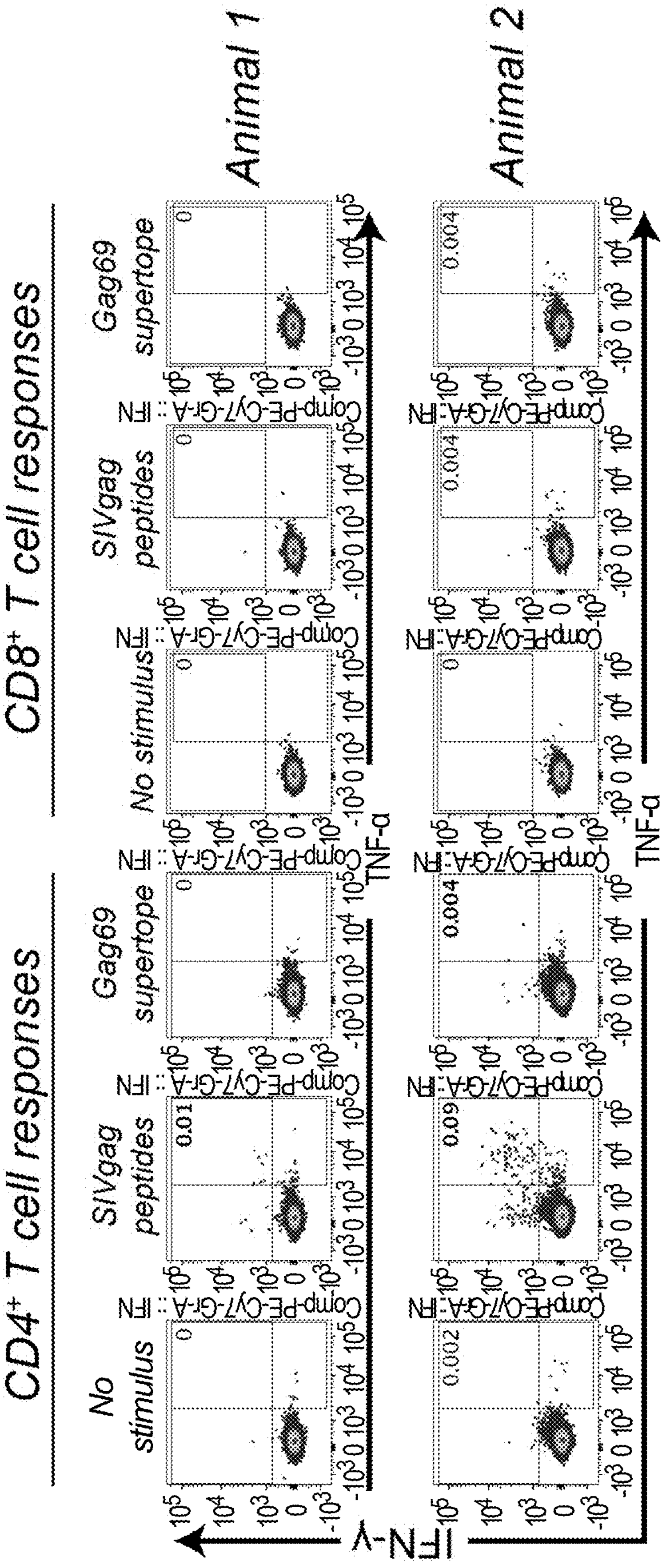
FIG. 12 shows low or absent CD8+ T cell responses to the vaccine antigen by eight weeks after vaccination in the presence of anti-IL-10 neutralizing antibody. Shown are production of interferon-gamma (y axis) and TNF-alpha (x axis) by the PBMCs of two animals vaccinated with IL-10 inhibition, when the cells are left unstimulated (left), stimulated with Gag peptides (middle), or stimulated with Gag69, a peptide from the Gag protein that is known to be presented on the class Ib molecule, Mamu-E. The data show robust responses among CD4+ T cells (0.01% or 0.09% of cells making cytokines, left), but few or no responses among CD8+ T cells (0% or 0.004%, right). Responses to the Gag69 supertope (Mamu-E restricted; seen as dots more distant from the origin in row 2, column 3) are observed among CD4+ T cells of Animal 2 but not in CD8+ T cells or cells from Animal 1.
Figure 13:
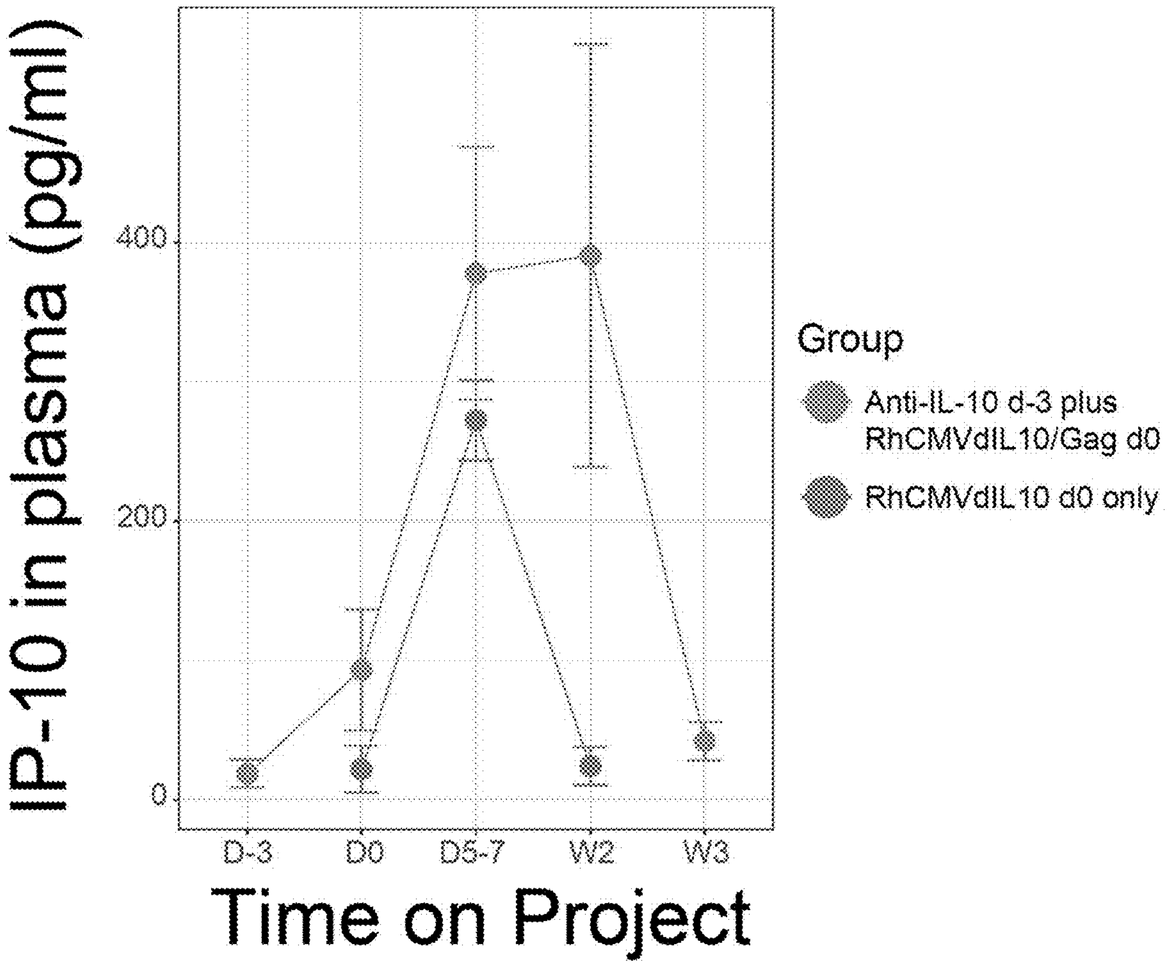
FIG. 13 demonstrates an altered cytokine environment after vaccination in the presence of IL-10 inhibitor. Both groups of animals in this figure were vaccinated with a viral IL-10-deficient rhesus cytomegalovirus. One group additionally received anti-host-IL-10 monoclonal antibody three days before vaccination. We then measured the concentration of IP-10 (interferon-gamma-induced protein 10, also known as CXCL10) in plasma at various times after vaccination. The figure shows that animals receiving vaccination with IL-10 inhibition have more IP-10 in circulation, with the most dramatic difference observed two weeks after vaccination.

Analysis of immune responses after vaccine administration revealed three remarkable effects of the anti-IL-10 antibody: (i) very rapid induction of T cell responses—by two weeks after first vaccination (FIG. 11), (ii) nearly complete inhibition of responses among CD8+ T cells by eight weeks (FIG. 12) and (iii) an altered cytokine environment (FIG. 13).

Thus, use of an anti-IL-10 agent as adjuvant in this case would assist in protection against disease in instances when a rapid response is desirable (e.g., to allow more rapid protection against an infectious disease), when the classically restricted CD4+ T cell response is most needed, or when CD8+ T cell responses are undesirable.

Example 3. Expression of an Antigen and Dominant-Negative IL-10 Receptor in a Vaccine An adenovirus-based vector vaccine with deletions in the E1 and E3 regions (e.g., a type-5 adenovirus) is prepared that additionally carries an EF1alpha promoter, an optimized coding sequence for SIVgag, an internal ribosomal entry site (IRES) from encephalomyocarditis virus (EMCV), and a coding sequence for an IL-10 receptor from the host (vaccine recipient) that is truncated so that key amino acid residues for signaling from the receptor are absent. The protein expressed in this particular example has the truncated sequence of the *Macaca mulatta* interleukin 10 receptor subunit alpha (IL10RA) protein:

```
                                        (SEQ ID NO: 5)
MVAVILLATIPSLLLILGGWVLPAVVLTFFSPGTELPSPPSVWFEAEFF

HHILHWTPIPNQSESTCYEVALLRYGTGRWNSISNCSQALSYDLTAVTL

DLYRSNGYWARVRAVDGSRHSNWTVTNTRFSLDEVTLTVGSVKLEIHNG

FILGKIQPPRPKMAPANDTYESIFSHFREYEIAIRKVPGNFTFTHKKVK

HENFSLLTSGEVGEFCVQVKPSVTSRTNKGMWSKEECVSLTRQYFTVTN

VIIFFAFVLLLSGALAYCLALQLYVRRR.
```

The antigen and the truncated IL-10 receptor can be expressed together in an antigen-presenting cell. Presence of the truncated IL-10 receptor causes the antigen-presenting cell to be less sensitive to application of an exogenous protein that has IL-10-like activity; that is, some effects of the protein that has IL-10-like activity on the antigen-presenting cell are reduced or eliminated. Administration of this vaccine to the host results in a more intense beneficial immune response (e.g., greater $CD8^+$ T-cell responses at some point after vaccine administration) and/or the vaccine results in beneficial immune responses in a greater fraction of vaccine recipients, as compared to a vaccine lacking the truncated IL-10 receptor.

Example 4. Expression of an Antigen and Truncated IL-10-Like Protein in a Vaccine An adenovirus-based vector vaccine with deletions in the E1 and E3 regions (e.g., a type-5 adenovirus) is prepared that additionally carries an EF1alpha promoter, an optimized coding sequence for SIVgag, an internal ribosomal (IRES) from encephalomyocarditis virus (EMCV), and a coding sequence for a truncated IL-10-like protein. The protein expressed in this particular example has the truncated sequence of the rhesus cytomegalovirus interleukin-10 protein, which in its truncated form is the ortholog of the human CMV LAcmvIL-10 sequence (a truncated IL-10-like protein that is expressed naturally in human CMV infection):

(SEQ ID NO: 7)

```
MRRRRRSFGIIVAGAIGTLLMMAVVVLSAHDHEHKEVPPACDPVHGNLA

GIFKELRATYASIREGLQKKDTVYYTSLFNDRVLHEMLSPMGCRVTNEL

MEHYLDGVLPRASHLDYDNSTLNGLHVFASSMQALYQHMLKCVSVSGSI

TPRYDT.
```

Truncation of the amino acid sequence of the IL-10-like protein, possibly with addition of a small number of new amino acids, causes the protein to have restricted or reduced activity, relative to an intact protein that has IL-10-like activity. Presence of the truncated IL-10-like protein alone and/or complexes of the truncated IL-10-like protein with other molecules partially or completely inhibits some effects of a protein that has IL-10-like activity. For example, presence of excessive truncated IL-10-like protein can be inhibitory to the activity of a protein that has IL-10-like activity and/or co-expression in a cell of the truncated IL-10-like protein with a protein that has IL-10-like activity results in lesser function of the protein having IL-10-like activity (e.g., on a weight basis). Administration of this vaccine to the host results in a more intense beneficial immune response (e.g., greater $CD8^+$ T-cell responses at some point after vaccine administration) and/or the vaccine results in beneficial immune responses in a greater fraction of vaccine recipients, as compared to a vaccine lacking the truncated IL-10-like protein.

Example 5. An Ad26-Vectored SIV Vaccine Expressing SIVgag and Dominant-Negative IL-10 Receptor One approach to IL-10 pathway inhibition is to use IL-10-neutralizing antibodies. System-wide inhibition of IL-10, however, is likely unacceptable for infants, given that IL-10 deficiency is associated with inflammatory bowel disease and psoriasis. Any increased risk of these conditions for purposes of vaccination would be unacceptable. We therefore pursued the innovative strategy of inhibiting IL-10 signaling only in cells transduced by the vaccine and particularly in antigen presenting cells (APCs) whose expression of co-stimulatory receptors and cytokines is inhibited by IL-10. We employed a dominant-negative form of the IL-10 receptor lacking its intracellular domain. Normal signaling from the active IL-10-receptor complex requires Jak1 and Tyk2 phosphorylation of the Y446 and Y496 residues of IL-10R1. These phosphotyrosines provide docking sites that recruit and activate, via additional phosphorylation, the transcription factor STAT3. The IL-10R1 molecule lacking its intracellular domain lacks these crucial tyrosines; thus, signaling cannot occur.

Figure 14A:
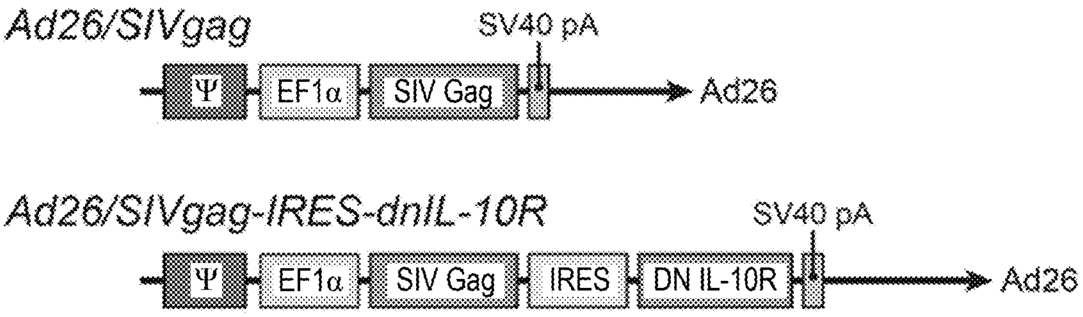
FIGS. 14A-14F show Ad26-vectored vaccines expressing SIVgag with or without dominant-negative IL-10 receptor (dnIL-10R).
Figure 14B:
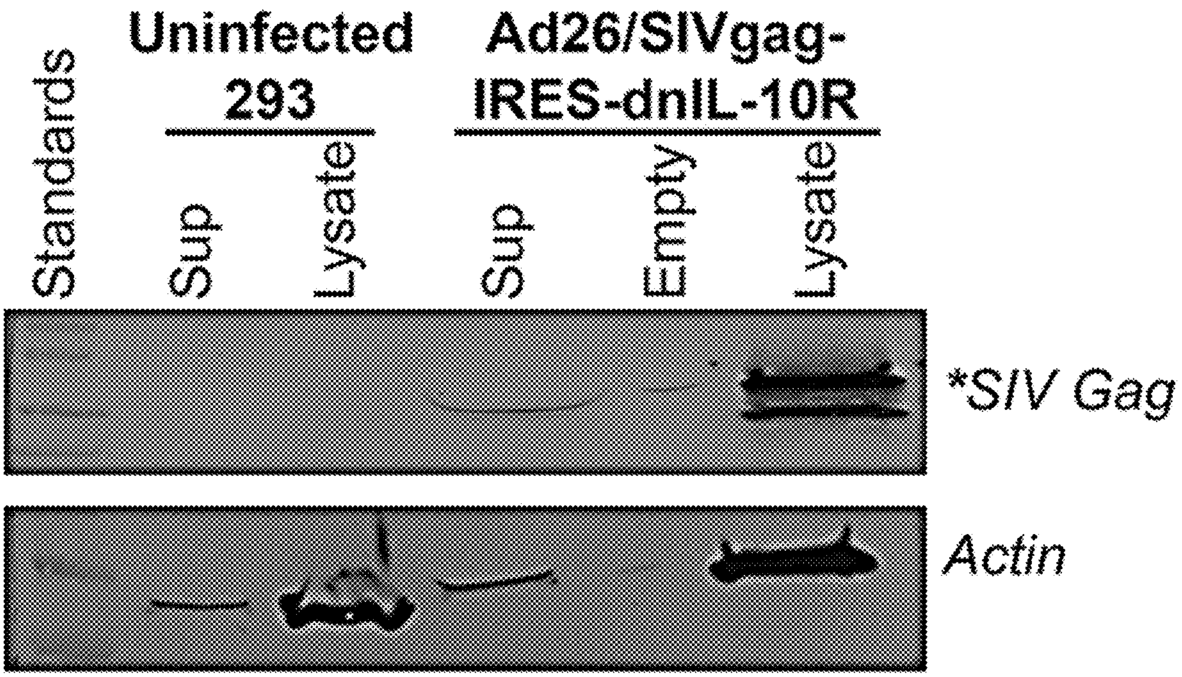
Figure 14C:
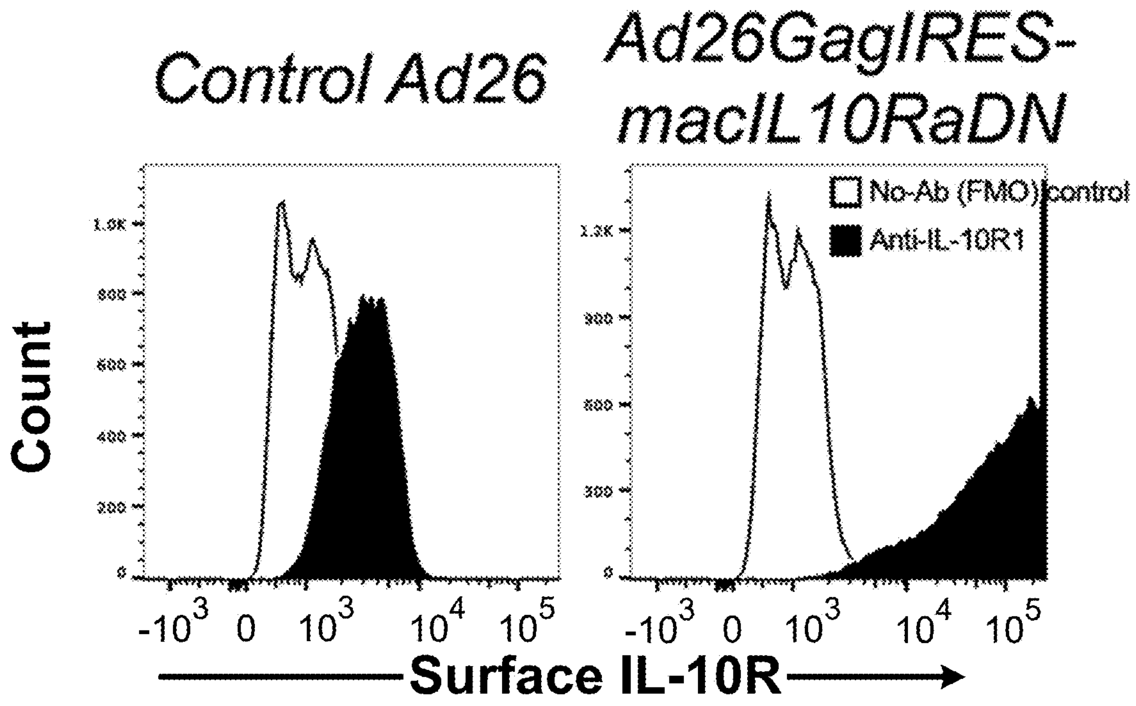
Figure 14D:
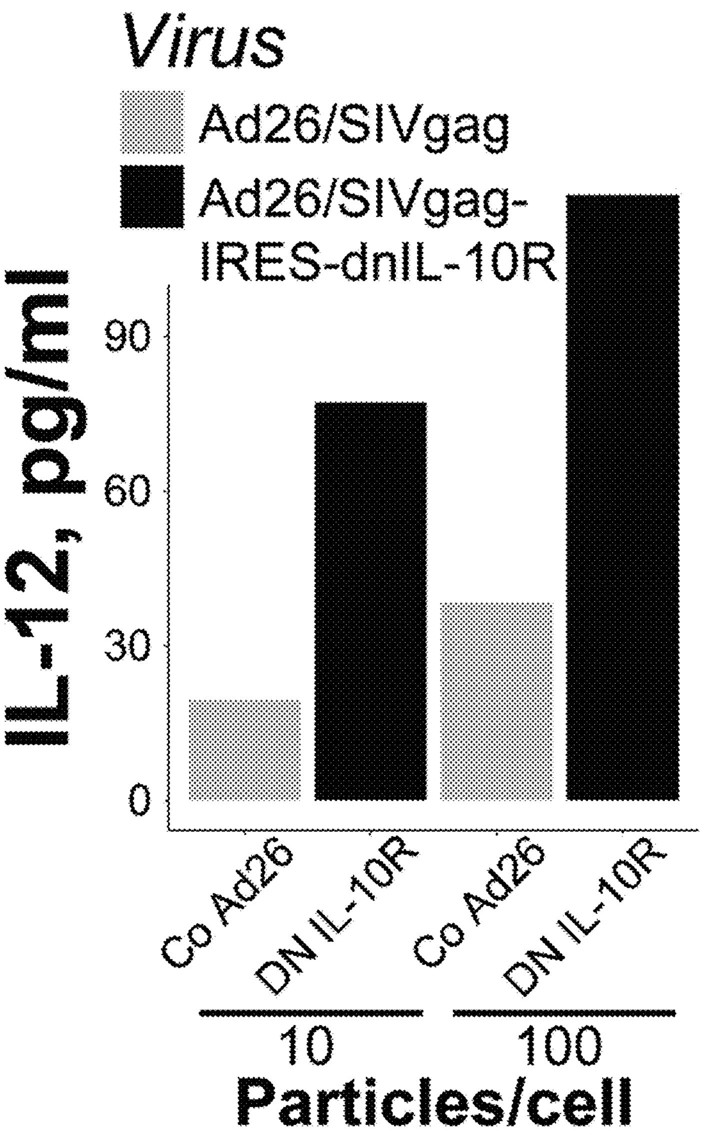
Figure 14E:
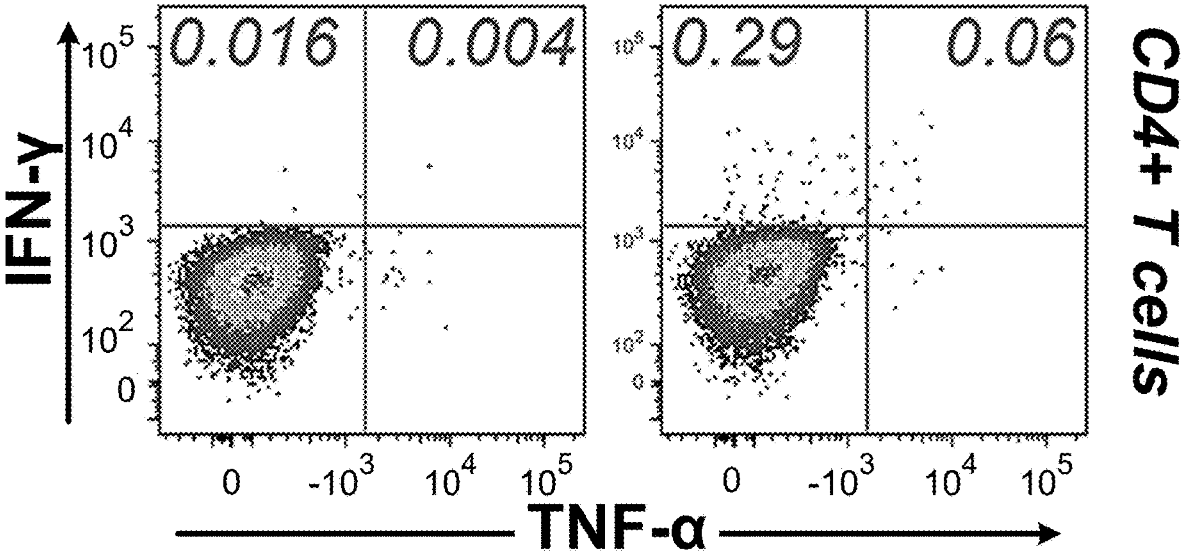
Figure 14F:
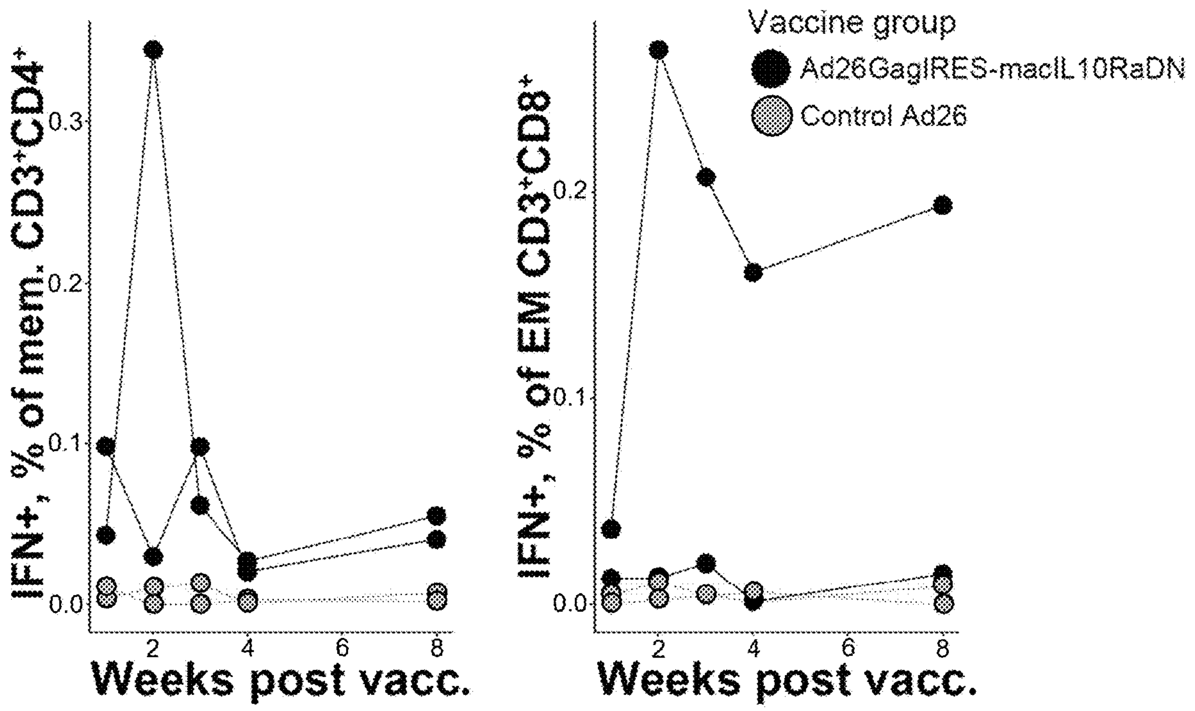

We vectorized adenovirus type 26 by recombinatorial capture in a plasmid backbone, deletion of the E1 and E3 regions, and replacement of the Ad26 E4orf6 with Ad5 E4orf6, to enable the needed interaction with EIB. We then engineered two expression cassettes, both containing the optimized SIVmac239 Gag sequence, and one coding additionally for dominant-negative IL-10 receptor (DNIL-10R) lacking its intracellular domain, under translational control of the ECMV IRES sequence (FIG. 14A). We tested these vectors to ensure protein expression and functional activity. Both vectors express Gag, as expected (FIG. 14B), while only Ad26/SIVgag-DNIL-10R expressed the truncated IL-10 receptor, which was detected by flow cytometry on the surface of transduced HEK 293 cells (FIG. 14C). Furthermore, expression of the truncated receptor caused insensitivity to the inhibitory effects of IL-10 on cytokine production in vitro (FIG. 14D). Finally, the Ad26/SIVgag-DNIL-10R vector was confirmed to be immunogenic in two recipient monkeys during eight weeks of follow up after vaccine administration ($10^{12}$ particles; FIGS. 14E and 14F).

VI. Exemplary Embodiments

Exemplary embodiments provided in accordance with the presently disclosed subject matter include, but are not limited to, the claims and the following embodiments:

1. A method for inducing an immune response against an antigen in a subject, the method comprising administering to the subject a therapeutically effective amount of an interleukin 10 (IL-10) inhibitor and a vaccine.

2. The method of embodiment 1, wherein viral and/or cellular IL-10 are inhibited.

3. The method of embodiment 1 or 2, wherein STAT3 transducer of IL-10 receptor signaling is inhibited.

4. The method of any one of embodiments 1 to 3, wherein the IL-10 inhibitor comprises a protein, a nucleic acid sequence encoding a protein, a small molecule, or a combination thereof.

5. The method of embodiment 4, wherein the protein comprises an antibody.

6. The method of embodiment 5, wherein the antibody is an anti-IL-10 antibody, an anti-IL-10 receptor (IL-10R) antibody, an anti-CD20 antibody, or a combination thereof.

7. The method of embodiment 5 or 6, wherein the antibody is selected from the group consisting of anti-IL-10 1F11R1LALA, rituximab, and a combination thereof.

8 The method of embodiment 4, wherein the protein comprises an Fc-IL-10R fusion protein.

9. The method of embodiment 8, wherein the fusion protein inhibits binding of all proteins to IL-10R.

10. The method of embodiment 8 or 9, wherein the fusion protein has a high binding affinity for IL-10.

11. The method of any one of embodiments 8 to 10, wherein the fusion protein inhibits IL-10 receptor signaling.

12. The method of any one of embodiments 8 to 11, wherein the fusion protein inhibits host and/or viral IL-10.

13. The method of embodiment 4, wherein the protein comprises a portion of an IL-10 protein that comprises one or more mutations that increase affinity of the portion of the IL-10 protein for an IL-10 receptor.

14. The method of embodiment 4, wherein the nucleic acid sequence encodes a protein comprising a portion of an IL-10 protein that comprises one or more mutations that increase affinity of the portion of the IL-10 protein for an IL-10 receptor.

15. The method of embodiment 4, wherein the protein comprises a truncated IL-10 receptor protein.

16. The method of embodiment 4, wherein the nucleic acid sequence encodes a protein comprising a truncated IL-10 receptor protein.

17. The method of embodiment 15 or 16, wherein the truncated IL-10 receptor protein comprises the amino acid sequence set forth in any one of SEQ ID NOS: 5-6.

18. The method of embodiment 4, wherein the protein comprises a truncated protein having IL-10-like activity.

19. The method of embodiment 4, wherein the nucleic acid sequence encodes a protein comprising a truncated protein having IL-10-like activity.

20. The method of embodiment 18 or 19, wherein the truncated protein having IL-10-like activity comprises the amino acid sequence set forth in SEQ ID NO:7.

21. The method of embodiment 4, wherein the protein comprises a dominant-negative STAT3 protein.

22. The method of embodiment 4, wherein the nucleic acid sequence encodes a protein comprising a dominant-negative STAT3 protein.

23. The method of embodiment 21 or 22, wherein the dominant-negative STAT3 protein comprises the amino acid sequence set forth in any one of SEQ ID NOS: 8-10.

24. The method of embodiment 4, wherein the small molecule comprises AS-101.

25. The method of any one of embodiments 1 to 24, wherein the vaccine comprises a recombinant polynucleotide comprising an adenovirus genome, or a portion thereof, and a nucleic acid sequence encoding the antigen.

26. The method of embodiment 25, wherein the recombinant polynucleotide further comprises a nucleic acid sequence encoding the IL-10 inhibitor.

27. The method of any one of embodiments 1 to 24, wherein the vaccine comprises a recombinant polynucleotide comprising a cytomegalovirus (CMV) genome, or a portion thereof, and a nucleic acid sequence encoding the antigen.

28. The method of any one of embodiments 1 to 24, wherein the vaccine is an IL-10-deficient vaccine.

29. The method of embodiment 28, wherein the IL-10-deficient vaccine comprises a recombinant polynucleotide comprising a cytomegalovirus (CMV) genome, or a portion thereof, and a nucleic acid sequence encoding the antigen, wherein the CMV genome or portion thereof comprises one or more immunomodulatory mutations, wherein the one or more immunomodulatory mutations comprise a mutation within a nucleic acid sequence encoding a protein that has CMV interleukin-10 (CMV IL-10)-like activity.

30. The method of embodiment 29, wherein the one or more immunomodulatory mutations are located in a regulatory region and/or a protein coding region of the nucleic acid sequence encoding the protein that has CMV IL-10-like activity.

31. The method of embodiment 27, 29, or 30, wherein the CMV is a CMV that can infect human, non-human primate, or mouse cells.

32. The method of any one of embodiments 29 to 31, wherein the protein that has CMV IL-10-like activity is human CMV IL-10 (HCMVIL-10) or rhesus macaque CMV IL-10 (RhCMVIL-10).

33. The method of any one of embodiments 27 and 29 to 32, wherein the nucleotide sequence encoding the antigen is located within the CMV genome or portion thereof.

34. The method of any one of embodiments 27 and 29 to 33, wherein the antigen is a non-CMV antigen.

35. The method of any one of embodiments 29 to 34, wherein the one or more immunomodulatory mutations comprise a substitution, a deletion, and/or an insertion of one or more nucleotides.

36. The method of any one of embodiments 29 to 35, wherein the mutation within the nucleic acid sequence encoding the protein that has CMV IL-10-like activity comprises a deletion within the first two exons of the nucleic acid sequence encoding the protein that has CMV IL-10-like activity.

37. The method of any one of embodiments 29 to 36, wherein the mutation within the nucleic acid sequence encoding the protein that has CMV IL-10-like activity reduces or inactivates the activity of the protein having CMV IL-10-like activity.

38. The method of any one of embodiments 29 to 37, wherein the one or more immunomodulatory mutations further comprise an insertion of a nucleic acid sequence encoding an immunostimulatory protein.

39. The method of embodiment 38, wherein the immunostimulatory protein is a cytokine.

40. The method of embodiment 39, wherein the cytokine is selected from the group consisting of interleukin-12 (IL-12), interleukin-15 (IL-15), and a combination thereof.

41. The method of any one of embodiments 29 to 40, wherein the CMV is a CMV capable of infecting rhesus macaque cells and wherein the one or more immunomodulatory mutations further comprise a mutation within a region of the CMV genome or portion thereof selected from the group consisting of Rh182, Rh183, Rh184, Rh185, Rh186, Rh187, Rh188, Rh189, and a combination thereof.

42. The method of any one of embodiments 29 to 40, wherein the CMV is a CMV capable of infecting human cells and wherein the one or more immunomodulatory mutations further comprise a mutation within a region of the CMV genome or portion thereof selected from the group consisting of US2, US3, US4, US5, US6, US7, US8, US9, US10, US11, and a combination thereof.

43. The method of any one of embodiments 29 to 42, wherein the one or more immunomodulatory mutations further comprise a mutation within a nucleic acid sequence encoding a protein that inhibits antigen presentation by a major histocompatibility complex (MHC) molecule.

44. The method of any one of embodiments 29 to 43, wherein the one or more immunomodulatory mutations further comprise a mutation that increases or decreases the unfolded protein response (UPR).

45. The method of embodiment 44, wherein the mutation that increases or decreases the UPR decreases or increases the expression of Human cytomegalovirus UL50, Rhesus cytomegalovirus Rh81, or Mouse cytomegalovirus M50.

46. The method of any one of embodiments 1 to 45, wherein the antigen is an infectious disease antigen.

47. The method of embodiment 46, wherein the infectious disease antigen is a bacterial, viral, fungal, protozoal, and/or helminthic infectious disease antigen.

48. The method of embodiment 46 or 47, wherein the infectious disease antigen is a viral infectious disease antigen from simian immunodeficiency virus (SIV), human immunodeficiency virus (HIV), hepatitis C virus, herpes simplex virus, Epstein-Barr virus, or a combination thereof.

49. The method of any one of embodiments 46 to 48, wherein the infectious disease antigen comprises an HIV or SIV group-specific antigen (gag) protein.

50. The method of any one of embodiments 1 to 45, wherein the antigen is a tumor-associated antigen.

51. The method of embodiment 50, wherein the tumor-associated antigen is selected from the group consisting of prostate-specific antigen, melanoma-associated antigen 4 (MAGEA4), melanoma-associated antigen 10 (MAGEA10), NY-ESO-1, a neoantigen, and a combination thereof.

52. The method of any one of embodiments 27 and 29 to 51, wherein the CMV genome or portion thereof further comprises a mutation that increases tropism or selectivity for a target cell.

53. The method of embodiment 52, wherein the target cell is selected from the group consisting of an antigen-presenting cell, a tumor cell, a fibroblast, an epithelial cell, an endothelial cell, and a combination thereof.

54. The method of embodiment 53, wherein the antigen-presenting cell is a dendritic cell.

55. The method of any one of embodiments 52 to 54, wherein the mutation that increases tropism or selectivity comprises a mutation that modifies a protein, or portion thereof, that is positioned on the outside of the CMV virion.

56. The method of any one of embodiments 52 to 55, wherein the mutation that increases tropism or selectivity comprises an insertion of a nucleotide sequence encoding a cellular targeting ligand.

57. The method of embodiment 56, wherein the cellular targeting ligand is selected from the group consisting of an antibody fragment that recognizes a target cell antigen, a ligand that is recognized by a target cell cognate receptor, a viral capsid protein that recognizes a target cell, and a combination thereof.

58. The method of embodiment 56 or 57, wherein the cellular targeting ligand is CD154.

59. The method of any one of embodiments 52 to 58, wherein the CMV is a CMV capable of infecting rhesus macaque cells and wherein the mutation that increases tropism or selectivity comprises a mutation within a gene selected from the group consisting of Rh13.1, Rh61/Rh60, Rh157.4, Rh157.5, Rh157.6, and a combination thereof.

60. The method of any one of embodiments 52 to 58, wherein the CMV is a CMV capable of infecting human cells and wherein the mutation that increases tropism or selectivity comprises a mutation within a gene selected from the group consisting of RL13, UL36, UL130, UL128, UL131, and a combination thereof.

61. The method of any one of embodiments 27 and 29 to 60, wherein the recombinant polynucleotide further comprises a nucleic acid sequence encoding a selectable marker.

62. The method of embodiment 61, wherein the nucleic acid sequence encoding the selectable marker is located within the CMV genome or portion thereof.

63. The method of embodiment 61 or 62, wherein the nucleic acid sequence encoding the selectable marker comprises a nucleic acid sequence encoding an antibiotic resistance gene and/or a fluorescent protein.

64. The method of any one of embodiments 27 and 29 to 63, wherein the recombinant polynucleotide contains one or more regulatory sequences.

65. The method of embodiment 64, wherein the one or more regulatory sequences control the expression of a gene or region within the CMV genome or portion thereof, the antigen-encoding sequence, an immunostimulatory protein-encoding sequence, a selectable marker-encoding sequence, a variant thereof, or a combination thereof.

66. The method of embodiment 64 or 65, wherein the one or more regulatory sequences comprise a CMV early enhancer, a chicken beta-actin gene promoter, a first exon of a chicken beta-actin gene, a first intron of a chicken beta-actin gene, a splice acceptor of a rabbit beta-globin gene, an EM7 promoter, an EFla promoter, or a combination thereof.

67. The method of any one of embodiments 27 to 66, wherein the recombinant polynucleotide further comprises a nucleic acid sequence encoding the IL-10 inhibitor.

68. The method of any one of embodiments 27 to 66, wherein the IL-10 inhibitor comprises a protein encoded by a nucleic acid sequence.

69. The method of any one of embodiments 1 to 68, wherein the IL-10 inhibitor and the vaccine are administered at about the same time.

70. The method of any one of embodiments 1 to 68, wherein the IL-10 inhibitor is administered before and/or after the vaccine.

71. A method for preventing or treating a disease in a subject, the method comprising inducing an immune response against an antigen in the subject according to the method of any one of embodiments 1 to 70.

72. The method of embodiment 71, wherein the disease is an infectious disease or cancer.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, and sequence reference numbers cited herein are hereby incorporated by reference in their entirety for all purposes.

What is claimed is:

1. A method for inducing an immune response against an antigen in a subject, the method comprising administering to the subject an interleukin 10 (IL-10)-deficient vaccine and a therapeutically effective amount of an IL-10 inhibitor, wherein the IL-10-deficient vaccine comprises a recombinant polynucleotide comprising a cytomegalovirus (CMV) genome, or a portion thereof, and a nucleic acid sequence encoding the antigen, wherein:

(i) a portion of the CMV genome encodes a protein that has interleukin-10 (CMV IL-10)-like activity; and (ii) the portion of the CMV genome in (i) comprises one or more immunomodulatory mutations, and wherein the IL-10 inhibitor comprises:

(a) a truncated IL-10 receptor protein comprising the amino acid sequence set forth in any one of SEQ ID NOS: 5-6 but lacking the portion of the IL-10 receptor protein necessary for intracellular signaling;

(b) a truncation of a protein having IL-10-like activity, wherein the truncation consists of the amino acid sequence set forth in SEQ ID NO:7:

(c) a dominant-negative STAT3 protein comprising the amino acid sequence set forth in any one of SEQ ID NOS: 8-10; or (d) a nucleic acid sequence encoding the IL-10 inhibitor.

2. The method of claim 1, further comprising inhibiting viral and/or cellular IL-10 activity.

3. The method of claim 1, further comprising inhibiting STAT3 transducer of IL-10 receptor signaling.

4. The method of claim 1, wherein the method further comprises inducing a $CD4^+$ T cell immune response.

5. The method of claim 1, wherein the recombinant polynucleotide further comprises the nucleic acid sequence encoding the IL-10 inhibitor.

6. The method of claim 1, wherein the one or more immunomodulatory mutations reduce or inactivate the activity of the protein that has CMV IL-10-like activity.

7. The method of claim 6, wherein the one or more immunomodulatory mutations further comprise an insertion of a nucleic acid sequence encoding an immunostimulatory protein.

8. The method of claim 7, wherein the immunostimulatory protein is a cytokine selected from the group consisting of interleukin-12 (IL-12), interleukin (IL-15), and a combination thereof.

9. The method of claim 1, wherein the antigen is an infectious disease antigen.

10. The method of claim 9, wherein the infectious disease antigen is a viral infectious disease antigen from simian immunodeficiency virus (SIV), human immunodeficiency virus (HIV), hepatitis C virus, herpes simplex virus, Epstein-Barr virus, or a combination thereof.

11. The method of claim 9, wherein the infectious disease antigen comprises an HIV or SIV group-specific antigen (gag) protein.

12. The method of claim 1, wherein the antigen is a tumor-associated antigen.

13. A method for treating a disease in a subject, the method comprising inducing an immune response against an antigen in the subject according to the method of claim 1.

14. The method of claim 13, wherein the disease is an infectious disease or cancer.

15. The method of claim 1, wherein said administering comprises providing a dose of the IL-10-deficient vaccine comprising between $10^4$ and about $10^{13}$ plaque-forming units (pfu).

16. The method of claim 1, wherein said administering comprises providing a dose of the IL-10 inhibitor at a concentration of about 30 mg/mL.

17. The method of claim 1, wherein said administering comprises providing the IL-10 inhibitor and the IL-10-deficient vaccine at about the same time.

18. The method of claim 1, wherein said administering comprises providing the IL-10 inhibitor and the IL-10-deficient vaccine sequentially.

* * * * *

SEQUENCE LISTING

```
<160> NUMBER OF SEQ ID NOS: 10

<210> SEQ ID NO 1
<211> LENGTH: 178
<212> TYPE: PRT
<213> ORGANISM: Macaca mulatta

<400> SEQUENCE: 1

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr Arg
            20                  25                  30

Phe Pro Gly Asn Leu Pro His Met Leu Arg Asp Leu Arg Asp Ala Phe
```

-continued

```
        35                  40                  45

Ser Arg Val Lys Thr Phe Phe Gln Met Lys Asp Gln Leu Asp Asn Ile
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn His Asp Pro Asp Ile Lys Glu His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Ser Lys Leu Gln Glu Lys Gly Val Tyr Lys Ala Met Ser Glu
145                 150                 155                 160

Phe Asp Ile Phe Ile Asn Tyr Ile Glu Ala Tyr Met Thr Met Lys Ile
                165                 170                 175

Gln Asn


<210> SEQ ID NO 2
<211> LENGTH: 178
<212> TYPE: PRT
<213> ORGANISM: Homo sapiens

<400> SEQUENCE: 2

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn


<210> SEQ ID NO 3
<211> LENGTH: 1175
<212> TYPE: DNA
<213> ORGANISM: Cercopithecine herpesvirus 8

<400> SEQUENCE: 3
```

-continued

```
atgcggagga ggaggaggtc tttcggcatc atcgtcgccg gcgctatcgg aacactactc     60

atgatggcgg tggtcgtgct ttcagcccat gaccatgaac acaaagaagt accaccggcc    120

tgtgaccccg ttcacggtaa cttggcaggc atcttcaagg agttgcgggc gacctacgct    180

tccattagag aaggtttggt atgttaggca acgcagttct cggatgtcag tccggatcgg    240

aggagtcaca gtctgtcatg tgatgatata ttgcttaatt tttgttttgc agcaaaagaa    300

ggacacggtg tactacacat cgctgttcaa tgaccgcgtg ctccatgaaa tgctgagtcc    360

tatgggctgt cgcgtgacca atgaactcat ggaacattat ttagatggtg ttctgcctcg    420

agcaagtcat ttagactacg ataatagcac tctgaatggc ttacatgtgt ttgcttcatc    480

catgcaggcg ctgtatcagc acatgttaaa gtgtgtaagt gtttcaggtt cgataacccc    540

gcgatatgac acgtaaatag cgatatcgtg gcaccagacg tcagtcacag tcttccccgg    600

tcgagacgca tcttatatcg cgatatatcg cggattatcg cagtatgtag cgatatatcg    660

tgtcaaagca ctccgaacga cattctgatg acggctatcg ccttatgtcg cggtatatcg    720

cggaatatcg cagtatatcg cggttatgtc gcgacataac cgtcatgtcg cgactatcgc    780

cgcatatcgc cactatcgcg acttggcacc gtgccaacga tagtcgacct tagggtggtc    840

gtgtggtggt ggggggctgc ttgcggtttg caaaccggag aggtagcaca cgctgattgt    900

cggtttggaa gcgttgttta cacatgtctt tgtcttggca gcccgcgttg gcatgtactg    960

gcaaaacgcc agcttggatg tacttcttgg aggtggaaca caaggtcagt taaggttgcc   1020

aggtaggtta aaacgcagaa accattgttc taccggtttc ctaaaacgcc gttcaacgtg   1080

ttttgcagct caacccctgg aggggcacgg caaaagccgc ggccgaggct gaccttttgc   1140

tgaactactt ggaaacgttc ctgctgcagt tctga                              1175

<210> SEQ ID NO 4
<211> LENGTH: 1179
<212> TYPE: DNA
<213> ORGANISM: Cercopithecine herpesvirus 8

<400> SEQUENCE: 4

atgcggagga ggaggaggtc tttcggcatc atcgtcgccg gcgctatcgg aacactactc     60

atgatggcgg tggtcgtgct ttcagcccat gaacacaaag aagtaccacc ggcctgtgac    120

cccgttcacg gtaacttggc aggcatcttc aaggagttgc gggcgaccta cgcttccatt    180

agagaaggtt tggtatgtta ggcaacgcag ttctcggatg tcagtccgga tcggaggagt    240

cacagtctgt catgtgatga tatattgctt catttttgtt ttgcagcaaa agaaggacac    300

ggtgtactac acatcgctgt tcaatgaccg cgtgctccat gagatgctga gtcctatggg    360

ctgtcgcgtg accaacgaac tcatggaaca ttatttagat ggtgttctgc ctcgagcaag    420

tcatttagac tacgataata gcactctgaa tggcttacat gtgtttgctt catccatgca    480

ggcgctgtat cagcacatgt taaagtgtgt aagtgtttca ggttcgataa ccccgcgata    540

tgacacgtaa atagcgatat cgtggcacca gacgtcagtc acagtcttcc ccggtcgaga    600

cgcatcttat atcgcgatat atcgcggttt atcgcagtat gtcgcgatat atcgctccaa    660

aacactccgg atgactttct atcgccgaat atcacctcat atcgtcttat atcgcggtgt    720

atcgcgggtt atcgtcatat atcgcggtta tgtcgcgaca taaccgtcat gtcgcgacta    780

tcgccgcata tcgccactat cgcgacttgg cacggtgcca acaatagttg cctctagggt    840

ggtcgtgtgg tggtaggggg ctgcttacgg tttgcaaacc ggagaggtcg cacacgctga    900

ttgtcggttt ggaagcgttg tttacacatg tctttgtctt ggcagcccgc gttggcatgt    960
```

-continued

```
actggcaaaa cgccagcttg gatgtacttc ttggaggtgg aacacaaggt cagttaaggt   1020

tgccaggtag gttaaaacgc agaaaccatt gttctaccgg tttcctaaaa cgccgttcaa   1080

cgtgttttgc agctcaaccc ctggaggggc acggcaaaag ccgcggccga ggctgacctt   1140

ttgctgaact acttggaaac gttcctgctg cagttctga                          1179


<210> SEQ ID NO 5
<211> LENGTH: 273
<212> TYPE: PRT
<213> ORGANISM: Macaca mulatta

<400> SEQUENCE: 5

Met Val Ala Val Ile Leu Leu Ala Thr Ile Pro Ser Leu Leu Leu Ile
1               5                   10                  15

Leu Gly Gly Trp Val Leu Pro Ala Val Val Leu Thr Phe Phe Ser Pro
            20                  25                  30

Gly Thr Glu Leu Pro Ser Pro Pro Ser Val Trp Phe Glu Ala Glu Phe
        35                  40                  45

Phe His His Ile Leu His Trp Thr Pro Ile Pro Asn Gln Ser Glu Ser
    50                  55                  60

Thr Cys Tyr Glu Val Ala Leu Leu Arg Tyr Gly Thr Gly Arg Trp Asn
65                  70                  75                  80

Ser Ile Ser Asn Cys Ser Gln Ala Leu Ser Tyr Asp Leu Thr Ala Val
                85                  90                  95

Thr Leu Asp Leu Tyr Arg Ser Asn Gly Tyr Trp Ala Arg Val Arg Ala
            100                 105                 110

Val Asp Gly Ser Arg His Ser Asn Trp Thr Val Thr Asn Thr Arg Phe
        115                 120                 125

Ser Leu Asp Glu Val Thr Leu Thr Val Gly Ser Val Lys Leu Glu Ile
    130                 135                 140

His Asn Gly Phe Ile Leu Gly Lys Ile Gln Pro Pro Arg Pro Lys Met
145                 150                 155                 160

Ala Pro Ala Asn Asp Thr Tyr Glu Ser Ile Phe Ser His Phe Arg Glu
                165                 170                 175

Tyr Glu Ile Ala Ile Arg Lys Val Pro Gly Asn Phe Thr Phe Thr His
            180                 185                 190

Lys Lys Val Lys His Glu Asn Phe Ser Leu Leu Thr Ser Gly Glu Val
        195                 200                 205

Gly Glu Phe Cys Val Gln Val Lys Pro Ser Val Thr Ser Arg Thr Asn
    210                 215                 220

Lys Gly Met Trp Ser Lys Glu Glu Cys Val Ser Leu Thr Arg Gln Tyr
225                 230                 235                 240

Phe Thr Val Thr Asn Val Ile Ile Phe Phe Ala Phe Val Leu Leu Leu
                245                 250                 255

Ser Gly Ala Leu Ala Tyr Cys Leu Ala Leu Gln Leu Tyr Val Arg Arg
            260                 265                 270

Arg


<210> SEQ ID NO 6
<211> LENGTH: 263
<212> TYPE: PRT
<213> ORGANISM: Homo sapiens

<400> SEQUENCE: 6

Met Leu Pro Cys Leu Val Val Leu Leu Ala Ala Leu Leu Ser Leu Arg
```

-continued

```
1               5                   10                  15

Leu Gly Ser Asp Ala His Gly Thr Glu Leu Pro Ser Pro Pro Ser Val
            20                  25                  30

Trp Phe Glu Ala Glu Phe Phe His His Ile Leu His Trp Thr Pro Ile
        35                  40                  45

Pro Asn Gln Ser Glu Ser Thr Cys Tyr Glu Val Ala Leu Leu Arg Tyr
    50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
        115                 120                 125

Ser Val Asn Leu Glu Ile His Asn Gly Phe Ile Leu Gly Lys Ile Gln
    130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
    210                 215                 220

Ser Leu Thr Arg Gln Tyr Phe Thr Val Thr Asn Val Ile Ile Phe Phe
225                 230                 235                 240

Ala Phe Val Leu Leu Leu Ser Gly Ala Leu Ala Tyr Cys Leu Ala Leu
                245                 250                 255

Gln Leu Tyr Val Arg Arg Arg
            260
```

<210> SEQ ID NO 7
<211> LENGTH: 153
<212> TYPE: PRT
<213> ORGANISM: Cercopithecine herpesvirus 8

<400> SEQUENCE: 7

```
Met Arg Arg Arg Arg Arg Ser Phe Gly Ile Ile Val Ala Gly Ala Ile
1               5                   10                  15

Gly Thr Leu Leu Met Met Ala Val Val Val Leu Ser Ala His Asp His
            20                  25                  30

Glu His Lys Glu Val Pro Pro Ala Cys Asp Pro Val His Gly Asn Leu
        35                  40                  45

Ala Gly Ile Phe Lys Glu Leu Arg Ala Thr Tyr Ala Ser Ile Arg Glu
    50                  55                  60

Gly Leu Gln Lys Lys Asp Thr Val Tyr Tyr Thr Ser Leu Phe Asn Asp
65                  70                  75                  80

Arg Val Leu His Glu Met Leu Ser Pro Met Gly Cys Arg Val Thr Asn
                85                  90                  95

Glu Leu Met Glu His Tyr Leu Asp Gly Val Leu Pro Arg Ala Ser His
            100                 105                 110
```

-continued

```
Leu Asp Tyr Asp Asn Ser Thr Leu Asn Gly Leu His Val Phe Ala Ser
        115                 120                 125

Ser Met Gln Ala Leu Tyr Gln His Met Leu Lys Cys Val Ser Val Ser
    130                 135                 140

Gly Ser Ile Thr Pro Arg Tyr Asp Thr
145                 150


<210> SEQ ID NO 8
<211> LENGTH: 770
<212> TYPE: PRT
<213> ORGANISM: Homo sapiens

<400> SEQUENCE: 8

Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
        35                  40                  45

Lys Glu Ser His Ala Thr Leu Val Phe His Asn Leu Leu Gly Glu Ile
    50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
                85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
        115                 120                 125

Ala Asn His Pro Thr Ala Ala Val Val Thr Glu Lys Gln Gln Met Leu
    130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
    210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
        275                 280                 285

Gln Lys Val Ser Tyr Lys Gly Asp Pro Ile Val Gln His Arg Pro Met
    290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335
```

-continued

```
Leu Val Ile Lys Thr Gly Val Gln Phe Thr Thr Lys Val Arg Leu Leu
            340                 345                 350

Val Lys Phe Pro Glu Leu Asn Tyr Gln Leu Lys Ile Lys Val Cys Ile
        355                 360                 365

Asp Lys Asp Ser Gly Asp Val Ala Ala Leu Arg Gly Ser Arg Lys Phe
    370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
            420                 425                 430

Thr Glu Glu Leu His Leu Ile Thr Phe Glu Thr Glu Val Tyr His Gln
        435                 440                 445

Gly Leu Lys Ile Asp Leu Glu Thr His Ser Leu Pro Val Val Val Ile
    450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
        515                 520                 525

Ala Glu Lys Leu Leu Gly Pro Gly Val Asn Tyr Ser Gly Cys Gln Ile
    530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
            580                 585                 590

Arg Glu Arg Ala Ile Leu Ser Thr Lys Pro Pro Gly Thr Phe Leu Leu
        595                 600                 605

Arg Phe Ser Glu Ser Ser Lys Glu Gly Gly Val Thr Phe Thr Trp Val
    610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
            660                 665                 670

Leu Tyr Pro Asp Ile Pro Lys Glu Glu Ala Phe Gly Lys Tyr Cys Arg
        675                 680                 685

Pro Glu Ser Gln Glu His Pro Glu Ala Asp Pro Gly Ser Ala Ala Pro
    690                 695                 700

Phe Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
            740                 745                 750
```

```
Glu Ser Leu Thr Phe Asp Met Glu Leu Thr Ser Glu Cys Ala Thr Ser
        755                 760                 765

Pro Met
    770


<210> SEQ ID NO 9
<211> LENGTH: 769
<212> TYPE: PRT
<213> ORGANISM: Homo sapiens

<400> SEQUENCE: 9

Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
        35                  40                  45

Lys Glu Ser His Ala Thr Leu Val Phe His Asn Leu Leu Gly Glu Ile
    50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
                85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
        115                 120                 125

Ala Asn His Pro Thr Ala Ala Val Val Thr Glu Lys Gln Gln Met Leu
    130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
    210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
        275                 280                 285

Gln Lys Val Ser Tyr Lys Gly Asp Pro Ile Val Gln His Arg Pro Met
    290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
            340                 345                 350
```

-continued

```
Val Lys Phe Pro Glu Leu Asn Tyr Gln Leu Lys Ile Lys Val Cys Ile
        355                 360                 365

Asp Lys Asp Ser Gly Asp Val Ala Ala Leu Arg Gly Ser Arg Lys Phe
    370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
            420                 425                 430

Thr Glu Glu Leu His Leu Ile Thr Phe Glu Thr Glu Val Tyr His Gln
        435                 440                 445

Gly Leu Lys Ile Asp Leu Glu Thr His Ser Leu Pro Val Val Ile Ser
    450                 455                 460

Asn Ile Cys Gln Met Pro Asn Ala Trp Ala Ser Ile Leu Trp Tyr Asn
465                 470                 475                 480

Met Leu Thr Asn Asn Pro Lys Asn Val Asn Phe Phe Thr Lys Pro Pro
                485                 490                 495

Ile Gly Thr Trp Asp Gln Val Ala Glu Val Leu Ser Trp Gln Phe Ser
            500                 505                 510

Ser Thr Thr Lys Arg Gly Leu Ser Ile Glu Gln Leu Thr Thr Leu Ala
        515                 520                 525

Glu Lys Leu Leu Gly Pro Gly Val Asn Tyr Ser Gly Cys Gln Ile Thr
    530                 535                 540

Trp Ala Lys Phe Cys Lys Glu Asn Met Ala Gly Lys Gly Phe Ser Phe
545                 550                 555                 560

Trp Val Trp Leu Asp Asn Ile Ile Asp Leu Val Lys Lys Tyr Ile Leu
                565                 570                 575

Ala Leu Trp Asn Glu Gly Tyr Ile Met Gly Phe Ile Ser Lys Glu Arg
            580                 585                 590

Glu Arg Ala Ile Leu Ser Thr Lys Pro Pro Gly Thr Phe Leu Leu Arg
        595                 600                 605

Phe Ser Glu Ser Ser Lys Glu Gly Gly Val Thr Phe Thr Trp Val Glu
    610                 615                 620

Lys Asp Ile Ser Gly Lys Thr Gln Ile Gln Ser Val Glu Pro Tyr Thr
625                 630                 635                 640

Lys Gln Gln Leu Asn Asn Met Ser Phe Ala Glu Ile Ile Met Gly Tyr
                645                 650                 655

Lys Ile Met Asp Ala Thr Asn Ile Leu Val Ser Pro Leu Val Tyr Leu
            660                 665                 670

Tyr Pro Asp Ile Pro Lys Glu Glu Ala Phe Gly Lys Tyr Cys Arg Pro
        675                 680                 685

Glu Ser Gln Glu His Pro Glu Ala Asp Pro Gly Ser Ala Ala Pro Tyr
    690                 695                 700

Leu Lys Thr Lys Phe Ile Cys Val Thr Pro Thr Thr Cys Ser Asn Thr
705                 710                 715                 720

Ile Asp Leu Pro Met Ser Pro Arg Thr Leu Asp Ser Leu Met Gln Phe
                725                 730                 735

Gly Asn Asn Gly Glu Gly Ala Glu Pro Ser Ala Gly Gly Gln Phe Glu
            740                 745                 750

Ser Leu Thr Phe Asp Met Glu Leu Thr Ser Glu Cys Ala Thr Ser Pro
        755                 760                 765
```

Met

<210> SEQ ID NO 10
<211> LENGTH: 770
<212> TYPE: PRT
<213> ORGANISM: Homo sapiens

<400> SEQUENCE: 10

Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
        35                  40                  45

Lys Glu Ser His Ala Thr Leu Val Phe His Asn Leu Leu Gly Glu Ile
    50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
                85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
        115                 120                 125

Ala Asn His Pro Thr Ala Ala Val Val Thr Glu Lys Gln Gln Met Leu
    130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
    210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
        275                 280                 285

Gln Lys Val Ser Tyr Lys Gly Asp Pro Ile Val Gln His Arg Pro Met
    290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
            340                 345                 350

Val Lys Phe Pro Glu Leu Asn Tyr Gln Leu Lys Ile Lys Val Cys Ile
        355                 360                 365

-continued

```
Asp Lys Asp Ser Gly Asp Val Ala Ala Leu Arg Gly Ser Arg Lys Phe
    370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
            420                 425                 430

Thr Glu Glu Leu His Leu Ile Thr Phe Glu Thr Glu Val Tyr His Gln
        435                 440                 445

Gly Leu Lys Ile Asp Leu Glu Thr His Ser Leu Pro Val Val Val Ile
    450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
        515                 520                 525

Ala Glu Lys Leu Leu Gly Pro Gly Val Asn Tyr Ser Gly Cys Gln Ile
    530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
            580                 585                 590

Arg Glu Arg Ala Ile Leu Ser Thr Lys Pro Pro Gly Thr Phe Leu Leu
        595                 600                 605

Arg Phe Ser Glu Ser Ser Lys Glu Gly Gly Val Thr Phe Thr Trp Val
    610                 615                 620

Glu Lys Asp Ile Ser Gly Lys Thr Gln Ile Gln Ser Met Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
            660                 665                 670

Leu Tyr Pro Asp Ile Pro Lys Glu Glu Ala Phe Gly Lys Tyr Cys Arg
        675                 680                 685

Pro Glu Ser Gln Glu His Pro Glu Ala Asp Pro Gly Ser Ala Ala Pro
    690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
            740                 745                 750

Glu Ser Leu Thr Phe Asp Met Glu Leu Thr Ser Glu Cys Ala Thr Ser
        755                 760                 765

Pro Met
    770
```